United States Patent
McMillan et al.

(10) Patent No.: US 6,942,971 B2
(45) Date of Patent: Sep. 13, 2005

(54) APPARATUS FOR ANALYSIS OF A NUCLEIC ACID AMPLIFICATION REACTION

(75) Inventors: William A. McMillan, Cupertino, CA (US); Lee A. Christel, Palo Alto, CA (US); David A. Borkholder, San Jose, CA (US); Steven J. Young, Los Gatos, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 10/027,404

(22) Filed: Dec. 19, 2001

(65) Prior Publication Data

US 2002/0058282 A1 May 16, 2002

Related U.S. Application Data

(60) Continuation of application No. 09/808,674, filed on Mar. 14, 2001, now Pat. No. 6,713,297, which is a division of application No. 09/562,195, filed on May 1, 2000, now Pat. No. 6,783,934.

(51) Int. Cl.[7] .......................... C12Q 1/68; C12P 19/34; C12N 9/98; G01N 33/48
(52) U.S. Cl. .......................... 435/6; 435/91.1; 435/187; 702/19
(58) Field of Search .................. 435/6, 91.1, 91.2, 435/91.21, 91.51, 187; 536/221, 231, 24.3, 25.32, 23.7; 935/77; 702/19

(56) References Cited

U.S. PATENT DOCUMENTS

| | | | |
|---|---|---|---|
| 5,219,727 A | 6/1993 | Wang et al. ................. 435/6 |
| 5,476,774 A | 12/1995 | Wang et al. ................ 435/91.2 |
| 5,710,029 A | 1/1998 | Ryder et al. ................ 435/911 |
| 5,747,246 A | 5/1998 | Pannetier et al. ............. 435/6 |
| 5,766,889 A | 6/1998 | Atwood ...................... 435/91.2 |
| 5,827,480 A | * 10/1998 | Haff ........................... 422/68.1 |
| 5,834,255 A | 11/1998 | van Gemen et al. ..... 435/91.21 |
| 5,837,501 A | 11/1998 | Beumer et al. ............ 435/91.2 |
| 5,863,736 A | 1/1999 | Haaland ........................ 435/6 |
| 6,066,458 A | 5/2000 | Haaland ........................ 435/6 |
| 6,080,574 A | 6/2000 | Berndt ...................... 435/288.7 |
| 6,174,670 B1 | 1/2001 | Wittwer et al. ................ 435/6 |
| 6,232,079 B1 | 5/2001 | Wittwer et al. ................ 435/6 |
| 6,294,338 B1 | 9/2001 | Nunomura ..................... 435/6 |
| 6,303,305 B1 | 10/2001 | Wittwer et al. ................ 435/6 |
| 6,713,297 B2 * | 3/2004 | McMillan et al. ....... 435/283.1 |
| 2003/0228596 A1 * | 12/2003 | Liu et al. ....................... 435/6 |

FOREIGN PATENT DOCUMENTS

| | | |
|---|---|---|
| EP | 0640828 A1 | 8/1994 |
| EP | 0497784 | 7/1999 |
| WO | WO 97/48707 | 6/1999 |

OTHER PUBLICATIONS

LightCycler Operator's Manual Version 3.0, May 1999, Roche Pharmaceuticals.

* cited by examiner

*Primary Examiner*—Bradley L. Sisson
(74) *Attorney, Agent, or Firm*—Townsend and Townsend and Crew LLP

(57) ABSTRACT

An apparatus for determining a threshold value (e.g., a threshold cycle number or a time value) in a nucleic acid amplification reaction comprises a detection mechanism for measuring, at a plurality of different times during the amplification reaction, at least one signal whose intensity is related to the quantity of a nucleic acid sequence being amplified in the reaction. A controller in communication with the detection mechanism is programmed to store signal values defining a growth curve for the nucleic acid sequence, determine a derivative of the growth curve, and calculate a cycle number or time value associated with a characteristic of the derivative.

51 Claims, 45 Drawing Sheets

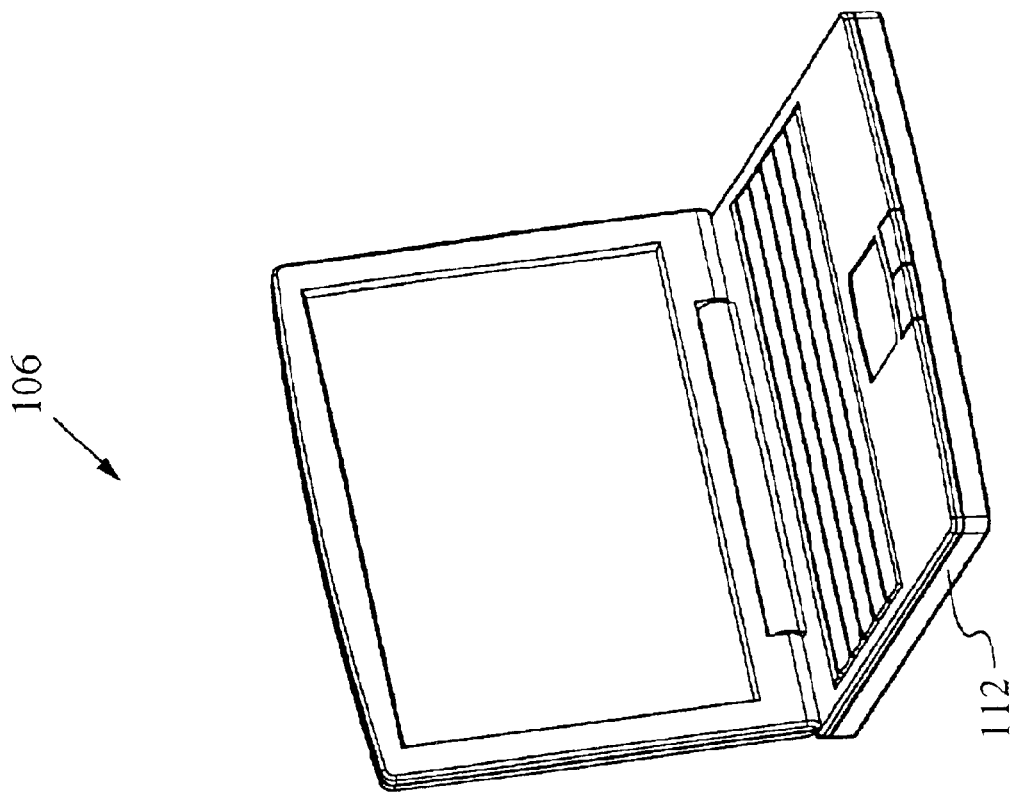
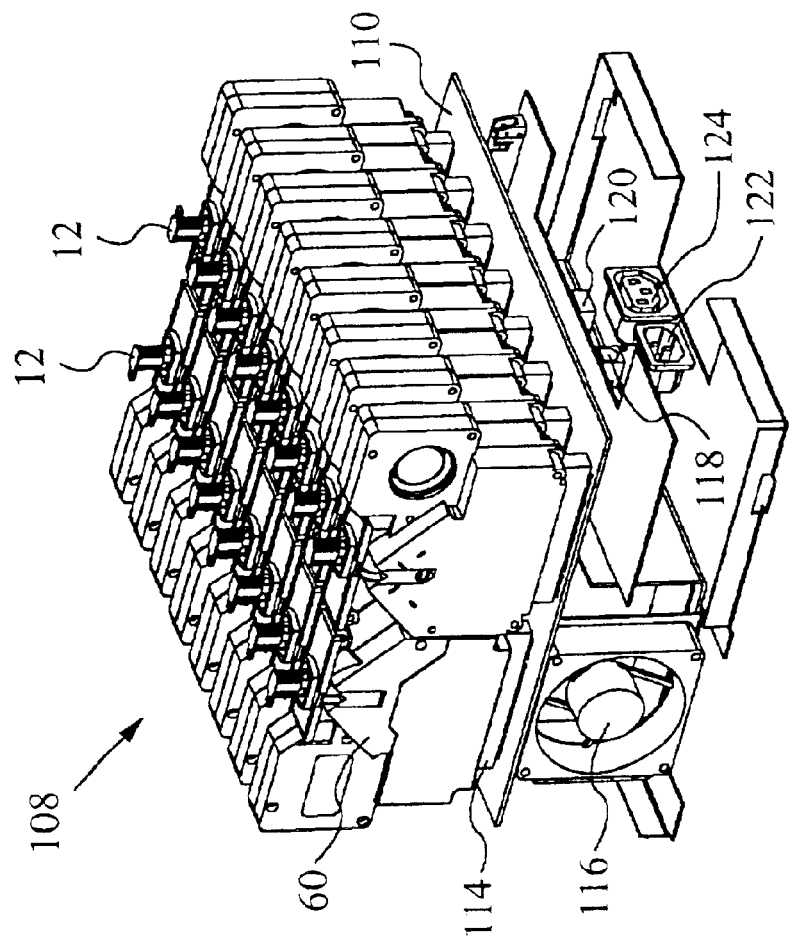
FIG. 20

| Value of Standard | | | | |
|---|---|---|---|---|
| Site | Sample Type | FAM | TET | TAM |
| A1 | STD | 1000 | 100 | 10 |
| A2 | STD | 100 | 1000 | 0 |
| A3 | STD | 0 | 0 | 1000 |
| A4 | STD | 10 | 10 | 100 |
| A5 | STD | 100 | 10 | 1000 |
| A6 | STD | 1000 | 0 | 100 |
| A7 | STD | 0 | 1000 | 0 |
| A8 | STD | 10 | 100 | 10 |

*FIG. 40*

| Threshold Values: | | | | |
|---|---|---|---|---|
| Site | Type | FAM | TET | TAM |
| A1 | STD | 27.2 | 28.1 | 29.1 |
| A2 | STD | 29.9 | 25.1 | 0 |
| A3 | STD | 0 | 0 | 22.8 |
| A4 | STD | 32.4 | 30.8 | 25.8 |
| A5 | STD | 30.1 | 31.2 | 23.2 |
| A6 | STD | 27.8 | 0 | 26.2 |
| A7 | STD | 0 | 24.9 | 0 |
| A8 | STD | 32.6 | 27.9 | 28.9 |

*FIG. 41*

From the above data, the averages are obtained for each dye at each starting quantity

| COPIES | FAM | TET | TAM |
|---|---|---|---|
| 10 | 32.5 | 31 | 29 |
| 100 | 30 | 28 | 26 |
| 1000 | 27.5 | 25 | 23 |

*FIG. 42*

| Dye: | Threshold Value | Determined Quantity |
|---|---|---|
| FAM | 29 | 251 |
| TET | 29 | 46 |
| TAM | 24 | 464 |

|      | Value of Standard |      |      |      |
|------|------|------|------|------|
| Site | Type | FAM | TET | TAM |
| A1 | STD | 1000 | 100 | N/A |
| A2 | STD | 100 | 1000 | N/A |
| A3 | STD | 0 | 0 | N/A |
| A4 | STD | 10 | 10 | N/A |
| A5 | STD | 100 | 10 | N/A |
| A6 | STD | 1000 | 0 | N/A |
| A7 | STD | 0 | 1000 | N/A |
| A8 | STD | 10 | 100 | N/A |

*FIG. 45*

|      | Threshold Values: |      |      |      |
|------|------|------|------|------|
| Site | Type | FAM | TET | TAM |
| A1 | STD | 27.2 | 28.1 | 29.1 |
| A2 | STD | 29.9 | 25.1 | 29.3 |
| A3 | STD | 0 | 0 | 29.2 |
| A4 | STD | 32.4 | 30.8 | 28.8 |
| A5 | STD | 30.1 | 31.2 | 28.7 |
| A6 | STD | 27.8 | 0 | 29.0 |
| A7 | STD | 0 | 24.9 | 29.1 |
| A8 | STD | 32.6 | 27.9 | 29.3 |

*FIG. 46*

The threshold values for each standard are normalized
to the QIC by dividing them by the threshold value of the QIC.

|  |  | Normalized Threshold Values: | | |
| --- | --- | --- | --- | --- |
| Site | Sample Type | FAM | TET | TAM |
| A1 | STD | 0.934708 | 0.965636 | 29.1 |
| A2 | STD | 1.020478 | 0.856655 | 29.3 |
| A3 | STD | 0 | 0 | 29.2 |
| A4 | STD | 1.125 | 1.069444 | 28.8 |
| A5 | STD | 1.04878 | 1.087108 | 28.7 |
| A6 | STD | 0.958621 | 0 | 29.0 |
| A7 | STD | 0 | 0.85567 | 29.1 |
| A8 | STD | 1.112628 | 0.952218 | 29.3 |

*FIG. 47*

| START COPY | FAM | TET |
| --- | --- | --- |
| 10 | 1.118814 | 1.078276 |
| 100 | 1.034629 | 0.958927 |
| 1000 | 0.946664 | 0.856163 |

*FIG. 48*

| Dye: | Threshold | QIC | Ratio | Computed Concentration |
|---|---|---|---|---|
| FAM | 29 | 28.8 | 1.006944 | 210 |
| TET | 30 | 28.8 | 1.041667 | 21 |

|      |               |     | Value of Standard | |
|------|---------------|-----|------|------|
| Site | Sample Type   | FAM | TET  | TAM  |
| A1   | Unknown w ISTD | N/A | 100  | 1000 |
| A2   | Unknown w ISTD | N/A | 100  | 1000 |
| A3   | Unknown w ISTD | N/A | 100  | 1000 |
| A4   | Unknown w ISTD | N/A | 100  | 1000 |
| A5   | Unknown w ISTD | N/A | 100  | 1000 |
| A6   | Unknown w ISTD | N/A | 100  | 1000 |
| A7   | Unknown w ISTD | N/A | 100  | 1000 |
| A8   | Unknown w ISTD | N/A | 100  | 1000 |

*FIG. 51*

| Threshold Values: | | | | |
|------|---------------|------|------|------|
| Site | Sample Type   | FAM  | TET  | TAM  |
| A1   | Unknown w ISTD | 27.2 | 30.0 | 27.0 |
| A2   | Unknown w ISTD | 29.9 | 30.2 | 27.1 |
| A3   | Unknown w ISTD | 0    | 30.5 | 27.4 |
| A4   | Unknown w ISTD | 32.4 | 29.8 | 26.8 |
| A5   | Unknown w ISTD | 30.1 | 29.9 | 26.8 |
| A6   | Unknown w ISTD | 27.8 | 29.5 | 26.5 |
| A7   | Unknown w ISTD | 0    | 29.7 | 26.6 |
| A8   | Unknown w ISTD | 32.6 | 30.0 | 27.1 |

*FIG. 52*

| Start Qty | Threshold | Log Start Qty |
|---|---|---|
| 100 | 30.2 | 2 |
| 1000 | 27.1 | 3 |

APPARATUS FOR ANALYSIS OF A NUCLEIC ACID AMPLIFICATION REACTION

This application is a continuation of U.S. Ser. No. 09/808,674 filed Mar. 14, 2001, now U.S. Pat. No. 6,713, 297, which application is a division of U.S. Ser. No. 09/562, 195 filed May 1, 2000, now U.S. Pat. No. 6,783,934. All of these applications are incorporated by reference herein for all purposes.

COPYRIGHT AUTHORIZATION

A portion of the disclosure of this patent document contains material which is subject to copyright protection. The copyright owner has no objection to the facsimile reproduction by any one of the patent disclosure as it appears in the U.S. Patent and Trademark Office patent files or records, but otherwise reserves all copyright rights whatsoever.

TECHNICAL FIELD OF THE INVENTION

This invention relates to an apparatus for analysis of a nucleic acid amplification reaction.

BACKGROUND OF THE INVENTION

Quantitative nucleic sequence analysis plays an increasingly important role in the fields of biological and medical research. For example, quantitative gene analysis has been used to determine the genome quantity of a particular gene, as in the case of the human HER-2 oncogene, which is amplified in approximately 30% of human breast cancers. Gene and genome quantitation have also been used in determining and monitoring the levels of human immunodeficiency virus (HIV) in a patient throughout the different phases of the HIV infection and disease. It has been suggested that higher levels of circulating HIV and failure to effectively control virus replication after infection may be associated with a negative disease prognosis. Accordingly, an accurate determination of nucleic acid levels early in an infection may serve as a useful tool in diagnosing illness, while the ability to correctly monitor the changing levels of viral nucleic acid in one patient throughout the course of an illness may provide clinicians with critical information regarding the effectiveness of treatment and progression of disease.

Several methods have been described for the quantitative analysis of nucleic acid sequences. The polymerase chain reaction (PCR) and reverse-transcriptase PCR (RT-PCR) permit the analysis of small starting quantities of nucleic acid (e.g., as little as one cell equivalent). Early methods for quantitation involved measuring PCR product at the end of temperature thermal cycling and relating this level to the starting DNA concentration. Unfortunately, the absolute amount of product generated does not always bear a consistent relationship to the amount of target sequence present at the initiation of the reaction, particularly for clinical samples. Such an endpoint analysis reveals the presence or absence of starting nucleic acid, but generally does not provide an accurate measure of the number of DNA targets. Both the kinetics and efficiency of amplification of a target sequence are dependent on the starting quantity of that sequence, and on the sequence match of the primers and target template, and may also be affected by inhibitors present in the sample. Consequently, endpoint measurements have very poor reproducibility.

Another method, quantitative competitive PCR (QC-PCR), has been developed and used widely for PCR quantitation. QC-PCR relies on the inclusion of a known amount of an internal control competitor in each reaction mixture. To obtain relative quantitation, the unknown target PCR product is compared with the known competitor PCR product, usually via gel electrophoresis. The relative amount of target-specific and competitor DNA is measured, and this ratio is used to calculate the starting number of target templates. The larger the ratio of target specific product to competitor specific product, the higher the starting DNA concentration. Success of a QC-PCR assay relies on the development of an internal control that amplifies with the same efficiency as the target molecule. However, the design of the competitor and the validation of amplification efficiencies require much effort. In the QC-PCR method of RNA quantitation, a competitive RNA template matched to the target sequence of interest, but different from it by virtue of an introduced internal deletion, is used in a competitive titration of the reverse transcription and PCR steps, providing stringent internal control. Increasing amounts of known copy numbers of competitive template are added to replication portions of the test sample, and quantitation is based on determination of the relative (not absolute) amounts of the differently sized amplified products derived from the wild-type and competitive templates, after electrophoretic separation.

In addition to requiring time-consuming and burdensome downstream processing such as hybridization or gel electrophoresis, these assays have limited sensitivity to a range of target nucleic acid concentrations. For example, in competitor assays, the sensitivity to template concentration differences may be compromised when either the target or added competitor DNA is greatly in excess of the other. The dynamic range of the assays that measure the amount of end product can also be limited in that the chosen number of cycles of some reactions may have reached a plateau level of product prior to other reactions. Differences in starting template levels in these reactions may therefore not be well reflected. Furthermore, small differences in the measured amount of product may result in widely varying estimates of the starting template concentration, leading to inaccuracies due to variable reaction conditions, variations in sampling, or the presence of inhibitors.

To reduce the amount of post-amplification analysis required to determine a starting nucleic acid quantity in a sample, additional methods have been developed to measure nucleic acid amplification in real-time. These methods generally take advantage of fluorescent labels (e.g., fluorescent dyes) that indicate the amount of nucleic acid being amplified, and utilize the relationship between the number of cycles required to achieve a chosen level of fluorescence signal and the concentration of amplifiable targets present at the initiation of the PCR process. For example, European Patent Application No. 94112728 (Publication number EP/0640828) describes a quantitative assay for an amplifiable nucleic acid target sequence which correlates the number of thermal cycles required to reach a certain concentration of target sequence to the amount of target DNA present at the beginning of the PCR process. In this assay system, a set of reaction mixtures are prepared for amplification, with one preparation including an unknown concentration of target sequence in a test sample and others containing known concentrations (standards) of the sequence. The reaction mixtures also contain a fluorescent dye that fluoresces when bound to double-stranded DNA.

The reaction mixtures are thermally cycled in separate reaction vessels for a number of cycles to achieve a sufficient amplification of the targets. The fluorescence emitted from the reaction mixtures is monitored in real-time as the amplification reactions occur, and the number of cycles necessary for each reaction mixture to fluoresce to an arbitrary cutoff level (arbitrary fluorescent value, or AFV) is determined. The AFV is chosen to be in a region of the amplification curves that is parallel among the different standards (e.g., from 0.1 to 0.5 times the maximum fluorescence value obtained by the standard using the highest initial known target nucleic acid concentration). The number of cycles necessary for each of the standards to reach the AFV is determined, and a regression line is fitted to the data that relates the initial target nucleic acid amount to the number of cycles (i.e., the threshold cycle number) needed to reach the AFV. To determine the unknown starting quantity of the target nucleic acid sequence in the sample, the number of cycles needed to reach the AFV is determined for the sample. This threshold cycle number (which can be fractional) is entered into the equation of the fitted regression line and the equation returns a value that is the initial amount of the target nucleic acid sequence in the sample.

The primary disadvantage of this method for determining an unknown starting quantity of a target nucleic acid sequence in a sample is that differences in background signal, noise, or reaction efficiency between the reaction mixtures being amplified in different reaction vessels may bias the calculation of the threshold cycle numbers. Consequently, several of the data points used to generate the regression line may deviate significantly from linearity, resulting in inaccurate quantitation of the unknown starting quantity of the target nucleic acid sequence in the sample. Small differences in the selection of threshold cycle numbers used in quantitation algorithms may have a substantial effect on the ultimate accuracy of quantitation. Thus, there remains a need to provide an objective and automatic method of selecting threshold values that will allow users of amplification methods to determine the initial concentrations of target nucleic acid sequences more accurately and reliably than present methods.

SUMMARY

It is therefore an object of the present invention to provide an improved apparatus for determining a threshold value in a nucleic acid amplification reaction. The threshold value may be a threshold cycle number in a thermal cycling amplification reaction, or the threshold value may be a time value (e.g., an elapsed time of amplification) in an isothermal nucleic acid amplification reaction.

It is another object of the present invention to provide an improved apparatus for determining an unknown starting quantity of a nucleic acid sequence in a test sample.

According to a first embodiment, the invention provides an apparatus for determining a threshold cycle number (which may be fractional) in a nucleic acid amplification reaction. The apparatus comprises a detection mechanism for measuring, at a plurality of different times during the amplification reaction, at least one signal whose intensity is related to the quantity of a nucleic acid sequence being amplified in the reaction. The apparatus also includes a controller (e.g., a computer or processor) in communication with the detection mechanism. The controller is programmed to perform the steps of deriving a growth curve from the measurements of the signal; calculating a derivative of the growth curve; identifying a characteristic of the derivative; and determining a cycle number associated with the characteristic of the derivative. The step of calculating a derivative of the growth curve preferably comprises calculating second derivative values of the growth curve at a number of different cycles in the reaction to yield a plurality of second derivative data points. The characteristic of the derivative is preferably a positive peak of the second derivative, and the step of determining the cycle number associated with the positive peak preferably comprises fitting a second order curve to the second derivative data points and calculating the threshold cycle number as the location, in cycles, of a peak of the second order curve. Alternatively, the characteristic of the derivative used to determine the threshold cycle number may comprise a negative peak of the second derivative, a zero crossing of the second derivative, or a positive peak of the first derivative.

According to a second embodiment, the invention provides an apparatus for determining a threshold time value in a nucleic acid amplification reaction. The method is particularly useful for determining a threshold time value (e.g., an elapsed time of amplification required to reach a threshold level) in isothermal nucleic acid amplification reactions. The apparatus comprises a detection mechanism for measuring, at a plurality of different times during the amplification reaction, at least one signal whose intensity is related to the quantity of a nucleic acid sequence being amplified in the reaction. The apparatus also includes a controller (e.g., a computer or processor) in communication with the detection mechanism. The controller is programmed to perform the steps of deriving a growth curve from the measurements of the signal; calculating a derivative of the growth curve; identifying a characteristic of the derivative; and determining a time value associated with the characteristic of the derivative. The step of calculating a derivative of the growth curve preferably comprises calculating second derivative values of the growth curve at a number of different times in the reaction to yield a plurality of second derivative data points. The characteristic of the derivative is preferably a positive peak of the second derivative, and the step of determining the time value associated with the positive peak preferably comprises fitting a second order curve to the second derivative data points and calculating the threshold time value as the location of a peak of the second order curve. Alternatively, the characteristic of the derivative used to determine the threshold time value may comprise a negative peak of the second derivative, a zero crossing of the second derivative, or a positive peak of the first derivative.

Using derivatives of growth curves to determine threshold values provides for highly reproducible threshold values even when there is significant variation (e.g., in terms of timing, optics, or noise due to other sources) between the reaction sites at which the various test and calibration samples are amplified. The threshold value for each target nucleic acid sequence being amplified in a particular reaction is based on the data from that reaction, not from all of the reactions in a batch so that a single discrepant reaction in the batch will not bias the calculation of threshold values for target nucleic acid sequences at other reaction sites.

According to another embodiment, the invention provides an apparatus for determining an unknown starting quantity of a target nucleic acid sequence in a test sample. The apparatus comprises means for amplifying the unknown starting quantity of the target nucleic acid sequence in the test sample and for amplifying a plurality of known starting quantities of a calibration nucleic acid sequence in respective calibration samples. The apparatus also includes at least one detection mechanism for measuring, at a plurality of different times during amplification of the nucleic acid sequences, signals indicative of the quantities of the nucleic acid sequences being amplified in the test and calibration samples. The apparatus further includes at least one controller (e.g., computer or processor) in communication with the detection mechanism. The controller is programmed to determine a respective threshold value for each of the known starting quantities of the calibration nucleic acid sequence in the calibration samples and for the target nucleic acid sequence in the test sample. Each threshold value is determined for a nucleic acid sequence in a respective sample by deriving a growth curve for the nucleic acid sequence from the measured signals; calculating a derivative of the growth curve; identifying a characteristic of the derivative; and determining the threshold value associated with the characteristic of the derivative. The controller is also programmed to derive a calibration curve from the threshold values determined for the known starting quantities of the nucleic acid sequence in the calibration samples and to determine the starting quantity of the target nucleic acid sequence in the test sample using the calibration curve and the threshold value determined for the target sequence.

BRIEF DESCRIPTION OF THE DRAWINGS

FIG. 20 is an isometric view of a multi-site reactor system according to the present invention.

FIG. 40 is a setup table containing the known starting quantities of nucleic acid sequences in calibration samples (standards).

FIG. 41 is a table containing the threshold values determined for the nucleic acid sequences in the calibration samples of FIG. 40.

FIG. 42 is a table of averages computed from the table of FIG. 41.

FIG. 45 is a setup table containing the known starting quantities of nucleic acid sequences in calibration samples (standards) according to another embodiment of the invention. Each sample includes a quantitative internal control (QIC).

FIG. 46 is a table containing the threshold values determined for the nucleic acid sequences and for the quantitative internal controls in the calibration samples of FIG. 40.

FIG. 47 is a table of normalized threshold values.

FIG. 48 is a table of averages computed from the table of FIG. 47.

FIG. 51 is a setup table containing the known starting quantities of two different calibration nucleic acid sequences (internal standards) at each reaction site.

FIG. 52 is a table containing the threshold values determined for the calibration nucleic acid sequences of FIG. 51.

DETAILED DESCRIPTION

Figure 1:
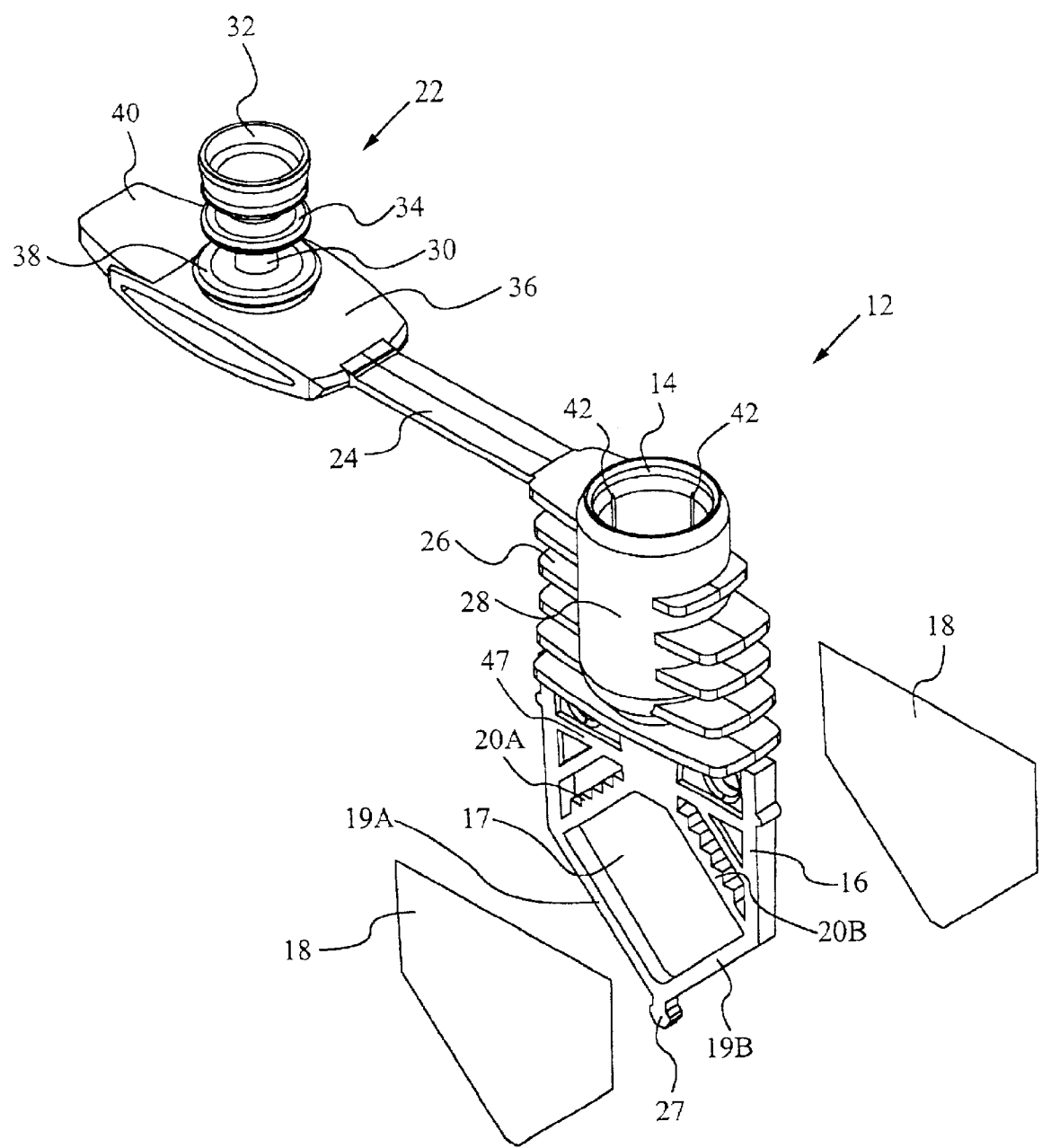
FIG. 1 is a partially exploded, isometric view of a reaction vessel in which the major walls of the reaction chamber are removed to show the interior of the chamber.
Figure 2:
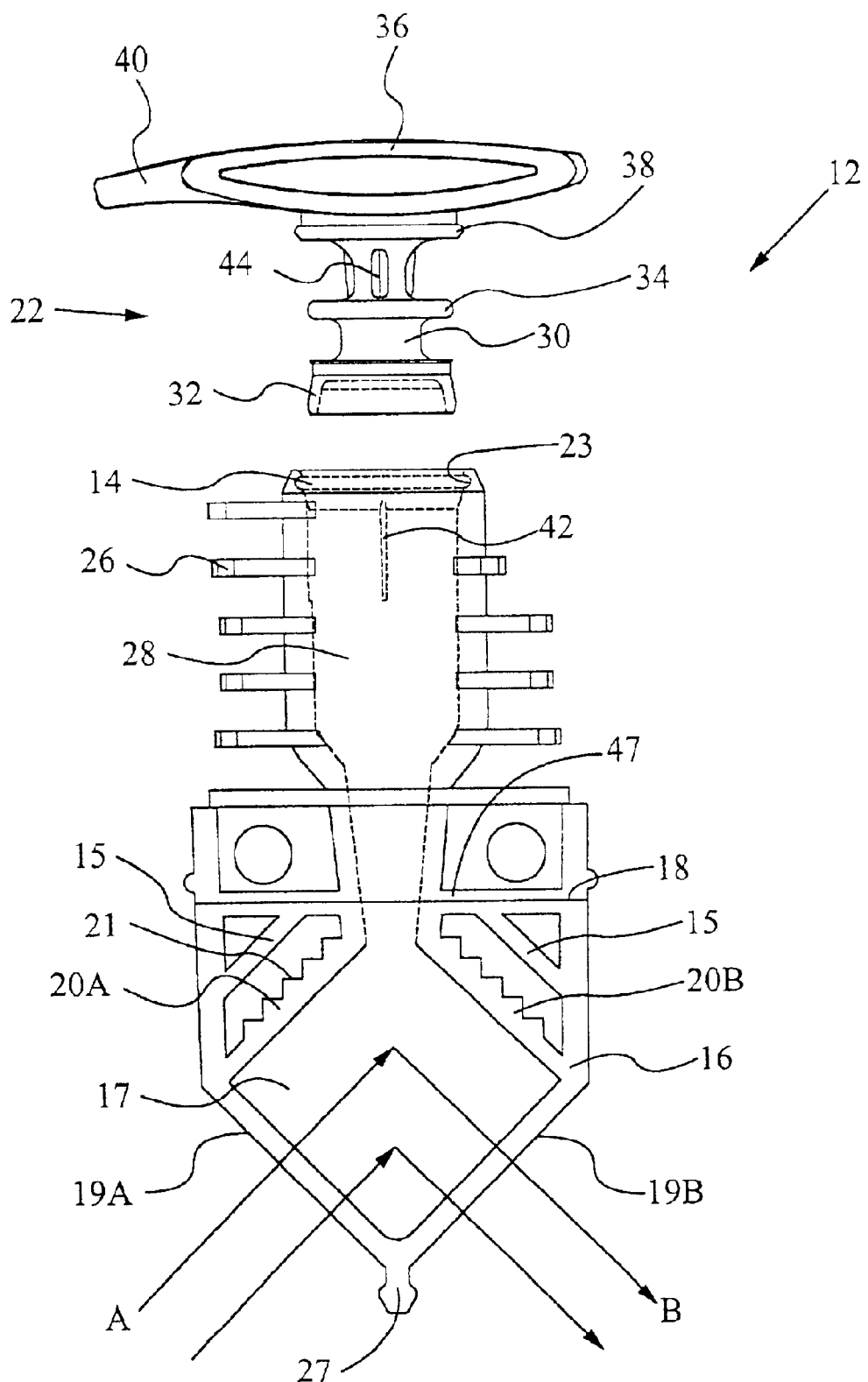
FIG. 2 is a front view of the vessel of FIG. 1.

The present invention provides methods, apparatus, and computer program products for determining quantities of target nucleic acid sequences in samples. FIG. 1 shows a partially exploded view of a reaction vessel 12 for holding a sample for nucleic acid amplification and detection. FIG. 2 shows a front view of the vessel 12. The vessel 12 includes a reaction chamber 17 for holding a reaction mixture (e.g., the sample mixed with reagents and one or more fluorescent dyes) for thermal processing and optical interrogation. The vessel 12 is designed for optimal heat transfer to and from the mixture and for efficient optical viewing of the mixture. The thin shape of the vessel contributes to optimal thermal kinetics by providing large surfaces for thermal conduction. In addition, the side walls of the vessel 12 provide optical windows into the chamber 17 so that the entire reaction mixture can be optically interrogated in real-time as the nucleic acid amplification reaction occurs.

In more detail to FIGS. 1–2, the reaction vessel 12 includes a rigid frame 16 that defines the side walls 19A, 19B, 20A, 20B of the reaction chamber 17. The rigid frame 16 also includes a port 14 and a channel 28 that connects the port 14 to the chamber 17. The vessel also includes thin, flexible sheets attached to opposite sides of the rigid frame 16 to form opposing major walls 18 of the chamber. (The major walls 18 are shown in FIG. 1 exploded from the rigid frame 16 for illustrative clarity). The reaction chamber 17 is thus defined by the rigid side walls 19A, 19B, 20A, 20B of the frame 16 and by the flexible major walls 18 which are sealed to opposite sides of the frame.

The major walls 18 facilitate optimal thermal conductance to the reaction mixture contained in the chamber 17. Each of the walls 18 is sufficiently flexible to contact and conform to a respective thermal surface, thus providing for optimal thermal contact and heat transfer between the thermal surface and the reaction mixture contained in the chamber 17. Furthermore, the flexible walls 18 continue to conform to the thermal surfaces if the shape of the surfaces changes due to thermal expansion or contraction during the course of the heat-exchanging operation.

Figure 5:
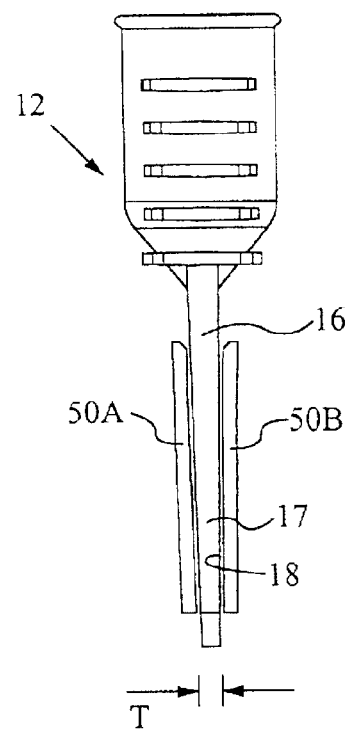
FIG. 5 is a side view of the vessel of FIG. 1 inserted into a thermal sleeve formed by opposing plates.

As shown in FIG. 5, the thermal surfaces for contacting the flexible walls 18 are preferably formed by a pair of opposing plates 50A, 50B positioned to receive the chamber 17 between them. When the chamber 17 of the vessel is inserted between the plates 50A, 50B, the inner surfaces of the plates contact the walls 18 and the flexible walls conform to the surfaces of the plates. The plates are preferably spaced a distance from each other equal to the thickness T of the chamber 17 as defined by the thickness of the frame 16. In this position, minimal or no gaps are found between the plate surfaces and the walls 18. The plates may be heated and cooled by various thermal elements to induce temperature changes within the chamber 17, as is described in greater detail below.

The walls 18 are preferably flexible films of polymeric material such as polypropylene, polyethylene, polyester, or other polymers. The films may either be layered, e.g., laminates, or the films may be homogeneous. Layered films are preferred because they generally have better strength and structural integrity than homogeneous films. In particular, layered polypropylene films are presently preferred because polypropylene is not inhibitory to PCR. Alternatively, the walls 18 may comprise any other material that may be formed into a thin, flexible sheet and that permits rapid heat transfer. For good thermal conductance, the thickness of each wall 18 is preferably between about 0.003 to 0.5 mm, more preferably between 0.01 to 0.15 mm, and most preferably between 0.025 to 0.08 mm.

Referring again to FIGS. 1–2, the reaction vessel 12 also includes a plunger 22 that is inserted into the channel 28 after filling the chamber 17 with the reaction mixture. The plunger 22 compresses gas in the vessel 12 thereby increasing pressure in the chamber 17 and outwardly expanding the flexible walls 18. The gas compressed by the plunger 22 is typically air filling the channel 28. The pressurization of the chamber 17 is important because it forces the walls 18 against the surfaces of the plates 50A, 50B (see FIG. 5) and ensures that the walls 18 fully contact and conform to the inner surfaces of the plates, thus guaranteeing optimal thermal conductance between the plates 50A, 50B and the chamber 17.

Referring again to FIGS. 1–2, the plunger may comprise any device capable of establishing a seal with the walls of the channel 28 and of compressing gas in the vessel. Such devices include, but are not limited to, pistons, plugs, or stoppers. The plunger 22 of the preferred embodiment includes a stem 30 and a piston 32 on the stem. When the plunger 22 is inserted into the channel 28, the piston 32 establishes a seal with the inner walls of the channel and compresses air in the channel. The piston 32 is preferably a cup integrally formed (e.g., molded) with the stem 30. Alternatively, the piston 32 may be a separate elastomeric piece attached to the stem.

The plunger 22 also preferably includes an alignment ring 34 encircling the stem for maintaining the plunger 22 in coaxial alignment with the channel 28 as the plunger is inserted into the channel. The alignment ring 34 is preferably integrally formed (e.g., molded) with the stem 30. The stem 30 may optionally includes support ribs 44 for stiffening and strengthening the stem. The plunger 22 also includes a plunger cap 36 attached to the stem 30. As shown in FIG. 2, the cap 36 includes a snap ring 38 and the vessel includes an annular recess 23 encircling the port 14 for receiving the snap ring 38. The cap 36 may optionally include a lever portion 40 which is lifted to remove the plunger 22 from the channel 28.

Figure 7A:
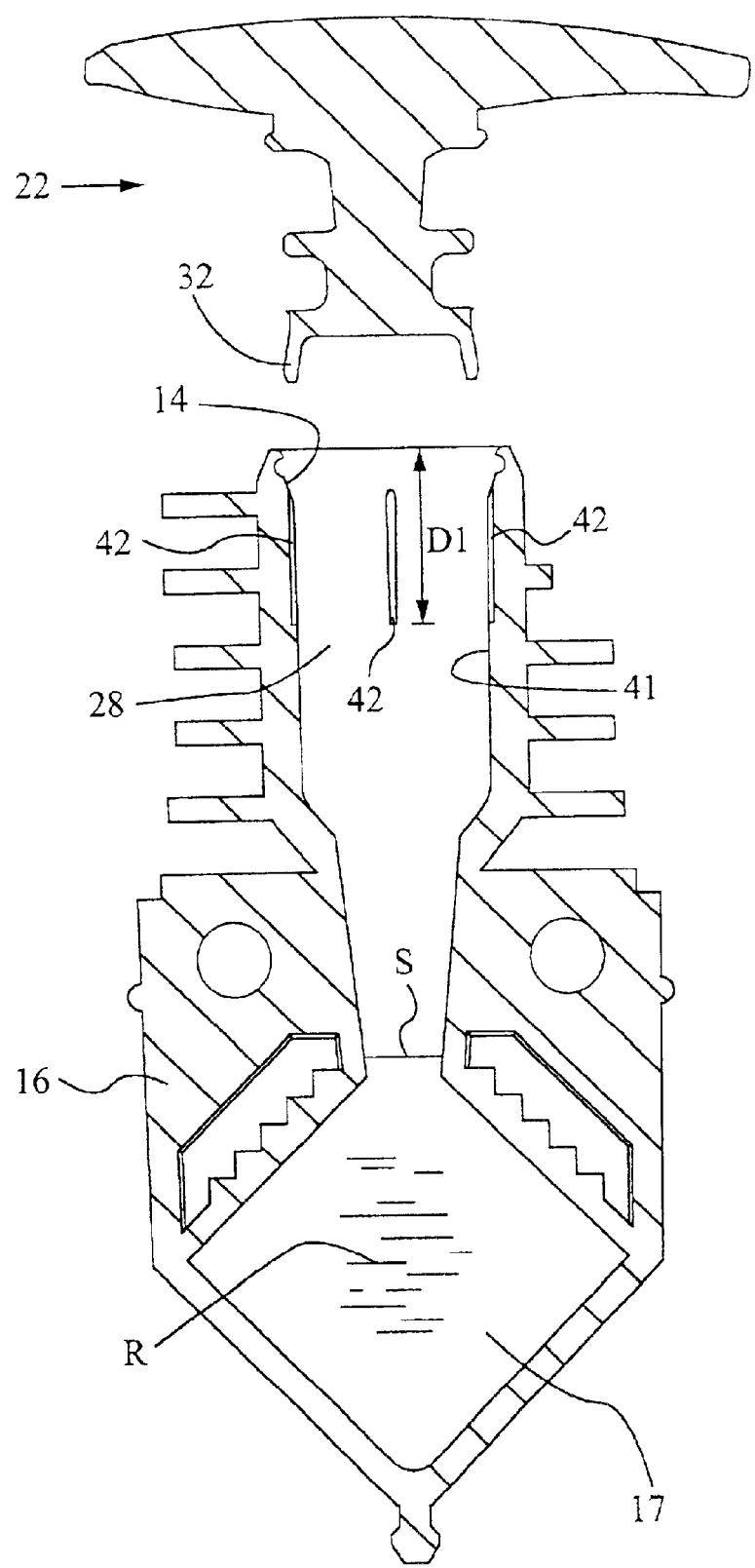
FIGS. 7A–7D are schematic, cross-sectional views of a plunger being inserted into a channel of the reaction vessel of FIG. 1.

Referring to FIG. 7A, the rigid frame 16 has an inner surface 41 defining the channel 28. The inner surface 41 preferably has one or more pressure control grooves 42 formed therein. In the preferred embodiment, the inner surface has four pressure control grooves (only three shown in the view of FIG. 7A) spaced equidistantly about the circumference of the channel 28. The pressure control grooves 42 extend from the port 14 to a predetermined depth $D_1$ in the channel 28. The pressure control grooves 42 allow gas to escape from the channel 28 and thus prevent pressurization of the chamber 17 until the piston 32 reaches the depth $D_1$ in the channel. When the piston 32 reaches the depth $D_1$, the piston establishes an annular seal with the walls of the channel 28 and begins to compress air trapped in the channel. The compression of the trapped air causes the desired pressurization of the chamber 17.

Figure 7B:
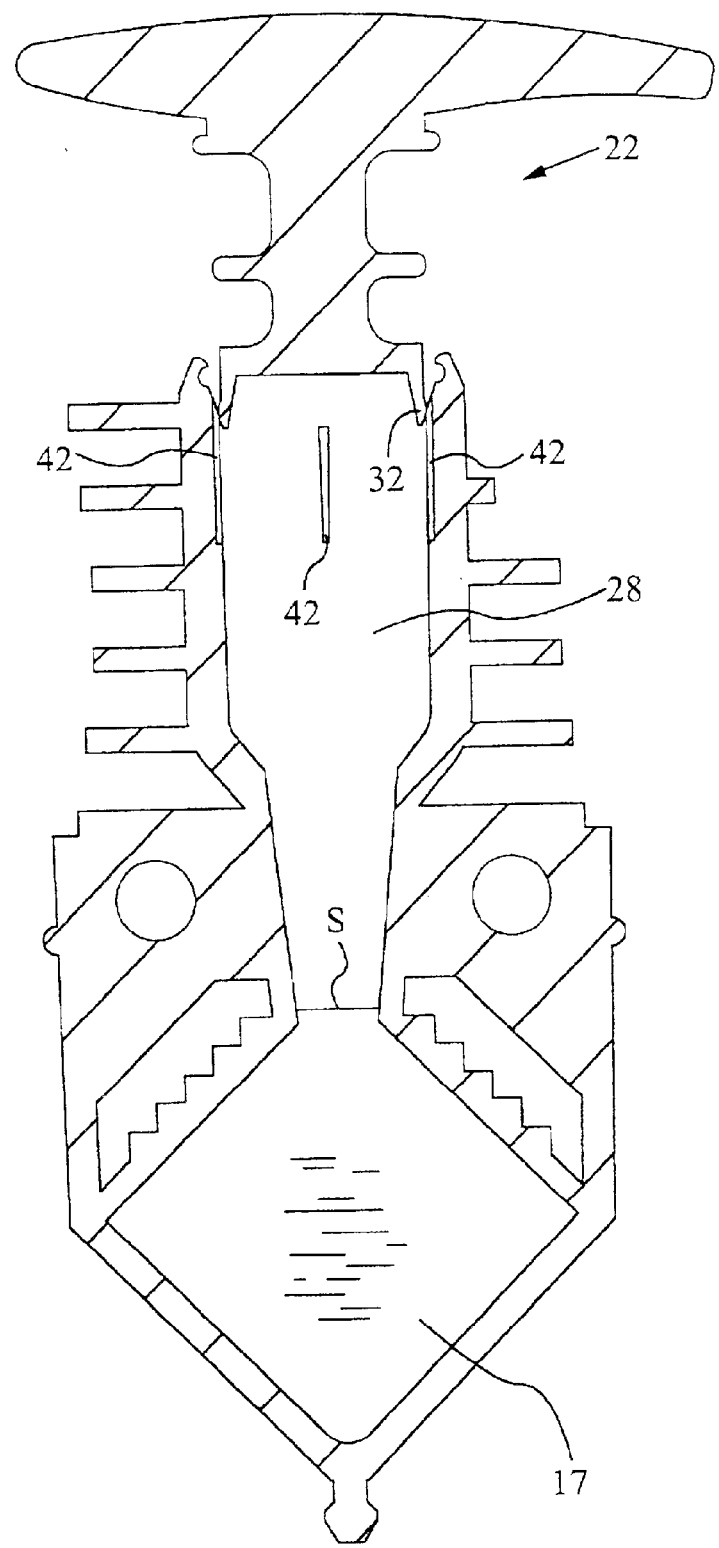

The stroke of the plunger 22 into the channel 28 is fully illustrated in FIGS. 7A–7D. As shown in FIG. 7A, prior to inserting the plunger 22 into the channel 28, the chamber 17 is filled with the desired reaction mixture R. Specific methods for filling the chamber (e.g., pipetting) are discussed in detail below. The reaction mixture R fills the vessel 12 to a liquid surface level S. Also prior to inserting the plunger 22 into the channel 28, the channel 28 contains air having pressure equal to the pressure of the atmosphere external to the vessel, hereinafter called ambient pressure. The ambient pressure is usually standard atmospheric pressure, e.g., about 14.7 pounds per square inch (psi). As shown in FIG. 7B, when the plunger 22 is first inserted into the channel 28, the piston 32 begins to displace the air in the channel. The displaced air escapes from the channel 28 through the pressure control grooves 42.

Figure 7C:
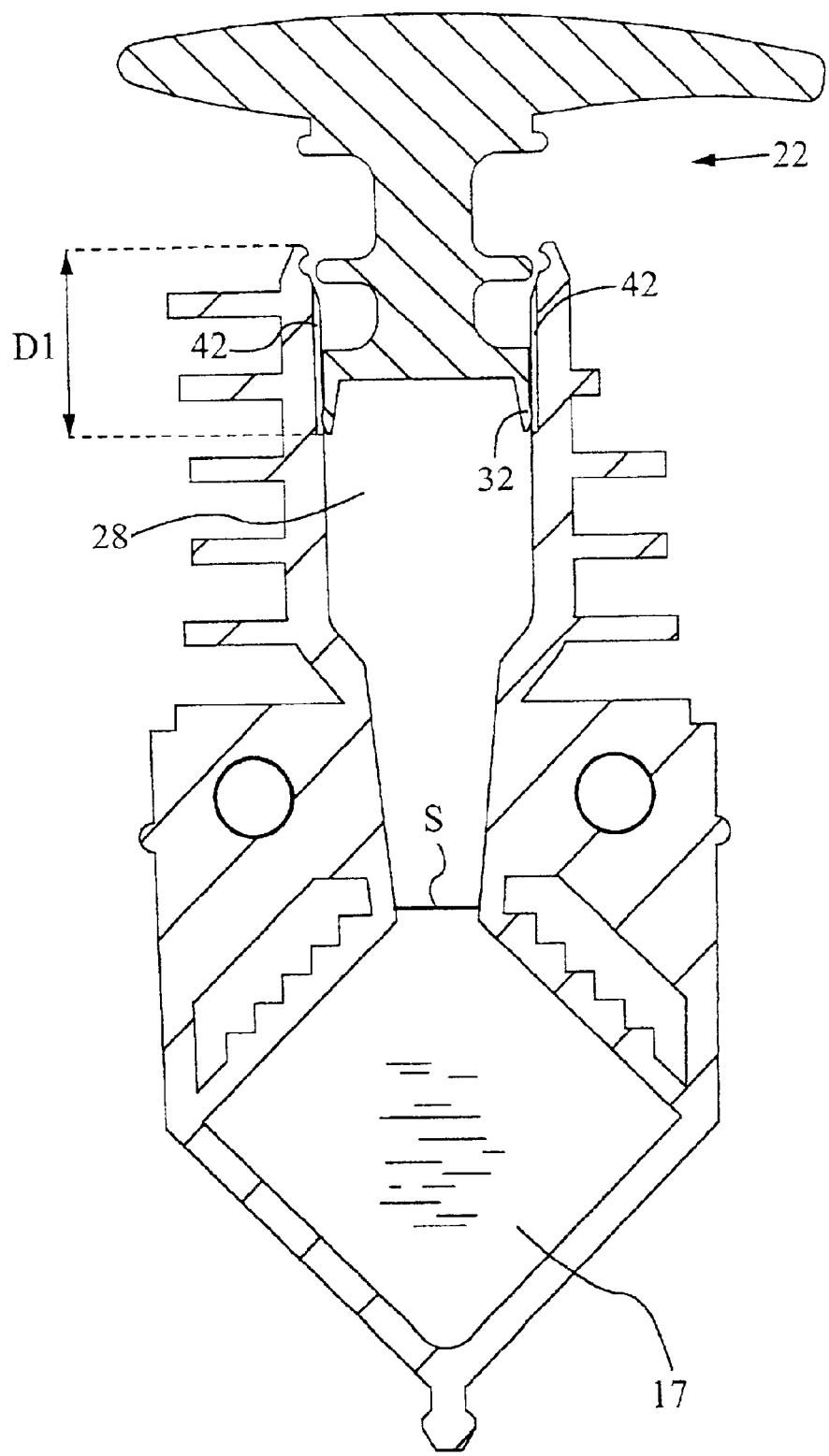
Figure 7D:
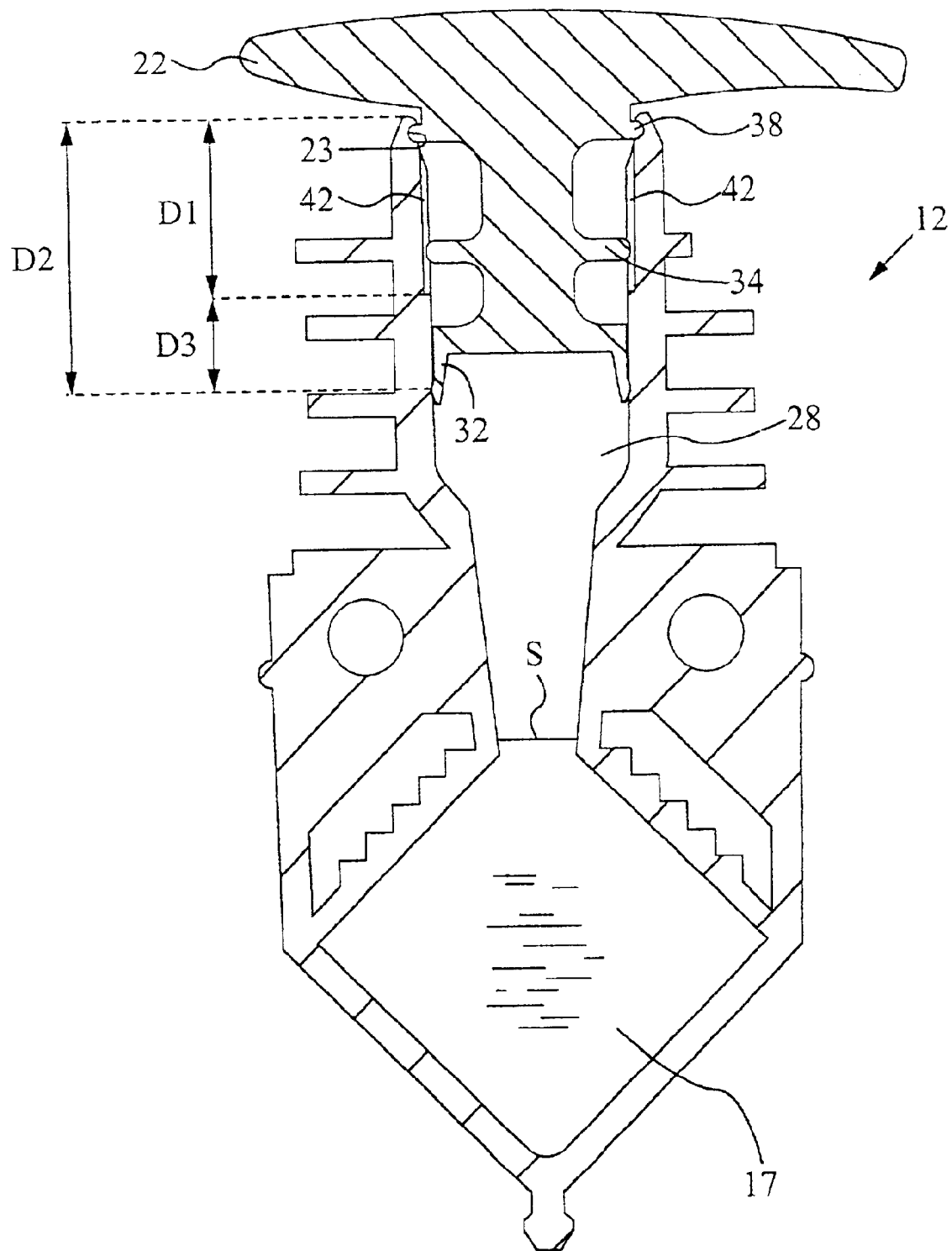

Referring now to FIG. 7C, when the piston 32 reaches the depth $D_1$ at which the pressure control grooves end, the piston 32 establishes an annular seal with the walls of the channel 28 and begins to compress air trapped in the channel between the piston 32 and the surface level S of the reaction mixture. The reaction mixture is usually a liquid and therefore substantially incompressible by the piston. The air trapped in the channel 28, however, may be compressed to increase pressure in the chamber. As shown in FIG. 7D, as the plunger 22 is inserted further into the channel 28, the alignment ring 34 keeps the plunger 22 coaxially aligned with the channel 28 as the piston 32 continues to compress air trapped in the channel. When the plunger 22 is fully inserted in the channel 28, the snap ring 38 snaps into the annular recess 23, ending the plunger stroke.

When the plunger 22 is fully inserted, the piston 32 seals the channel 28 at a depth $D_2$ which is lower than the depth $D_1$ at which the pressure control grooves 42 terminate. The distance $D_3$ traveled by the piston 32 between depths $D_1$ and $D_2$, i.e. the distance of the pressure stroke, determines the amount of pressurization of the chamber 17. Referring again to FIG. 5, the pressure in the chamber 17 should be sufficiently high to ensure that the flexible major walls 18 of the chamber outwardly expand to contact and conform to the surfaces of the plates 50A, 50B. The pressure should not be so great, however, that the flexible walls 18 burst, become unattached from the rigid frame 16, or deform the frame or plates.

It is presently preferred to pressurize the chamber to a pressure in the range of 2 to 50 psi above ambient pressure. This range is presently preferred because 2 psi is generally enough pressure to ensure conformity between the flexible walls 18 and the surfaces of the plates 50A, 50B, while pressures above 50 psi may cause bursting of the walls 18 or deformation of the frame 16 or plates 50A, 50B. More preferably, the chamber 17 is pressurized to a pressure in the range of 8 to 15 psi above ambient pressure. This range is more preferred because it is safely within the practical limits described above, i.e. pressures of 8 to 15 psi are usually more than enough to ensure that the flexible walls 18 contact and conform to the surfaces of the plates 50A, 50B, but are significantly lower than the pressures that might burst the walls 18 or deform the frame 16.

Referring again to FIG. 7D, the desired pressurization of the chamber 17 may be achieved by proper design of the plunger 22, channel 28, and pressure control grooves 42 and by use of the equation:

$$P_1 * V_1 = P_2 * V_2;$$

where:

$P_1$ is equal to the pressure in the vessel 12 prior to insertion of the plunger 22;

$V_1$ is equal to the volume of the channel 28 between the liquid surface level S and the depth $D_1$ to which the pressure control grooves 42 extend;

$P_2$ is equal to the desired final pressure in the chamber 17 after insertion of the plunger 22 into the channel 28; and $V_2$ is equal to the volume of the channel 28 between the liquid surface level S and the depth $D_2$ at which the piston 32 establishes a seal with the walls of the channel 28 when the plunger 22 is fully inserted into the channel.

To ensure the desired pressurization $P_2$ of the chamber 17, one should size the channel 28 and pressure stroke distance $D_3$ such that the ratio of the volumes $V_1:V_2$ is equal to the ratio of the pressures $P_2:P_1$. An engineer having ordinary skill in the art will be able to select suitable values for the volumes $V_1$ and $V_2$ using the description and equation given above. For example, in the presently preferred embodiment, the initial pressure $P_1$ in the vessel is equal to standard atmospheric pressure of about 14.7 psi, the volume $V_1$ is equal to 110 $\mu$l, the depth $D_1$ is equal to 0.2 inches, the depth $D_2$ is equal to 0.28 inches to give a pressure stroke distance $D_3$ of 0.08 inches, and the volume $V_2$ is equal to 60 μl to give a final pressure $P_2$ of about 26.7 psi (the desired 12 psi above ambient pressure). This is just one example of suitable dimensions for the vessel 12 and is not intended to limit the scope of the invention. Many other suitable values may be selected.

In selecting suitable dimensions for the channel 28 and pressure stroke distance $D_3$ (and thus the volumes $V_1$, $V_2$), there is no theoretical limit to how large or small the dimensions may be. It is only important that the ratio of the volumes $V_1:V_2$ yield the desired final desired pressure $P_2$ in the chamber. As a practical matter, however, it is presently preferred to design the vessel such that the distance $D_3$ of the pressure stroke is at least 0.05 inches, i.e., so that the plunger 22 when fully inserted into the channel 28 extends to a depth $D_2$ that is at least 0.05 inches below the depth $D_1$ at which the pressure control grooves end. This minimum length of the pressure stroke is preferred to reduce or make negligible the effect that any manufacturing or operating errors may have on the pressurization of the chamber. For example, the length of the pressure stroke may differ slightly from vessel to vessel due to manufacturing deviations, or the volume of air compressed may vary due to operator error in filling the vessel (e.g., different fill levels). If the vessel is designed to have a sufficiently long pressure stroke, however, such variances will have a lesser or negligible effect on the ratio of volumes $V_1:V_2$ and suitable pressurization of the chamber will still occur. In addition, to provide a safety margin for manufacturing or operator errors, one should select a pressure stroke sufficient to achieve a final pressure $P_2$ that is safely higher (e.g., at least 3 psi higher) than the minimum pressure needed to force the flexible walls of the chamber against the inner surfaces of the plates. With such a safety margin, any deviations in the final pressure due to manufacturing deviations or errors in filling the chamber will have a negligible effect and suitable pressurization of the chamber 17 will still occur. As stated above, the plunger stroke is preferably designed to increase pressure in the chamber 17 to a pressure in the range of 8 to 15 psi above ambient pressure to provide the safety margin.

The pressure control grooves 42 provide several important advantages. First, the pressure control grooves 42 provide a simple mechanism for precisely and accurately controlling the pressure stroke of the plunger 22, and hence the pressurization of the chamber 17. Second, the pressure control grooves 42 allow the plunger 22 to become fully aligned with the channel 28 before the pressure stroke begins and thus prevent the plunger from becoming misaligned or cocked in the channel. This ensures a highly consistent pressure stroke. Although it is possible for the vessel to have only one pressure control groove, it is preferable for the vessel to have multiple pressure control grooves (e.g., 2 to 6 grooves) spaced equidistantly about the circumference of the channel 28. Referring again to FIG. 7A, the pressure control grooves 42 preferably cut about 0.01 to 0.03 inches into the surface 41 defining the channel 28. This range is preferred so that the pressure control grooves 42 are large enough to allow air to escape from the channel 28, but do not cut so deeply into the surface 41 that they degrade the structural integrity of the frame 16.

Although the pressure control grooves 42 are preferred, it is also possible to construct the vessel 12 without the pressure control grooves and still achieve the desired pressurization of the chamber 17. One disadvantage of this embodiment is that the plunger 22 may become misaligned or cocked in the channel 28 during the pressure stroke so that less consistent results are achieved. In embodiments in which the vessel lacks pressure control grooves, the pressure stroke of the plunger 22 begins when the piston 32 enters the channel 28 and establishes a seal with the walls of the channel. In these embodiments, the volume $V_1$ (for use in the equation above) is equal to the volume of the channel 28 between the liquid surface level S and the port 14 where the piston 32 first establishes a seal with the walls of the channel. To ensure the desired pressurization $P_2$ of the chamber 17, one should size the channel 28 and length of the pressure stroke such that the ratio of the volumes $V_1:V_2$ is equal to the ratio of the pressures $P_2:P_1$. As described previously, the minimum length of the pressure stroke is preferably 0.05 inches to minimize the effect of any manufacturing or operational deviations.

Referring again to FIG. 2, the vessel 12 also preferably includes optical windows for in situ optical interrogation of the reaction mixture in the chamber 17. In the preferred embodiment, the optical windows are the side walls 19A, 19B of the rigid frame 16. The side walls 19A, 19B are optically transmissive to permit excitation of the reaction mixture in the chamber 17 through the side wall 19A and detection of light emitted from the chamber 17 through the side wall 19B. Arrows A represent illumination beams entering the chamber 17 through the side wall 19A and arrows B represent emitted light (e.g., fluorescent signals from fluorescent probes labeling target nucleic acid sequences in the reaction mixture) exiting the chamber 17 through the side wall 19B.

The side walls 19A, 19B are preferably angularly offset from each other. It is usually preferred that the walls 19A, 19B are offset from each other by an angle of about 90°. A 90° angle between excitation and detection paths assures that a minimum amount of excitation radiation entering through the wall 19A will exit through wall 19B. In addition, the 90° angle permits a maximum amount of emitted light to be collected through wall 19B. The walls 19A, 19B are preferably joined to each other to form a "V" shaped intersection at the bottom of the chamber 17. Alternatively, the angled walls 19A, 19B need not be directly joined to each other, but may be separated by an intermediary portion, such as another wall or various mechanical or fluidic features which do not interfere with the thermal and optical performance of the vessel. For example, the walls 19A, 19B may meet at a port which leads to another processing area in communication with the chamber 17, such as an integrated capillary electrophoresis area. In the presently preferred embodiment, a locating tab 27 extends from the frame 16 below the intersection of walls 19A, 19B. The locating tab 27 is used to properly position the vessel 12 in a heat-exchanging module described below with reference to FIG. 8.

Optimum optical sensitivity may be attained by maximizing the optical path length of the light beams exciting the labeled analytes in the reaction mixture and the emitted light that is detected, as represented by the equation:

$$I_o/I_i = C*L*A,$$

where $I_o$ is the illumination output of the emitted light in volts, photons or the like, C is the concentration of analyte to be detected, $I_i$ is the input illumination, L is the path length, and A is the intrinsic absorptivity of the dye used to label the target sequence.

Figure 4:
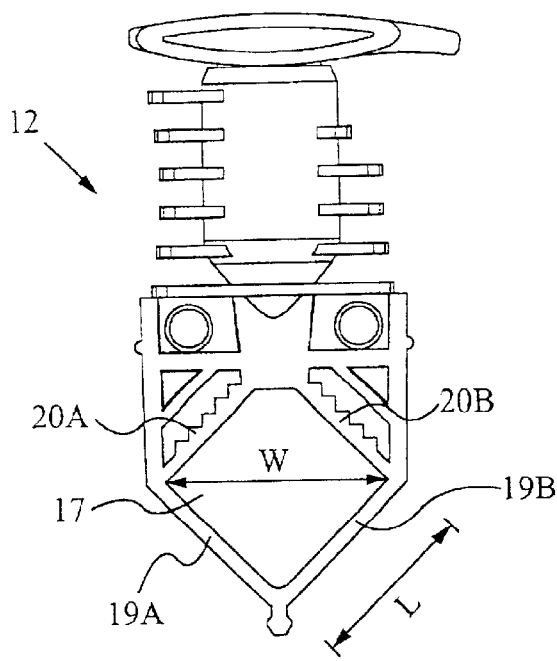
FIG. 4 is another front view of the vessel of FIG. 1.

The thin, flat reaction vessel 12 of the present invention optimizes detection sensitivity by providing maximum optical path length per unit analyte volume. Referring to FIGS. 4–5, the vessel 12 is preferably constructed such that each of the sides walls 19A, 19B, 20A, 20B of the chamber 17 has a length L in the range of 1 to 15 mm, the chamber has a width W in the range of 1.4 to 20 mm, the chamber has a thickness T in the range of 0.5 to 5 mm, and the ratio of the width W of the chamber to the thickness T of the chamber is at least 2:1. These parameters are presently preferred to provide a vessel having a relatively large average optical path length through the chamber, i.e. 1 to 15 mm on average, while still keeping the chamber sufficiently thin to allow for extremely rapid heating and cooling of the reaction mixture contained therein. The average optical path length of the chamber 17 is the distance from the center of the side wall 19A to the center of the chamber 17 plus the distance from the center of the chamber 17 to the center of the side wall 19B. As used herein, the thickness T of the chamber 17 is defined as the thickness of the chamber prior to the outward expansion of the major walls, i.e. the thickness T of the chamber is defined by the thickness of the frame 16.

More preferably, the vessel 12 is constructed such that each of the sides walls 19A, 19B, 20A, 20B of the chamber 17 has a length L in the range of 5 to 12 mm, the chamber has a width W in the range of 7 to 17 mm, the chamber has a thickness T in the range of 0.5 to 2 mm, and the ratio of the width W of the chamber to the thickness T of the chamber is at least 4:1. These ranges are more preferable because they provide a vessel having both a larger average optical path length (i.e., 5 to 12 mm) and a volume capacity in the range of 12 to 100 μl while still maintaining a chamber sufficiently thin to permit extremely rapid heating and cooling of a reaction mixture. The relatively large volume capacity provides for increased sensitivity in the detection of low concentration nucleic acids.

In the preferred embodiment, the reaction vessel 12 has a diamond-shaped chamber 17 defined by the side walls 19A, 19B, 20A, 20B, each of the side walls has a length of about 10 mm, the chamber has a width of about 14 mm, the chamber has a thickness T of 1 mm as defined by the thickness of the frame 16, and the chamber has a volume capacity of about 100 μl. This reaction vessel provides a relatively large average optical path length of 10 mm through the chamber 17. Additionally, the thin chamber allows for extremely rapid heating and/or cooling of the reaction mixture contained therein. The diamond-shape of the chamber 17 helps prevent air bubbles from forming in the chamber as it is filled with the reaction mixture and also aids in optical interrogation of the mixture.

The frame 16 is preferably made of an optically transmissive material, e.g., a polycarbonate or clarified polypropylene, so that the side walls 19A, 19B are optically transmissive. As used herein, the term optically transmissive means that one or more wavelengths of light may be transmitted through the walls. In the preferred embodiment, the optically transmissive walls 19A, 19B are substantially transparent. In addition, one or more optical elements may be present on the optically transmissive side walls 19A, 19B. The optical elements may be designed, for example, to maximize the total volume of solution which is illuminated by a light source, to focus excitation light on a specific region of the chamber 17, or to collect as much fluorescence signal from as large a fraction of the chamber volume as possible. In alternative embodiments, the optical elements may comprise gratings for selecting specific wavelengths, filters for allowing only certain wavelengths to pass, or colored lenses to provide filtering functions. The wall surfaces may be coated or comprise materials such as liquid crystal for augmenting the absorption of certain wavelengths. In the presently preferred embodiment, the optically transmissive walls 19A, 19B are substantially clear, flat windows having a thickness of about 1 mm.

As shown in FIG. 2, the side walls 20A, 20B preferably includes reflective faces 21 which internally reflect light trying to exit the chamber 17 through the side walls 20A, 20B. The reflective faces 21 are arranged such that adjacent faces are angularly offset from each other by about 90°. In addition, the frame 16 defines open spaces between the side walls 20A, 20B and support ribs 15. The open spaces are occupied by ambient air that has a different refractive index than the material composing the frame (e.g., plastic). Due to the difference in the refractive indexes, the reflective faces 21 are effective for internally reflecting light trying to exit the chamber through the walls 20A, 20B and provide for increased detection of optical signal through the walls 19A, 19B. In the preferred embodiment, the optically transmissive side walls 19A, 19B define the bottom portion of the diamond-shaped chamber 17, and the retro-reflective side walls 20A, 20B define the top portion of the chamber.

Figure 3:
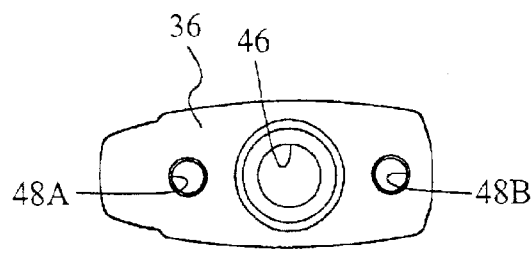
FIG. 3 is a top view of a plunger cap of the vessel of FIG. 1.

The reaction vessel 12 may be used in manual operations performed by human technicians or in automated operations performed by machines, e.g. pick-and-place machines. As shown in FIG. 1, for the manual embodiments, the vessel 12 preferably includes finger grips 26 and a leash 24 that conveniently attaches the plunger 22 to the body of the vessel 12. As shown in FIG. 3, for automated embodiments, the plunger cap 36 preferably includes a tapered engagement aperture 46 for receiving and establishing a fit with a robotic arm or machine tip (not shown in FIG. 3), thus enabling the machine tip to pick and place the plunger in the channel. The engagement aperture 46 preferably has tapered side walls for establishing a friction fit with the machine tip. Alternatively, the engagement aperture may be designed to establish a vacuum fit with the machine tip. The plunger cap 36 may optionally include alignment apertures 48A, 48B used by the machine tip to properly align the plunger cap 36 as the plunger is inserted into the channel.

A preferred method for fabricating the reaction vessel 12 will now be described with reference to FIGS. 1–2. The reaction vessel 12 may be fabricated by first molding the rigid frame 16 using known injection molding techniques. The frame 16 is preferably molded as a single piece of polymeric material, e.g., clarified polypropylene. After the frame 16 is produced, thin, flexible sheets are cut to size and sealed to opposite sides of the frame 16 to form the major walls 18 of the chamber 17.

The major walls 18 are preferably cast or extruded films of polymeric material, e.g., polypropylene films, that are cut to size and attached to the frame 16 using the following procedure. A first piece of film is placed over one side of the bottom portion of the frame 16. The frame 16 preferably includes a tack bar 47 for aligning the top edge of the film. The film is placed over the bottom portion of the frame 16 such that the top edge of the film is aligned with the tack bar 47 and such that the film completely covers the bottom portion of the frame 16 below the tack bar 47. The film should be larger than the bottom portion of the frame 16 so that it may be easily held and stretched flat across the frame. The film is then cut to size to match the outline of the frame by clamping to the frame the portion of the film that covers the frame and cutting away the portions of the film that extend past the perimeter of the frame using, e.g., a laser or die. The film is then tack welded to the frame, preferably using a laser.

The film is then sealed to the frame 16, preferably by heat sealing. Heat sealing is presently preferred because it produces a strong seal without introducing potential contaminants to the vessel as the use of adhesive or solvent bonding techniques might do. Heat sealing is also simple and inexpensive. At a minimum, the film should be completely sealed to the surfaces of the side walls 19A, 19B, 20A, 20B. More preferably, the film is additionally sealed to the surfaces of the support ribs 15 and tack bar 47. The heat sealing may be performed using, e.g., a heated platen. An identical procedure may be used to cut and seal a second sheet to the opposite side of the frame 16 to complete the chamber 17.

Many variations to this fabrication procedure are possible. For example, in an alternative embodiment, the film is stretched across the bottom portion of the frame 16 and then sealed to the frame prior to cutting the film to size. After sealing the film to the frame, the portions of the film that extend past the perimeter of the frame are cut away using, e.g., a laser or die.

The plunger 22 is also preferably molded from polymeric material, preferably polypropylene, using known injection molding techniques. As shown in FIG. 1, the frame 16, plunger 22, and leash 24 connecting the plunger to the frame may all be formed in the same mold to form a one-piece part. This embodiment of the vessel is especially suitable for manual use in which a human operator fills the vessel and inserts the plunger 22 into the channel 28. The leash 24 ensures that the plunger 22 is not lost or dropped on the floor. Alternatively, as shown in FIG. 2, the plunger 22 may be molded separately from the frame 16 so that the plunger and frame are separate pieces. This embodiment is especially suitable for automated use of the vessel in which the plunger 22 is picked and placed into the channel 28 by an automated machine.

Referring again to FIG. 5, the plates 50A, 50B may be made of various thermally conductive materials including ceramics or metals. Suitable ceramic materials include aluminum nitride, aluminum oxide, beryllium oxide, and silicon nitride. Other materials from which the plates may be made include, e.g., gallium arsenide, silicon, silicon nitride, silicon dioxide, quartz, glass, diamond, polyacrylics, polyamides, polycarbonates, polyesters, polyimides, vinyl polymers, and halogenated vinyl polymers, such as polytetrafluoroethylenes. Other possible plate materials include chrome/aluminum, superalloys, zircaloy, aluminum, steel, gold, silver, copper, tungsten, molybdenum, tantalum, brass, sapphire, or any of the other numerous ceramic, metal, or polymeric materials available in the art.

Ceramic plates are presently preferred because their inside surfaces may be conveniently machined to very high smoothness for high wear resistance, high chemical resistance, and good thermal contact to the flexible walls of the reaction vessel. Ceramic plates can also be made very thin, preferably between about 0.6 and 1.3 mm, for low thermal mass to provide for extremely rapid temperature changes. A plate made from ceramic is also both a good thermal conductor and an electrical insulator, so that the temperature of the plate may be well controlled using a resistive heating element coupled to the plate.

Various thermal elements may be employed to heat and/or cool the plates 50A, 50B and thus control the temperature of the reaction mixture in the chamber 17. In general, suitable heating elements for heating the plate include conductive heaters, convection heaters, or radiation heaters. Examples of conductive heaters include resistive or inductive heating elements coupled to the plates, e.g., resistors or thermoelectric devices. Suitable convection heaters include forced air heaters or fluid heat-exchangers for flowing fluids past the plates. Suitable radiation heaters include infrared or microwave heaters. Similarly, various cooling elements may be used to cool the plates. For example, various convection cooling elements may be employed such as a fan, peltier device, refrigeration device, or jet nozzle for flowing cooling fluids past the surfaces of the plates. Alternatively, various conductive cooling elements may be used, such as a heat sink, e.g. a cooled metal block, in direct contact with the plates.

Figure 6:
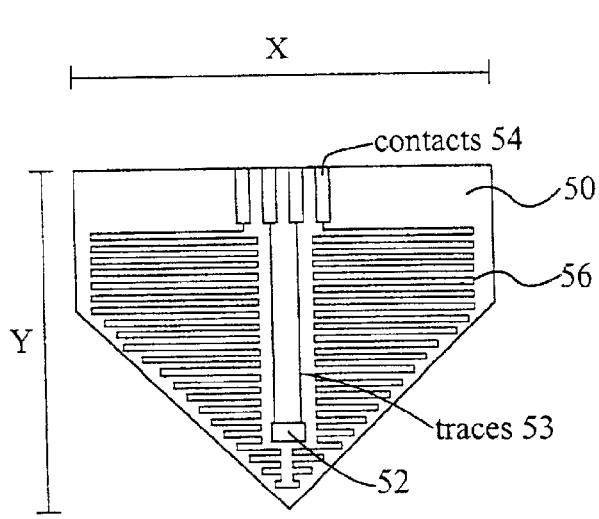
FIG. 6 is a front view of one of the plates of FIG. 5.

Referring to FIG. 6, in the preferred embodiment, each plate 50 has a resistive heating element 56 disposed on its outer surface. The resistive heating element 56 is preferably a thick or thin film and may be directly screen printed onto each plate 50, particularly plates comprising a ceramic material, such as aluminum nitride or aluminum oxide. Screen-printing provides high reliability and low cross-section for efficient transfer of heat into the reaction chamber. Thick or thin film resistors of varying geometric patterns may be deposited on the outer surfaces of the plates to provide more uniform heating, for example by having denser resistors at the extremities and thinner resistors in the middle. Although it is presently preferred to deposit a heating element on the outer surface of each plate, a heating element may alternatively be baked inside of each plate, particularly if the plates are ceramic. The heating element 56 may comprise metals, tungsten, polysilicon, or other materials that heat when a voltage difference is applied across the material.

The heating element 56 has two ends which are connected to respective contacts 54 which are in turn connected to a voltage source (not shown in FIG. 6) to cause a current to flow through the heating element. Each plate 50 also preferably includes a temperature sensor 52, such as a thermocouple, thermistor, or RTD, which is connected by two traces 53 to respective contacts 54. The temperature sensor 52 may be used to monitor the temperature of the plate 50 in a controlled feedback loop.

It is important that the plates have a low thermal mass to enable rapid heating and cooling of the plates. In particular, it is presently preferred that each of the plates has a thermal mass less than about 5 J/° C., more preferably less than 3 J/° C., and most preferably less than 1 J/° C. As used herein, the term thermal mass of a plate is defined as the specific heat of the plate multiplied by the mass of the plate. In addition, each plate should be large enough to cover a respective major wall of the reaction chamber. In the presently preferred embodiment, for example, each of the plates has a width X in the range of 2 to 22 mm, a length Y in the range of 2 to 22 mm, and a thickness in the range of 0.5 to 5 mm. The width X and length Y of each plate is selected to be slightly larger than the width and length of the reaction chamber. Moreover, each plate preferably has an angled bottom portion matching the geometry of the bottom portion of the reaction chamber, as is described below with reference to FIG. 12. Also in the preferred embodiment, each of the plates is made of aluminum nitride having a specific heat of about 0.75 J/g ° C. The mass of each plate is preferably in the range of 0.005 to 5.0 g so that each plate has a thermal mass in the range of 0.00375 to 3.75 J/° C.

Figure 8:
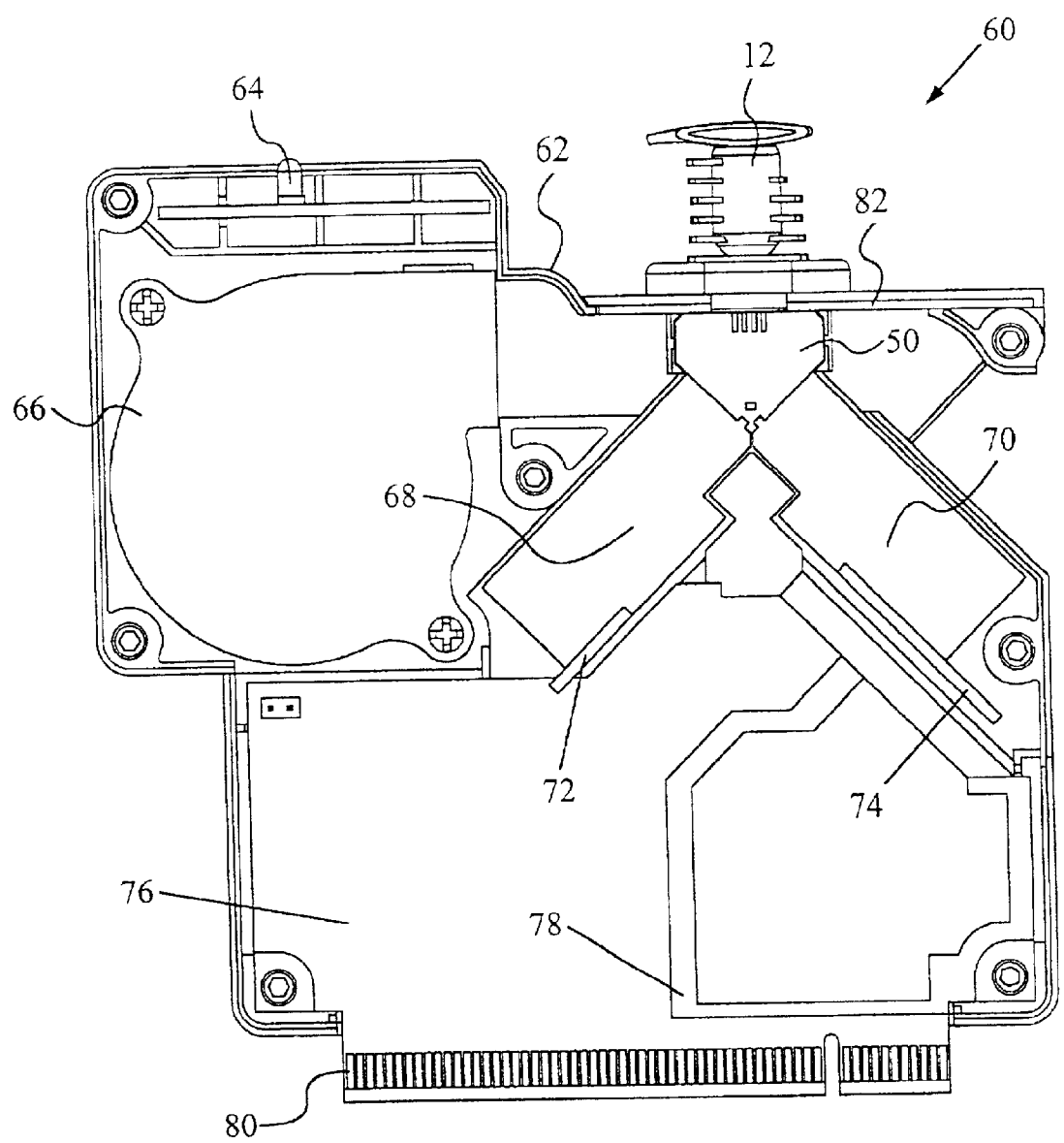
FIG. 8 is a schematic, front view of a heat-exchanging module according to the present invention having a thermal sleeve, a pair of optics assemblies, and a cooling system. The reaction vessel of FIG. 1 is inserted into the thermal sleeve.

FIG. 8 is a schematic side view of a heat-exchanging module 60 into which the reaction vessel 12 is inserted for thermal processing and optical interrogation. The module 60 preferably includes a housing 62 for holding the various components of the module. The module 60 also includes the thermally conductive plates 50 described above. The housing 62 includes a slot (not shown in FIG. 8) above the plates 50 so that the reaction chamber of the vessel 12 may be inserted through the slot and between the plates. The heat-exchanging module 60 also preferably includes a cooling system, such as a fan 66. The fan 66 is positioned to blow cooling air past the surfaces of the plates 50 to cool the plates and hence cool the reaction mixture in the vessel 12. The housing 62 preferably defines channels for directing the cooling air past the plates 50 and out of the module 60.

The heat-exchanging module 60 further includes an optical excitation assembly 68 and an optical detection assembly 70 for optically interrogating the reaction mixture contained in the vessel 12. The excitation assembly 68 includes a first circuit board 72 for holding its electronic components, and the detection assembly 68 includes a second circuit board 74 for holding its electronic components. The excitation assembly 68 includes one or more light sources, such as LEDs, for exciting fluorescent probes in the vessel 12. The excitation assembly 68 also includes one or more lenses for collimating the light from the light sources, as well as filters for selecting the excitation wavelength ranges of interest. The detection assembly 70 includes one or more detectors, such as photodiodes, for detecting the light emitted from the vessel 12. The detection assembly 70 also includes one or more lenses for focusing and collimating the emitted light, as well as filters for selecting the emission wavelength ranges of interest. The specific components of the optics assemblies 68, 70 are described in greater detail below with reference to FIGS. 16–19.

The optics assemblies 68, 70 are positioned in the housing 62 such that when the chamber of the vessel 12 is inserted between the plates 50, the first optics assembly 68 is in optical communication with the chamber 17 through the optically transmissive side wall 19A (see FIG. 2) and the second optics assembly 70 is in optical communication with the chamber through the optically transmissive side wall 19B (FIG. 2). In the preferred embodiment, the optics assemblies 68, 70 are placed into optical communication with the optically transmissive side walls by simply locating the optics assemblies 68, 70 next to the bottom edges of the plates 50 so that when the chamber of the vessel is placed between the plates, the optics assemblies 68, 70 directly contact, or are in close proximity to, the side walls.

Figure 12:
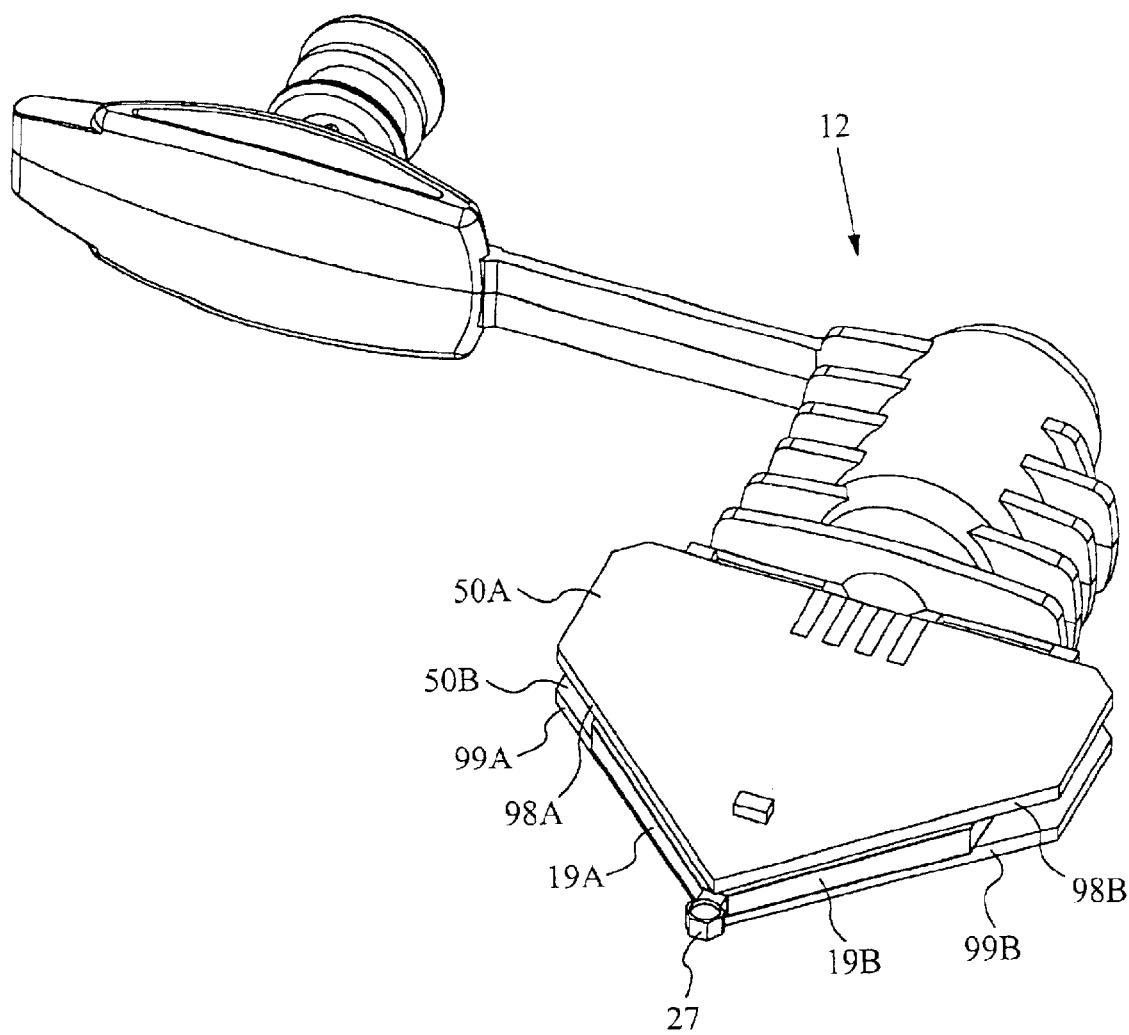
FIG. 12 is an isometric view of the reaction vessel of FIG. 1 inserted between the plates of FIG. 5.

As shown in FIG. 12, the vessel 12 preferably has an angled bottom portion (e.g., triangular) formed by the optically transmissive side walls 19A, 19B. Each of the plates 50A, 50B has a correspondingly shaped bottom portion. The bottom portion of the first plate 50A has a first bottom edge 98A and a second bottom edge 98B. Similarly, the bottom portion of the second plate 50B has a first bottom edge 99A and a second bottom edge 99B. The first and second bottom edges of each plate are preferably angularly offset from each other by the same angle that the side walls 19A, 19B are offset from each other (e.g., 90°). Additionally, the plates 50A, 50B are preferably positioned to receive the chamber of the vessel 12 between them such that the first side wall 19A is positioned substantially adjacent and parallel to each of the first bottom edges 98A, 99A and such that the second side wall 19B is positioned substantially adjacent and parallel to each of the second bottom edges 98B, 99B. This arrangement provides for easy optical access to the optically transmissive side walls 19A, 19B and hence to the chamber of the vessel 12.

The side walls 19A, 19B may be positioned flush with the edges of the plates 50A, 50B, or more preferably, the side walls 19A, 19B may be positioned such that they protrude slightly past the edges of the plates. As is explained below with reference to FIGS. 16–19, each optics assembly preferably includes a lens that physically contacts a respective one of the side walls 19A, 19B. It is preferred that the side walls 19A, 19B protrude slightly (e.g., 0.02 to 0.3 mm) past the edges of the plates 50A, 50B so that the plates do not physically contact and damage the lenses. A gel or fluid may optionally be used to establish or improve optical communication between each optics assembly and the side walls 19A, 19B. The gel or fluid should have a refractive index close to the refractive indexes of the elements that it is coupling.

Referring again to FIG. 8, the optics assemblies 68, 70 are preferably arranged to provide a 90° angle between excitation and detection paths. The 90° angle between excitation and detection paths assures that a minimum amount of excitation radiation entering through the first side wall of the chamber exits through the second side wall. Also, the 90° angle permits a maximum amount of emitted radiation to be collected through the second side wall. In the preferred embodiment, the vessel 12 includes a locating tab 27 (see FIG. 2) that fits into a slot formed between the optics assemblies 68, 70 to ensure proper positioning of the vessel 12 for optical detection. For improved detection, the module 60 also preferably includes a light-tight lid (not shown) that is placed over the top of the vessel 12 and made light-tight tight to the housing 62 after the vessel is inserted between the plates 50.

Although it is presently preferred to locate the optics assemblies 68, 70 next to the bottom edges of the plates 50, many other arrangements are possible. For example, optical communication may be established between the optics assemblies 68, 70 and the walls of the vessel 12 via optical fibers, light pipes, wave guides, or similar devices. One advantage of these devices is that they eliminate the need to locate the optics assemblies 68, 70 physically adjacent to the plates 50. This leaves more room around the plates in which to circulate cooling air or refrigerant, so that cooling may be improved.

The heat-exchanging module 60 also includes a PC board 76 for holding the electronic components of the module and an edge connector 80 for connecting the module 60 to a base instrument, as will be described below with reference to FIG. 22. The heating elements and temperature sensors on the plates 50, as well as the optical boards 72, 74, are connected to the PC board 76 by flex cables (not shown in FIG. 8 for clarity of illustration). The module 60 may also include a grounding trace 78 for shielding the optical detection circuit. The module 60 also preferably includes an indicator, such as an LED 64, for indicating to a user the current status of the module such as "ready to load sample", "ready to load reagent," "heating," "cooling," "finished," or "fault".

The housing 62 may be molded from a rigid, high-performance plastic, or other conventional material. The primary functions of the housing 62 are to provide a frame for holding the plates 50, optics assemblies 68, 70, fan 66, and PC board 76. The housing 62 also preferably provides flow channels and ports for directing cooling air from the fan 66 across the surfaces of the plates 50 and out of the housing. In the preferred embodiment, the housing 62 comprises complementary pieces (only one piece shown in the schematic side view of FIG. 8) that fit together to enclose the components of the module 60 between them.

The opposing plates 50 are positioned to receive the chamber of the vessel 12 between them such that the flexible major walls of the chamber contact and conform to the inner surfaces of the plates. It is presently preferred that the plates 50 be held in an opposing relationship to each other using, e.g., brackets, supports, or retainers. Alternatively, the plates 50 may be spring-biased towards each other as described in International Publication Number WO 98/38487, the disclosure of which is incorporated by reference herein. In another embodiment of the invention, one of the plates is held in a fixed position, and the second plate is spring-biased towards the first plate. If one or more springs are used to bias the plates towards each other, the springs should be sufficiently stiff to ensure that the plates are pressed against the flexible walls of the vessel with sufficient force to cause the walls to conform to the inner surfaces of the plates.

Figure 9:
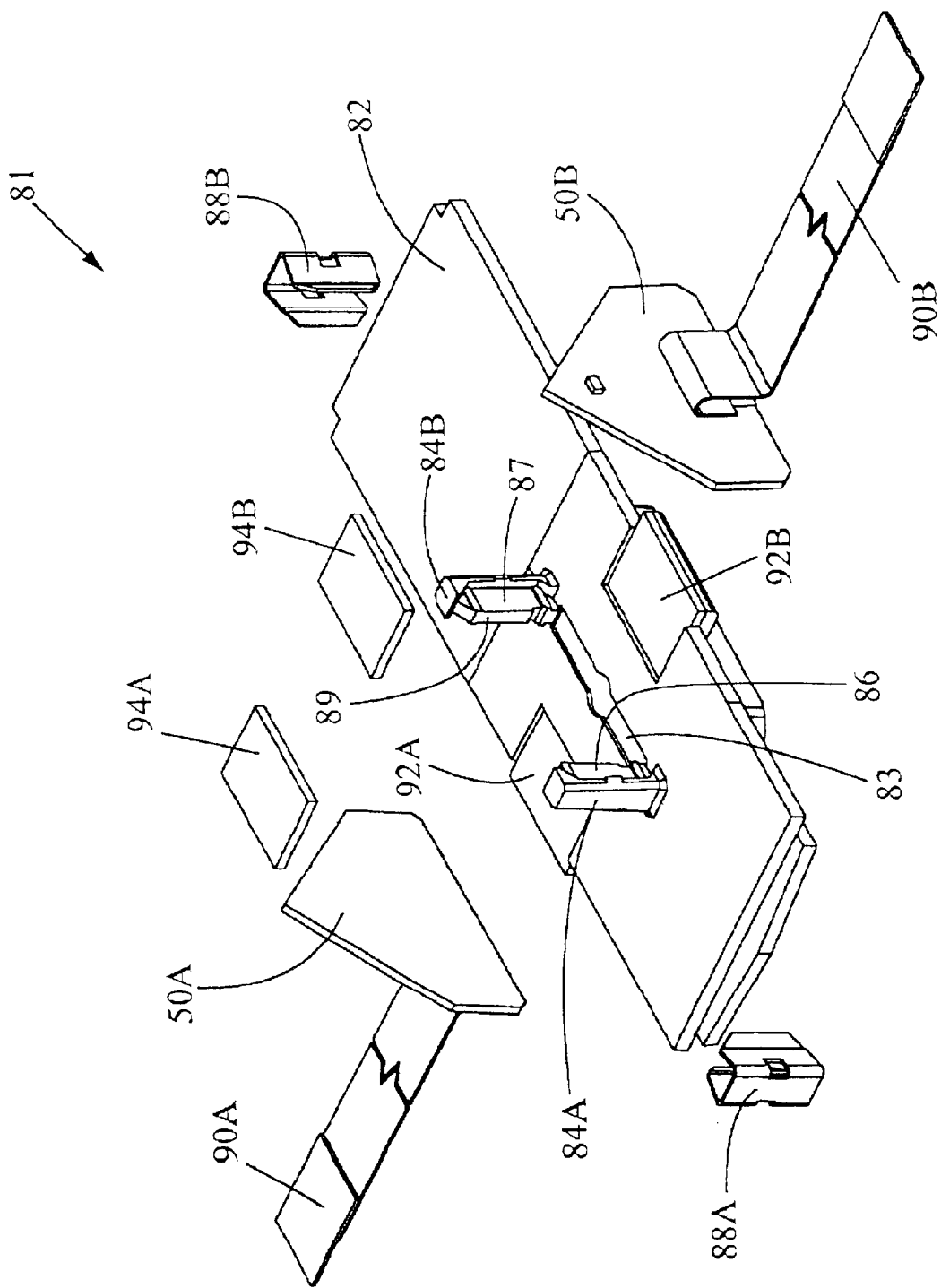
FIG. 9 is an exploded view of a support structure for holding the plates of FIG. 5.
Figure 10:
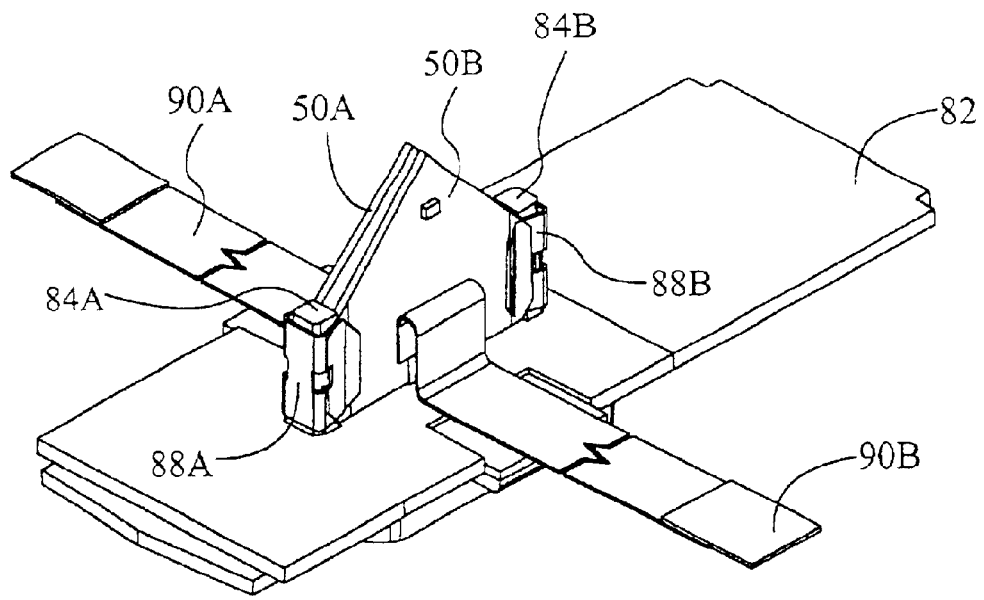
FIGS. 10–11 are assembled views of the support structure of FIG. 9.

FIGS. 9–10 illustrate a preferred support structure 81 for holding the plates 50A, 50B in an opposing relationship to each other. FIG. 9 shows an exploded view of the structure, and FIG. 10 shows an assembled view of the structure. For clarity of illustration, the support structure 81 and plates 50A, 50B are shown upside down relative to their normal orientation in the heat-exchanging module of FIG. 8. Referring to FIG. 9, the support structure 81 includes a mounting plate 82 having a slot 83 formed therein. The slot 83 is sufficiently large to enable the chamber of the vessel to be inserted through it. Spacing posts 84A, 84B extend from the mounting plate 82 on opposite sides of the slot 83. Spacing post 84A has indentations 86 formed on opposite sides thereof (only one side visible in the isometric view of FIG. 9), and spacing post 84B has indentations 87 formed on opposite sides thereof (only one side visible in the isometric view of FIG. 9). The indentations 86, 87 in the spacing posts are for receiving the edges of the plates 50A, 50B. To assemble the structure, the plates 50A, 50B are placed against opposite sides of the spacing posts 84A, 84B such that the edges of the plates are positioned in the indentations 86, 87. The edges of the plates are then held in the indentations using a suitable retention means. In the preferred embodiment, the plates are retained by retention clips 88A, 88B. Alternatively, the plates 50A, 50B may be retained by adhesive bonds, screws, bolts, clamps, or any other suitable means.

The mounting plate 82 and spacing posts 84A, 84B are preferably integrally formed as a single molded piece of plastic. The plastic should be a high temperature plastic, such as polyetherimide, which will not deform of melt when the plates 50A, 50B are heated. The retention clips 84A, 84B are preferably stainless steel. The mounting plate 82 may optionally include indentations 92A, 92B for receiving flex cables 90A, 90B, respectively, that connect the heating elements and temperature sensors disposed on the plates 50A, 50B to the PC board 76 of the heat-exchanging module 60 (FIG. 8). The portion of the flex cables 90A adjacent the plate 50A is held in the indentation 92A by a piece of tape 94A, and the portion of the flex cables 90B adjacent the plate 50B is held in the indentation 92B by a piece of tape 94B.

Figure 11:
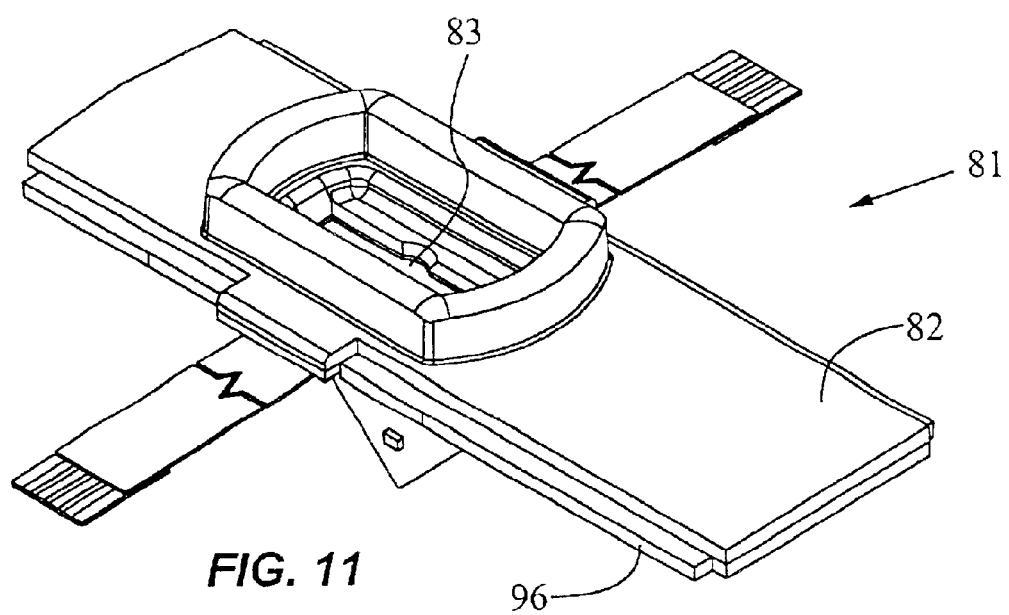

FIG. 11 is an isometric view of the assembled support structure 81. The mounting plate 82 preferably includes tabs 96 extending from opposite sides thereof for securing the structure 81 to the housing of the heat-exchanging module. Referring again to FIG. 8, the housing 62 preferably includes slots for receiving the tabs to hold the mounting plate 82 securely in place. Alternatively, the mounting plate 82 may be attached to the housing 62 using, e.g., adhesive bonding, screws, bolts, clamps, or any other conventional means of attachment.

Referring again to FIG. 9, the support structure 81 preferably holds the plates 50A, 50B so that their inner surfaces are angled very slightly towards each other. In the preferred embodiment, each of the spacing posts 84A, 84B has a wall 89 that is slightly tapered so that when the plates 50A, 50B are pressed against opposite sides of the wall, the inner surfaces of the plates are angled slightly towards each other.

As best shown in FIG. 5, the inner surfaces of the plates 50A, 50B angle towards each other to form a slightly V-shaped slot into which the chamber 17 is inserted. The amount by which the inner surfaces are angled towards each other is very slight, preferably about 1° from parallel. The surfaces are angled towards each other so that, prior to the insertion of the chamber 17 between the plates 50A, 50B, the bottoms of the plates are slightly closer to each other than the tops. This slight angling of the inner surfaces enables the chamber 17 of the vessel to be inserted between the plates and withdrawn from the plates more easily. Alternatively, the inner surfaces of the plates 50A, 50B could be held parallel to each other, but insertion and removal of the vessel 12 would be more difficult.

In addition, the inner surfaces of the plates 50A, 50B are preferably spaced from each other a distance equal to the thickness of the frame 16. In embodiments in which the inner surfaces are angled towards each other, the centers of the inner surfaces are preferably spaced a distance equal to the thickness of the frame 16 and the bottoms of the plates are initially spaced a distance that is slightly less than the thickness of the frame 16. When the chamber 17 is inserted between the plates 50A, 50B, the rigid frame 16 forces the bottom portions of the plates apart so that the chamber 17 is firmly sandwiched between the plates. The distance that the plates 50A, 50B are wedged apart by the frame 16 is usually very small, e.g., about 0.035 mm if the thickness of the frame is 1 mm and the inner surfaces are angled towards each other by 1°.

Referring again to FIG. 10, the retention clips 88A, 88B should be sufficiently flexible to accommodate this slight outward movement of the plates 50A, 50B, yet sufficiently stiff to hold the plates within the recesses in the spacing posts 84A, 84B during insertion and removal of the vessel. The wedging of the vessel between the plates 50A, 50B provides an initial preload against the chamber and ensures that the flexible major walls of the chamber, when pressurized, establish good thermal contact with the inner surfaces of the plates.

Figure 13:
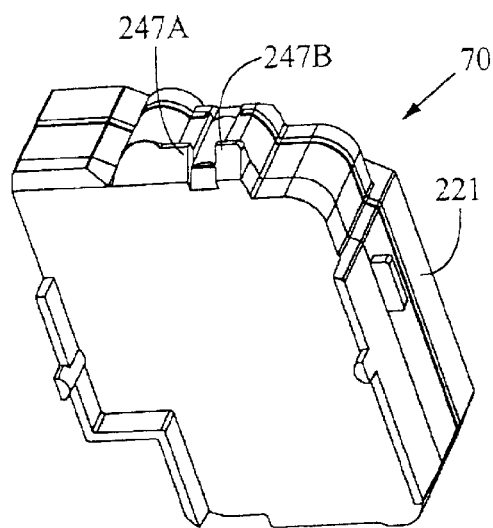
FIG. 13 is an isometric view showing the exterior of one the optics assemblies of FIG. 8.
Figure 14:
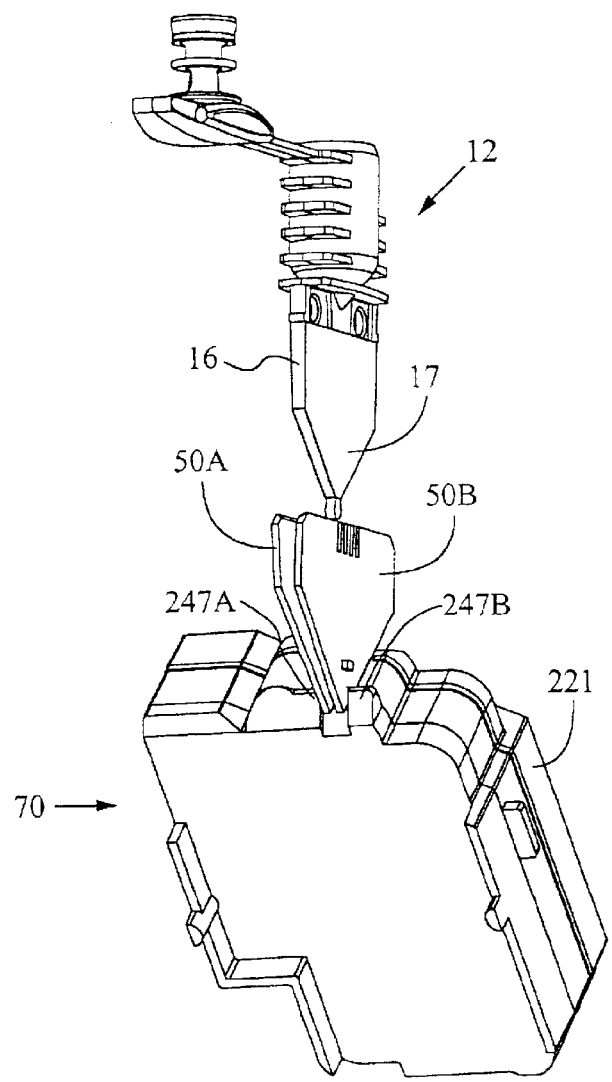
FIG. 14 is an isometric view of the optics assembly of FIG. 13, the plates of FIG. 5 in contact with the optics assembly, and the vessel of FIG. 1 positioned above the plates.

Referring again to FIG. 8, to limit the amount that the plates 50 can spread apart due to the pressurization of the vessel 12, stops may be molded into the housings of optics assemblies 68, 70. As shown in FIG. 13, the housing 221 of the optics assembly 70 includes claw-like stops 247A, 247B that extend outwardly from the housing. As shown in FIG. 14, the housing 221 is positioned such that the bottom edges of the plates 50A, 50B are inserted between the stops 247A, 247B. The stops 247A, 247B thus prevent the plates 50A, 50B from spreading farther than a predetermined maximum distance from each other. Although not shown in FIG. 14 for illustrative clarity, the optics assembly 68 (see FIG. 8) has a housing with corresponding stops for preventing the other halves of the plates from spreading farther than the predetermined maximum distance from each other. Referring again to FIG. 14, the maximum distance that stops 247A, 247B permit the inner surfaces of the plates 50A, 50B to be spaced from each other should closely match the thickness of the frame 16. Preferably, the maximum spacing of the inner surfaces of the plates 50A, 50B is slightly larger than the thickness of the frame 16 to accommodate tolerance variations in the vessel 12 and plates 50A, 50B. For example, the maximum spacing is preferably about 0.1 to 0.3 mm greater than the thickness of the frame 16.

Referring again to FIG. 8, the module 60 includes one or more detection mechanisms for detecting and measuring a signal related to the quantity of a target nucleic acid sequence in the vessel 12. Preferably, the sample in the vessel 12 contains a fluorescent indicator, and the signal is a fluorescent signal whose intensity is proportional to the quantity of the target nucleic acid sequence in the vessel 12. Although fluorescent signals are presently preferred, it is to be understood that other types of signals are known and may be used in the practice of the present invention. To illustrate, indicators of nucleic acid concentration may be provided by labels that produce signals detectable by fluorescence, radioactivity, colorimetry, X-ray diffraction or absorption, magnetism, or enzymatic activity. Suitable labels include, for example, fluorophores, chromophores, radioactive isotopes, electron-dense reagents, enzymes, and ligands having specific binding partners (e.g., biotin-avidin). Electrical signals may also be used to detect the presence of a target nucleic acid sequence. For example, measurements of electrical conductance, inductance, resistance, or capacitance may be used to indicate the quantity of the target nucleic acid sequence in the sample.

Labeling of nucleic acid sequences may be achieved by a number of means, including by chemical modification of a nucleic acid primer or probe. Suitable fluorescent labels may include non-covalently binding labels (e.g., intercalating dyes) such as ethidium bromide, propidium bromide, chromomycin, acridine orange, and the like. However, in the practice of the present invention the use of covalently-binding fluorescent agents is preferred. Such covalently-binding fluorescent labels include fluorescein and derivatives thereof such as FAM, HEX, TET and JOE (all of which can be obtained from PE Biosystems, Foster City, California); rhodamine and derivatives such as Texas Red (Molecular Probes, Eugene, Oreg.); ROX and TAMRA (PE Biosystems, Foster City, Calif.); Lucifer Yellow; coumarin derivatives and the like. Another preferred indicator of nucleic acid concentration is fluorescence energy-transfer (FET), in which a fluorescent reporter (or "donor") label and a quencher (or "acceptor") label are used in tandem to produce a detectable signal that is proportional to the amount of amplified nucleic acid product (e.g., in the form of double-stranded nucleic acid) present in the reaction mixture. Yet another detection method useful in the practice of the present invention is fluorescence polarization (FP) detection of nucleic acid amplification. Further, although fluorescence excitation and emission detection is a preferred embodiment, optical detection methods such as those used in direct absorption and/or transmission with on-axis geometries are also within the scope of the present invention. The quantity of a target nucleic acid sequence may also be measured using time decay fluorescence. Additionally, the concentration of a target nucleic acid sequence may be indicated by phosphorescent signals, chemiluminescent signals, or electrochemiluminescent signals.

Figure 15A:
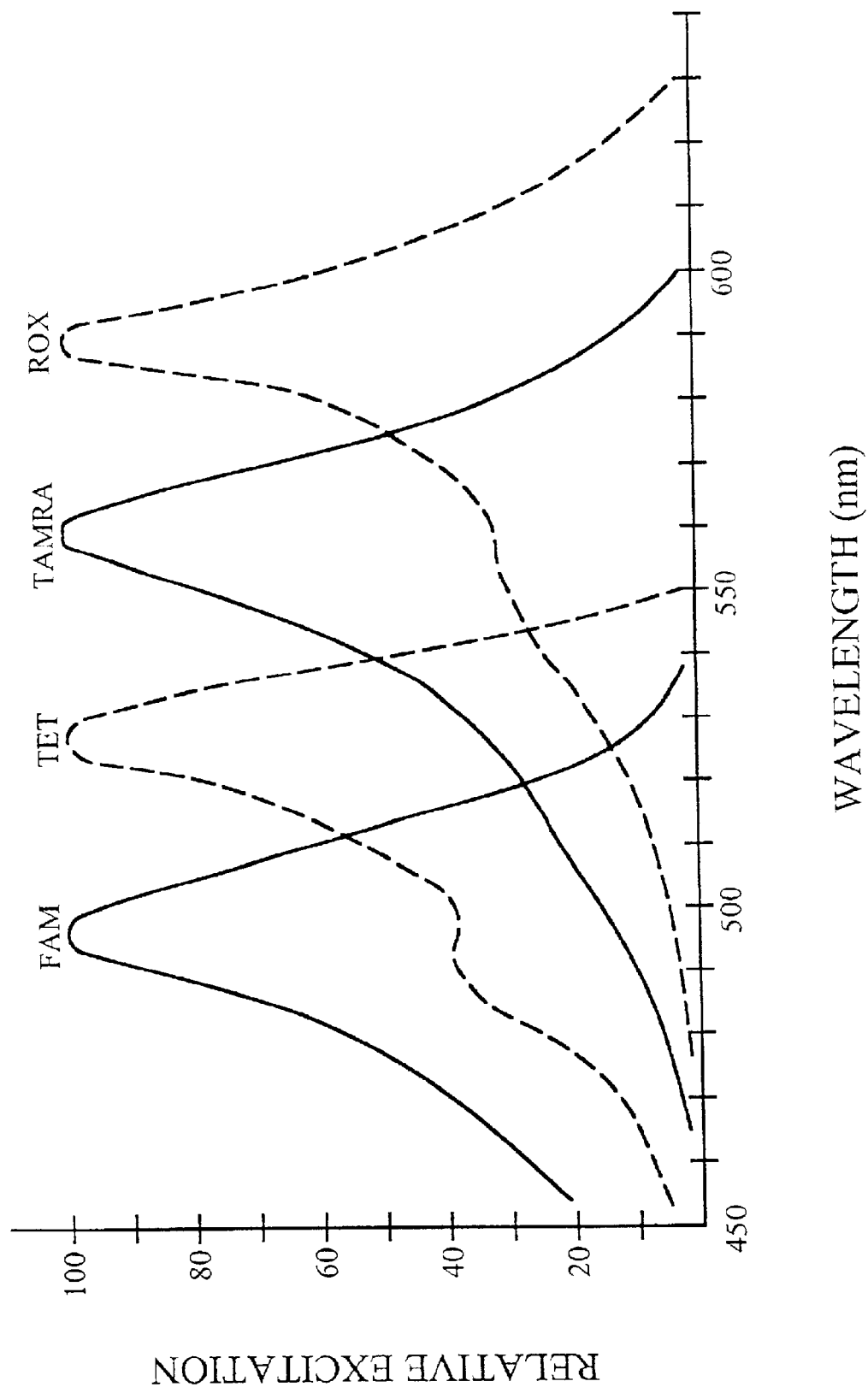
FIGS. 15A and 15B are graphs showing the excitation and emission spectra, respectively, of four dyes often used to label nucleic acid sequences.
Figure 15B:
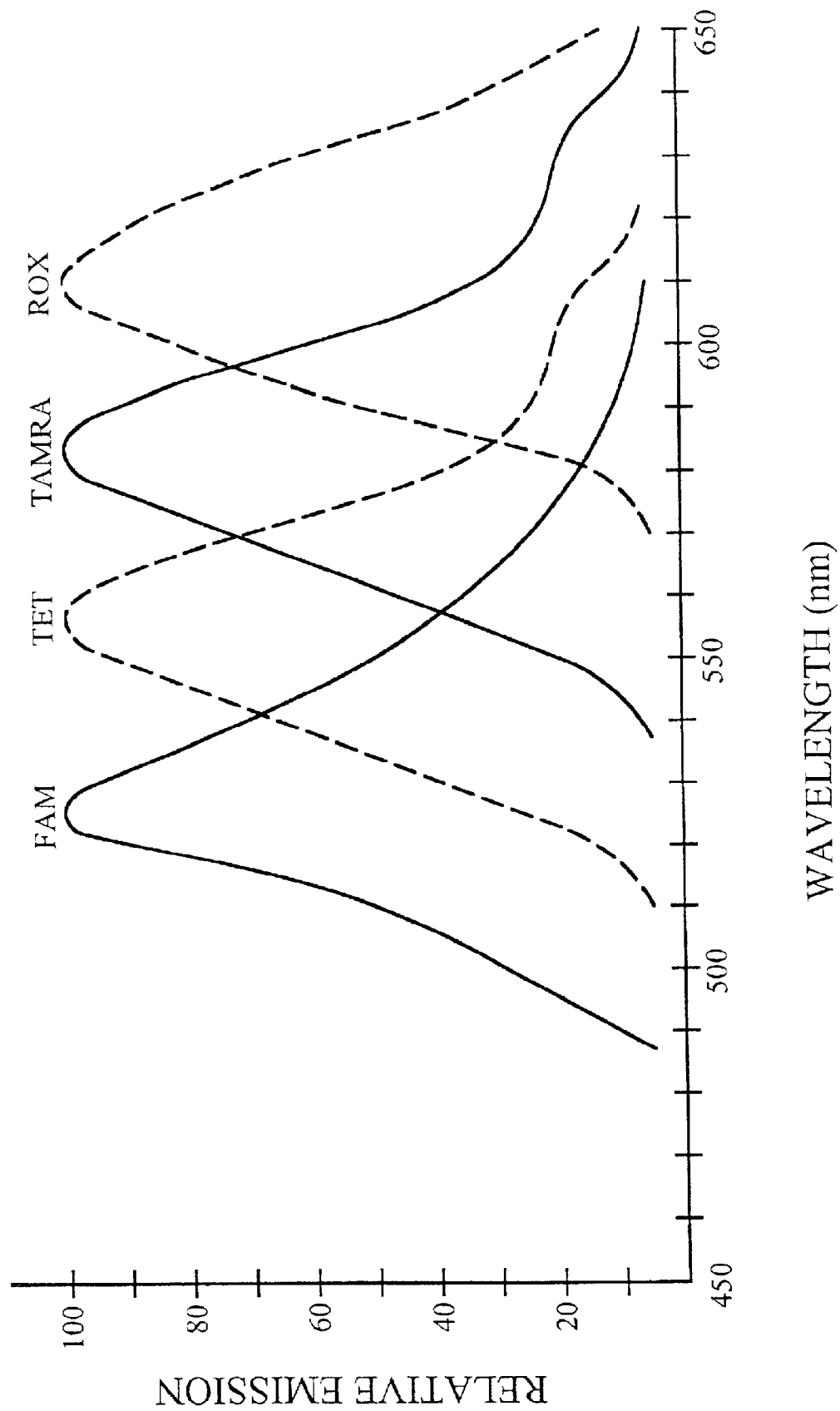

FIGS. 15A and 15B show the fluorescent excitation and emission spectra, respectively, of four fluorescent dyes (FAM, TET, TAMRA, and ROX) commonly used to label target nucleic acid sequences. As shown in FIG. 15A, the excitation spectra curves for FAM, TET, TAMRA, and ROX are typically very broad at the base, but sharper at the peaks. As shown in FIG. 15B, the relative emission spectra curves for the same dyes are also very broad at the base and sharper at the peaks. Thus, these dyes have strongly overlapping characteristics in both their excitation and emission spectra. The overlapping characteristics have traditionally made it difficult to distinguish the fluorescent signal of one dye from another when multiple dyes are used to label different nucleic acid sequences in a reaction mixture.

Figure 15C:
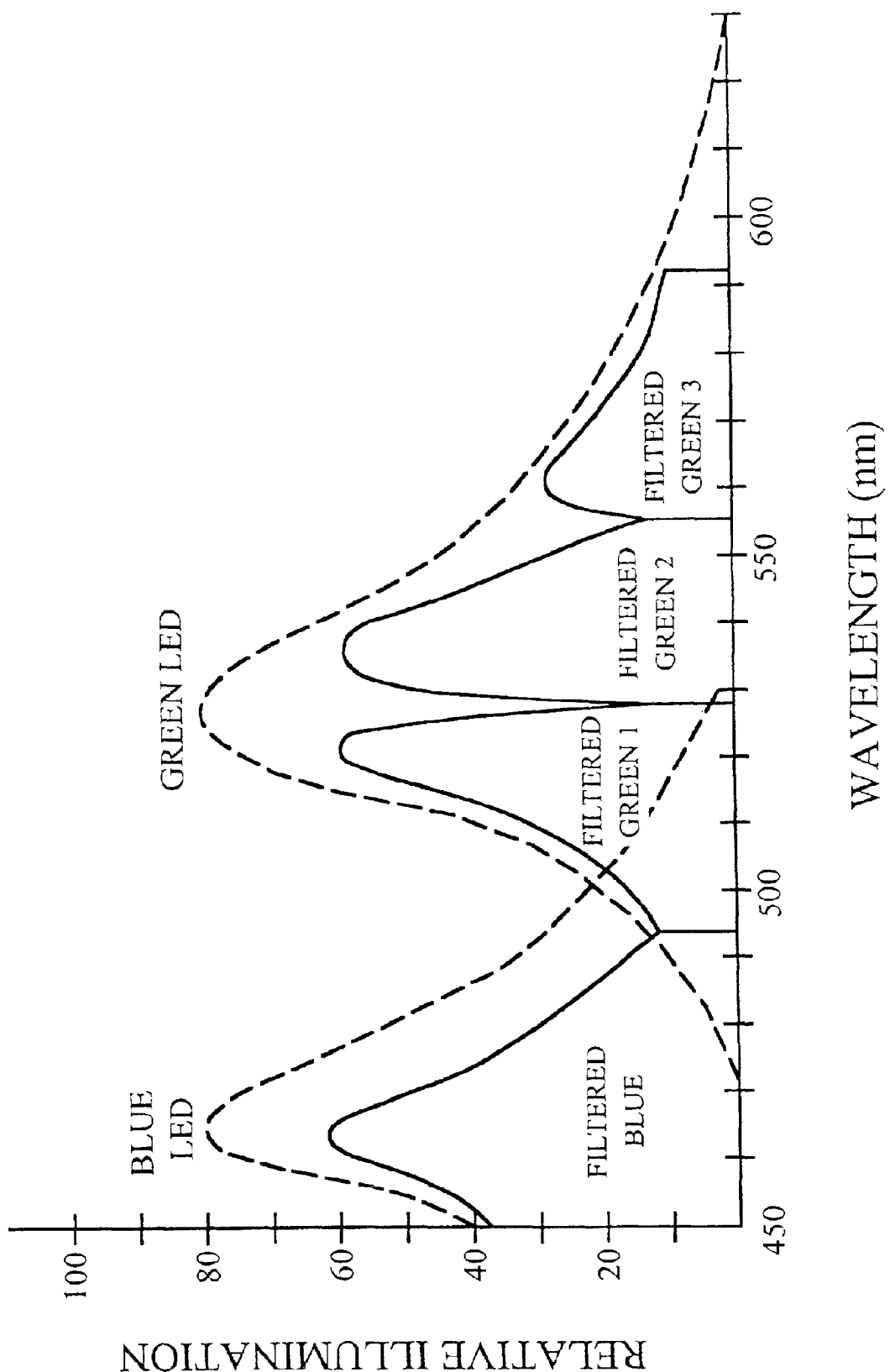
FIG. 15C shows the effects of filtering the outputs of green and blue LEDs to provide distinct excitation wavelength ranges.

According to the present invention, multiple light sources are used to provide excitation beams to the dyes in multiple excitation wavelength ranges. Each light source provides excitation light in a wavelength range matched to the peak excitation range of a respective one of the dyes. In the preferred embodiment, the light sources are blue and green LEDs. FIG. 15C shows the effects of filtering the outputs of blue and green LEDs to provide substantially distinct excitation wavelength ranges. Typical blue and green LEDs have substantial overlap in the range of around 480 nm through 530 nm. By the filtering regime of the present invention, the blue LED light is filtered to a range of about 450 to 495 nm to match the relative excitation peak for FAM. The green LED light is filtered to a first range of 495 to 527 nm corresponding to the excitation peak for TET, a second range of 527 to 555 nm corresponding to the excitation peak for TAMRA, and a third range of 555 to 593 nm corresponding to the excitation peak for ROX.

Figure 15D:
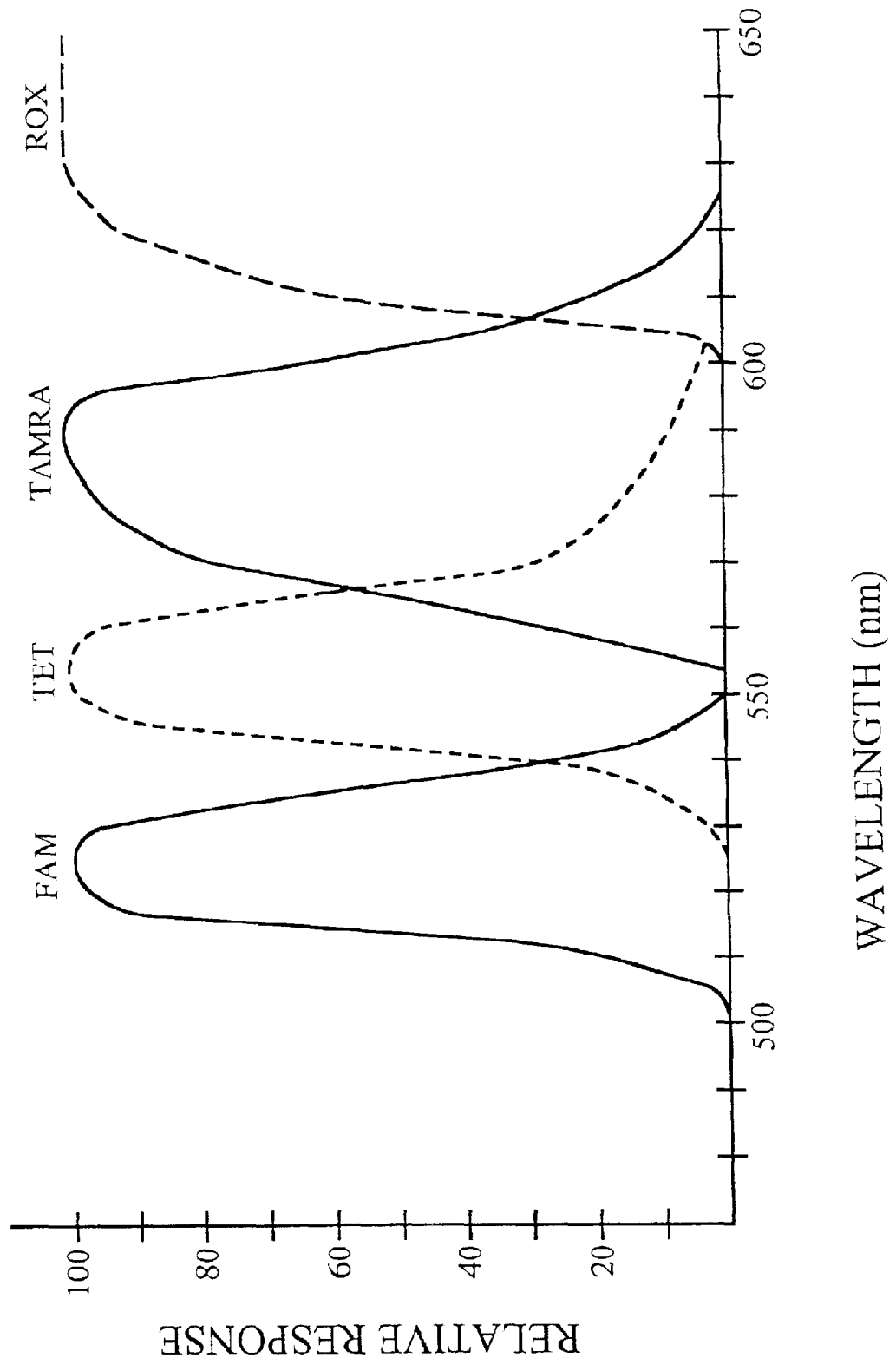
FIG. 15D shows the effects of filtering light emitted from each of the four dyes of FIG. 15B to form distinct emission wavelength ranges.

FIG. 15D shows the effects of filtering light emitted (fluorescent emission) from each of the four dyes to form distinct emission wavelength ranges. As shown previously in FIG. 15B, the fluorescent emissions of the dyes before filtering are spherically diffuse with overlapping spectral bandwidths, making it difficult to distinguish the fluorescent output of one dye from another. As shown in FIG. 15D, by filtering the fluorescent emissions of the dyes into substantially distinct wavelength ranges, a series of relatively narrow peaks (detection windows) are obtained, making it possible to distinguish the fluorescent outputs of different dyes, thus enabling the detection of a number of different fluorescently-labeled nucleic acid sequences in a reaction mixture.

Figure 16:
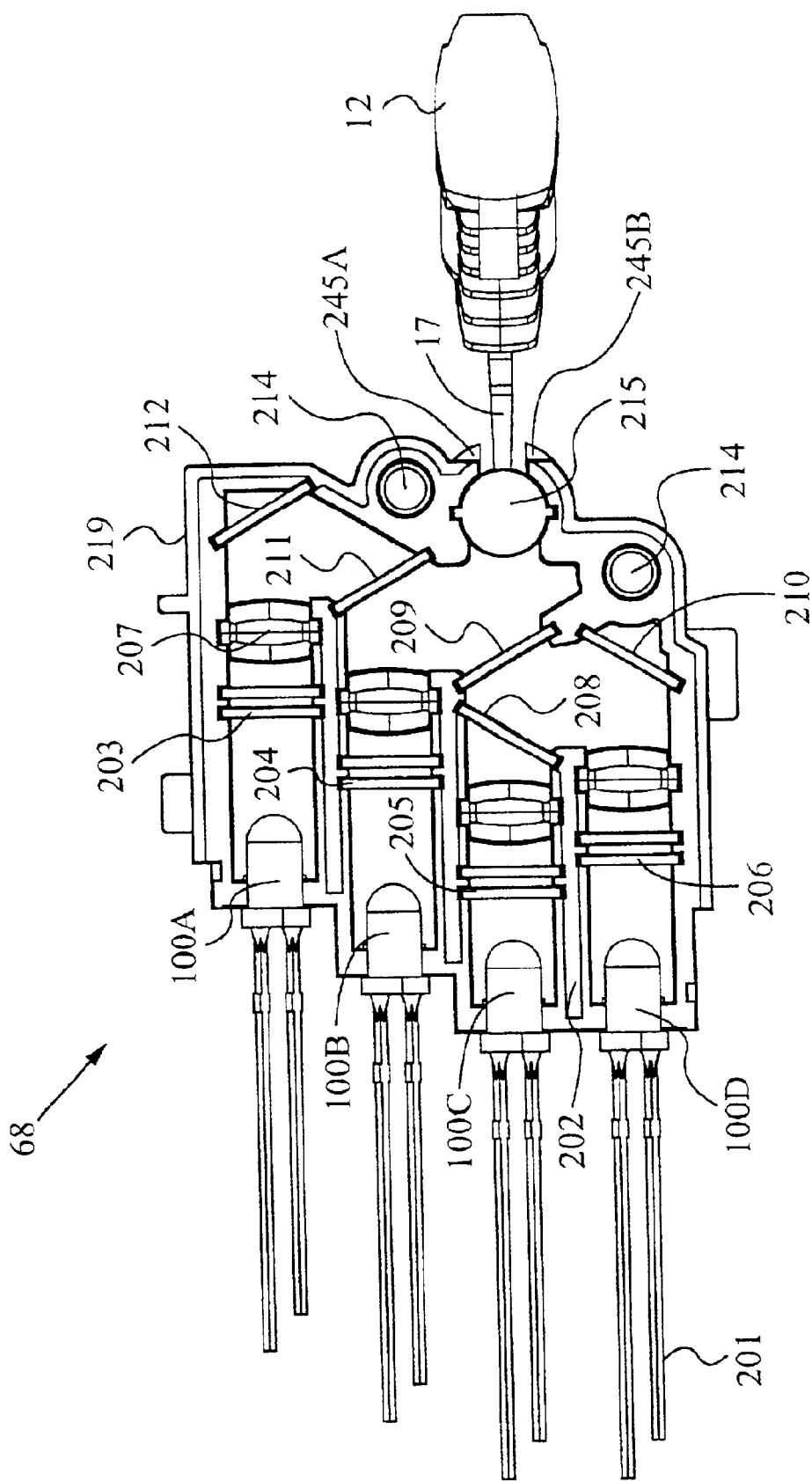
FIG. 16 is a plan view of an optical excitation assembly of the module of FIG. 8.
Figure 17:
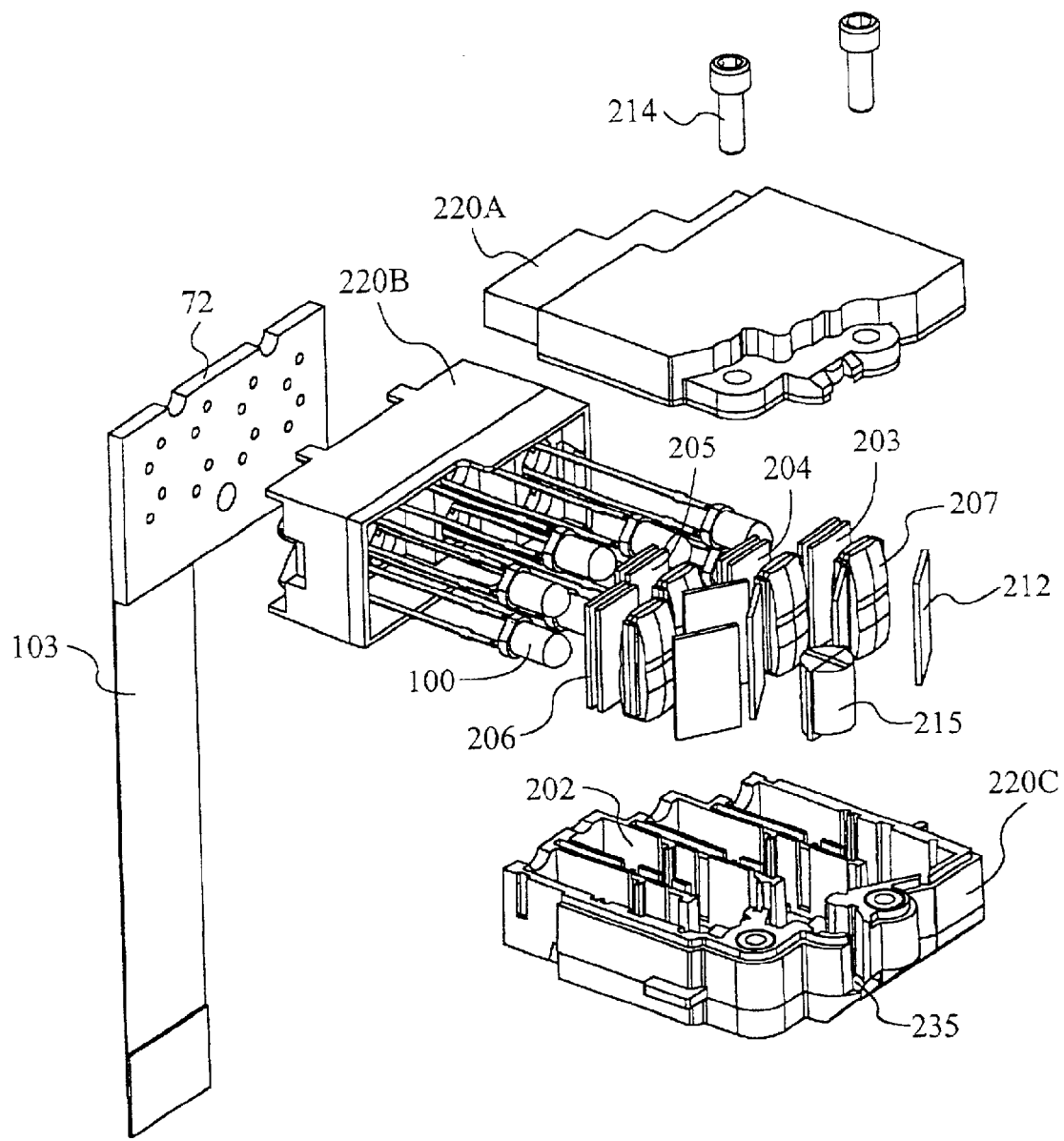
FIG. 17 is an exploded view of the excitation assembly of FIG. 16.

FIG. 16 is a schematic, plan view of the optical excitation assembly 68. The assembly 68 is positioned adjacent the reaction vessel 12 to transmit excitation beams to the reaction mixture contained in the chamber 17. FIG. 17 is an exploded view of the excitation assembly. As shown in FIGS. 16–17, the excitation assembly 68 includes a housing 219 for holding various components of the assembly. The housing 219 includes stops 245A, 245B for limiting the maximum spacing of the thermal plates, as previously discussed with reference to FIGS. 8 and 14. The housing 219 preferably comprises one or more molded pieces of plastic. In the preferred embodiment, the housing 219 is a multi-part housing comprised of three housing elements 220A, 220B, and 220C. The upper and lower housing elements 220A and 220C are preferably complementary pieces that couple together and snap-fit into housing element 220B. In this embodiment, the housing elements 220A and 220C are held together by screws 214. In alternative embodiments, the entire housing 219 may be a one-piece housing that holds a slide-in optics package.

The lower housing element 220C includes an optical window 235 into which is placed a cylindrical rod lens 215 for focusing excitation beams into the chamber 17. In general, the optical window 235 may simply comprise an opening in the housing through which excitation beams may be transmitted to the chamber 17. The optical window may optionally include an optically transmissive or transparent piece of glass or plastic serving as a window pane, or as in the preferred embodiment, a lens for focusing excitation beams. The lens 215 preferably directly contacts one of the optically transmissive side walls of the chamber 17.

The optics assembly 68 also includes four light sources, preferably LEDs 100A, 100B, 100C, and 100D, for transmitting excitation beams through the lens 215 to the reaction mixture contained in the chamber 17. In general, each light source may comprise a laser, a light bulb, or an LED. In the preferred embodiment, each light source comprises a pair of directional LEDs. In particular, the four light sources shown in FIGS. 16–17 are preferably a first pair of green LEDs 100A, a second pair of green LEDs 100B, a pair of blue LEDs 100C, and a third pair of green LEDs 100D. The LEDs receive power through leads 201 which are connected to a power source (not shown in FIGS. 16–17). The LEDs are mounted to the optical circuit board 72 which is attached to the back of the housing element 220B so that the LEDs are rigidly fixed in the housing. The optical circuit board 72 is connected to the main PC board of the heat-exchanging module (shown in FIG. 8) via the flex cable 103.

The optics assembly 68 further includes a set of filters and lenses arranged in the housing 219 for filtering the excitation beams generated by the LEDs so that each of the beams transmitted to the chamber 17 has a distinct excitation wavelength range. As shown in FIG. 17, the lower housing element 220C preferably includes walls 202 that create separate excitation channels in the housing to reduce potential cross-talk between the different pairs of LEDs. The walls 202 preferably include slots for receiving and rigidly holding the filters and lenses. The filters and lenses may also be fixed in the housing by means of an adhesive used alone, or more preferably, with an adhesive used in combination with slots in the housing.

Referring to FIG. 16, the filters in the optics assembly 68 may be selected to provide excitation beams to the reaction mixture in the chamber 17 in any desired excitation wavelength ranges. The optics assembly 68 may therefore be used with any fluorescent, phosphorescent, chemiluminescent, or electrochemiluminescent labels of interest. For purposes of illustration, one specific embodiment of the assembly 68 will now be described in which the assembly is designed to provide excitation beams corresponding to the peak excitation wavelength ranges FAM, TAMRA, TET, and ROX.

In this embodiment, a pair of 593 nm low pass filters 203 are positioned in front of green LEDs 100A, a pair of 555 nm low pass filters 204 are positioned in front of green LEDs 100B, a pair of 495 nm low pass filters 205 are positioned in front of blue LEDs 100C, and a pair of 527 nm low pass filters 206 are positioned in front of green LEDs 100D. Although it is presently preferred to position a pair of low pass filters in front of each pair of LEDs for double filtering of excitation beams, a single filter may be used in alternative embodiments. In addition, a lens 207 is preferably positioned in front of each pair of filters for collimating the filtered excitation beams. The optics assembly 68 also includes a 495 nm high pass reflector 208, a 527 nm high pass reflector 209, a mirror 210, a 555 nm low pass reflector 211, and a 593 nm low pass reflector 212. The reflecting filters and mirrors 208–212 are angularly offset by 30° from the low pass filters 203–206.

The excitation assembly 68 transmits excitation beams to the chamber 17 in four distinct excitation wavelength ranges as follows. When the green LEDs 101A are activated, they generate an excitation beam that passes through the pair of 593 nm low pass filters 203 and through the lens 207. The excitation beam then reflects off of the 593 nm low pass reflector 212, passes through the 555 nm low pass reflector 211, reflects off of the 527 nm high pass reflector 209, and passes through the lens 215 into the reaction chamber 17. The excitation beam from the LEDs 101A is thus filtered to a wavelength range of 555 to 593 nm corresponding to the peak excitation range for ROX. When the green LEDs 100B are activated, they generate an excitation beam that passes through the pair of 555 nm low pass filters 204, reflects off of the 555 nm low pass reflector 211, reflects off of the 527 nm high pass reflector 209, and passes through the lens 215 into the reaction chamber 17. The excitation beam from LEDs 100B is thus filtered to a wavelength range of 527 to 555 nm corresponding to the peak excitation range for TAMRA.

When the blue LEDs 100C are activated, they generate an excitation beam that passes through the pair of 495 nm low pass filters 205, through the 495 nm high pass reflector 208, through the 527 nm high pass reflector 209, and through the lens 215 into the reaction chamber 17. The excitation beam from LEDs 100C is thus filtered to a wavelength below 495 nm corresponding to the peak excitation range for FAM. When the green LEDs 100D are activated, they generate an excitation beam that passes through the pair of 527 nm low pass filters 206, reflects off of the mirror 210, reflects off of the 495 nm high pass reflector 208, passes through the 527 nm high pass reflector 209, and passes through the lens 215 into the reaction chamber 17. The excitation beam from LEDs 100D is thus filtered to a wavelength range of 495 to 527 nm corresponding to the peak excitation range for TET. In operation, the LEDs 100A, 100B, 100C, 100D are sequentially activated to excite the different fluorescent labels contained in the chamber 17 with excitation beams in substantially distinct wavelength ranges.

Figure 18:
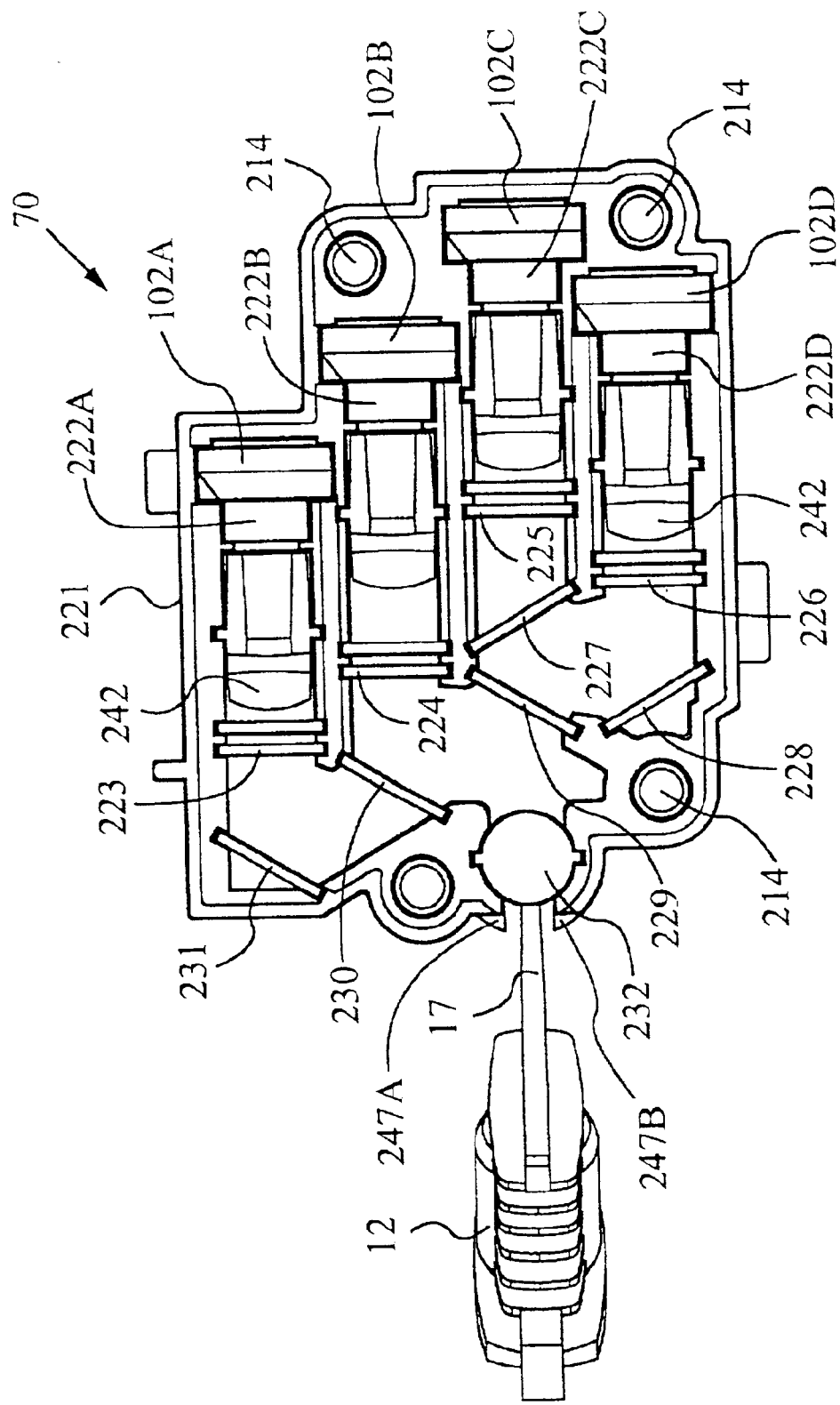
FIG. 18 is a plan view of an optical detection assembly of the module of FIG. 8.
Figure 19:
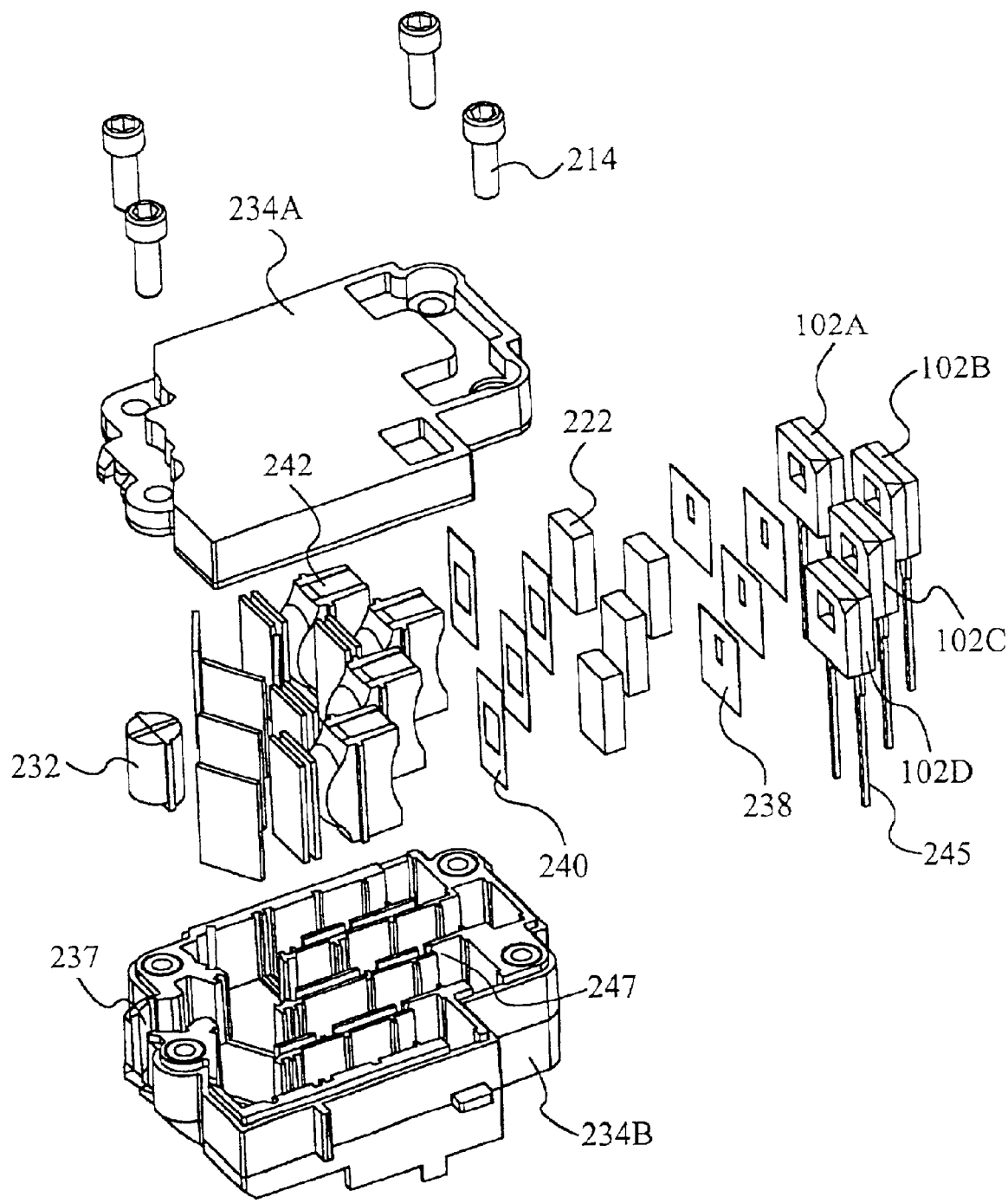
FIG. 19 is an exploded view of the detection assembly of FIG. 18.

FIG. 18 is a schematic, plan view of the optical detection assembly 70. The assembly 70 is positioned adjacent the reaction vessel 12 to receive light emitted from the chamber 17. FIG. 19 is an exploded view of the detection assembly 70. As shown in FIGS. 18–19, the assembly 70 includes a housing 221 for holding various components of the assembly. The housing 221 includes the stops 247A, 247B previously described with reference to FIGS. 13–14. The housing 221 preferably comprises one or more molded plastic pieces. In the preferred embodiment, the housing 221 is a multi-part housing comprised of upper and lower housing elements 234A and 234B. The housing elements 234A, 234B are complementary, mating pieces that are held together by screws 214. In alternative embodiments, the entire housing 221 may be a one-piece housing that holds a slide-in optics package.

The lower housing element 234B includes an optical window 237 into which is placed a cylindrical rod lens 232 for collimating light emitted from the chamber 17. In general, the optical window may simply comprise an opening in the housing through which the emitted light may be received. The optical window may optionally include an optically transmissive or transparent piece of glass or plastic serving as a window pane, or as in the preferred embodiment, the lens 232 for collimating light emitted from the chamber 17. The lens 232 preferably directly contacts one of the optically transmissive side walls of the chamber 17.

The optics assembly 70 also includes four detectors 102A, 102B. 102C, and 102D for detecting light emitted from the chamber 17 that is received through the lens 232. In general, each detector may be a photomultiplier tube, CCD, photodiode, or other known detector. In the preferred embodiment, each detector is a PIN photodiode. The detectors 102A, 102B. 102C, and 102D are preferably rigidly fixed in recesses formed in the lower housing element 234B. The detectors are electrically connected by leads 245 to the optical circuit board 74 (see FIG. 8) which is preferably mounted to the underside of the lower housing element 234B.

The optics assembly 70 further includes a set of filters and lenses arranged in the housing 221 for separating light emitted from the chamber 17 into different emission wavelength ranges and for directing the light in each of the emission wavelength ranges to a respective one of the detectors. As shown in FIG. 19, the lower housing element 234B preferably includes walls 247 that create separate detection channels in the housing, with one of the detectors positioned at the end of each channel. The walls 247 preferably include slots for receiving and rigidly holding the filters and lenses. The filters and lenses may also be rigidly fixed in the housing 221 by an adhesive used alone, or more preferably, with an adhesive used in combination with slots in the housing.

Referring to FIG. 18, the filters in the optics assembly 70 may be selected to block light emitted from the chamber 17 outside of any desired emission wavelength ranges. The optics assembly 70 may therefore be used with any fluorescent, phosphorescent, chemiluminescent, or electrochemiluminescent labels of interest. For purposes of illustration, one specific embodiment of the assembly 70 will now be described in which the assembly is designed to detect light emitted from the chamber 17 in the peak emission wavelength ranges of FAM, TAMRA, TET, and ROX.

In this embodiment, the set of filters preferably includes a 515 nm Schott Glass® filter 222A positioned in front of the first detector 102A, a 550 nm Schott Glass® filter 222B positioned in front of the second detector 102B, a 570 nm Schott Glass® filter 222C positioned in front of the third detector 102C, and a 620 nm Schott Glass® filter 222D positioned in front of the fourth detector 102D. These Schott Glass® filters are commercially available from Schott Glass Technologies, Inc. of Duryea, Pa. The optics assembly 70 also includes a pair of 505 nm high pass filters 223 positioned in front of the first detector 102A, a pair of 537 nm high pass filters 224 positioned in front of the second detector 102B, a pair of 565 nm high pass filters 225 positioned in front of the third detector 102C, and a pair of 605 nm high pass filters 226 positioned in front of the fourth detector 102D.

Although it is presently preferred to position a pair of high pass filters in front of each detector for double filtering of light, a single filter may be used in alternative embodiments. In addition, a lens 242 is preferably positioned in each detection channel between the pair of high pass filters and the Schott Glass® filter for collimating the filtered light. The optics assembly 70 further includes a 605 nm high pass reflector 227, a mirror 228, a 565 nm low pass reflector 229, a 537 nm high pass reflector 230, and a 505 nm high pass reflector 231. The reflecting filters and mirrors 227–231 are preferably angularly offset by 300 from the high pass filters 223–226. As shown in FIG. 19, the detection assembly 70 also preferably includes a first aperture 238 positioned between each detector and Schott Glass® filter 222 and an aperture 240 positioned between each lens 242 and Schott Glass® filter 222. The apertures 238, 240 reduce the amount of stray or off-axis light that reaches the detectors 102A, 102B, 102C, and 102D.

Referring again to FIG. 18, the detection assembly 70 detects light emitted from the chamber 17 in four emission wavelength ranges as follows. The emitted light passes through the lens 232 and strikes the 565 nm low pass reflector 229. The portion of the light having a wavelength in the range of about 505 to 537 nm (corresponding to the peak emission wavelength range of FAM) reflects from the 565 nm low pass reflector 229, passes through the 537 nm high pass reflector 230, reflects from the 505 nm high pass reflector 231, passes through the pair of 505 nm high pass filters 223, through the lens 242, through the 515 nm Schott Glass® filter 222A, and is detected by the first detector 102A. Meanwhile, the portion of the light having a wavelength in the range of about 537 to 565 nm (corresponding to the peak emission wavelength range of TET) reflects from the 565 nm low pass reflector 229, reflects from the 537 nm high pass reflector 230, passes through the pair of 537 nm high pass filters 224, through the lens 242, through the 550 nm Schott Glass® filter 222B, and is detected by the second detector 102B.

Further, the portion of the light having a wavelength in the range of about 565 to 605 nm (corresponding to the peak emission wavelength range of TAMRA) passes through the 565 nm low pass reflector 229, through the 605 nm high pass reflector 227, through the pair of 565 nm high pass filters 225, through the lens 242, through the 570 nm Schott Glass® filter 222C, and is detected by the third detector 102C. The portion of the light having a wavelength over 605 nm (corresponding to the peak emission wavelength range of ROX) passes through the 565 nm low pass reflector 229, reflects from the 605 nm high pass reflector 227, reflects from the mirror 228, passes through the pair of 605 nm high pass filters 226, through the lens 242, through the 620 nm Schott Glass® filter 222D, and is detected by the fourth detector 102D. In operation, the outputs of detectors 102A, 102B, 102C, and 102D are analyzed to determine the starting quantities or concentrations of one or more target nucleic acid sequences in the reaction mixture, as will be described in greater detail below.

FIG. 20 shows a multi-site reactor system 106 according to the present invention. The reactor system 106 comprises a thermal cycler 108 and a controller 112, such as a personal or network computer. The thermal cycler 108 includes a base instrument 110 for receiving multiple heat-exchanging modules 60 (previously described with reference to FIG. 8). The base instrument 110 has a main logic board with edge connectors 114 for establishing electrical connections to the modules 60. The base instrument 110 also preferably includes a fan 116 for cooling its electronic components. The base instrument 110 may be connected to the controller 112 using any suitable data connection, such as a universal serial bus (USB), ethernet connection, or serial line. It is presently preferred to use a USB that connects to the serial port of controller 112. Alternatively, the controller may be built into the base instrument 110.

The term "thermal cycling" is herein intended to mean at least one change of temperature, i.e. increase or decrease of temperature, in a reaction mixture. Therefore, samples undergoing thermal cycling may shift from one temperature to another and then stabilize at that temperature, transition to a second temperature or return to the starting temperature. The temperature cycle may be performed only once or may be repeated as many times as required to study or complete the particular chemical reaction of interest. Due to space limitations in patent drawings, the thermal cycler 108 shown in FIG. 20 includes only sixteen reaction sites provided by the sixteen heat-exchanging modules 60 arranged in two rows of eight modules each. It is to be understood, however, that the thermal cycler can include any number of desired reaction sites, i.e., it can be configured as a multi-hundred site instrument for simultaneously processing hundreds of samples. Alternatively, it may be configured as a small, hand held, battery-operated instrument having, e.g., 1 to 4 reaction sites.

Each of the reaction sites in the thermal cycler 108 is provided by a respective one of the heat-exchanging modules 60. The modules 60 are preferably independently controllable so that different chemical reactions can be run simultaneously in the thermal cycler 108. The thermal cycler 108 is preferably modular so that each heat-exchanging module 60 can be individually removed from the base instrument 110 for servicing, repair, or replacement. This modularity reduces downtime since all the modules 60 are not off line to repair one, and the instrument 110 can be upgraded and enlarged to add more modules as needed. The modularity of the thermal cycler 108 also means that individual modules 60 can be precisely calibrated, and module-specific schedules or corrections can be included in the control programs, e.g., as a series of module-specific calibration or adjustment charts.

Figure 21:
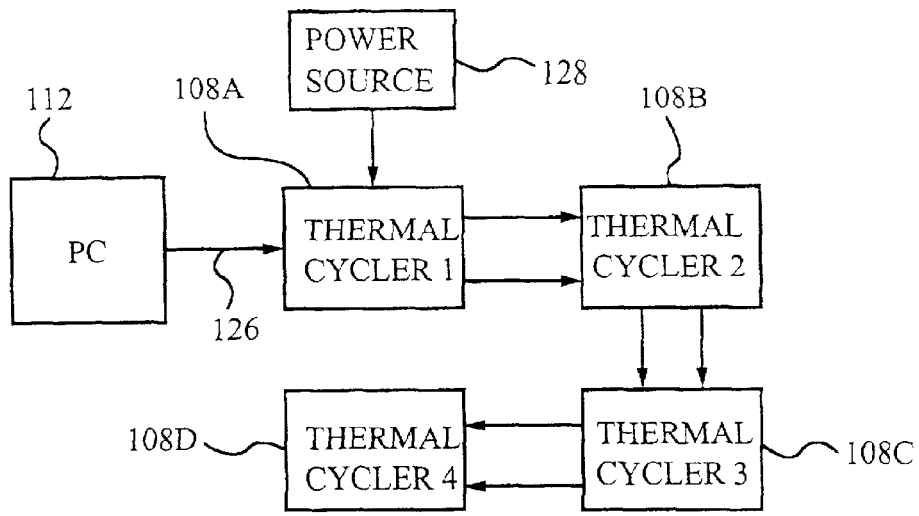
FIG. 21 is a schematic, block diagram of another multi-site reactor system having multiple thermal cycling instruments daisy-chained to a computer and a power source.

In embodiments in which the base instrument 110 operates on external power, e.g. 110 V AC, the instrument preferably includes two power connections 122, 124. Power is received though the first connection 122 and output through the second connection 124. Similarly, the instrument 110 preferably includes network interface inlet and outlet ports 118, 120 for receiving a data connection through inlet port 118 and outputting data to another base instrument through outlet port 120. As shown in the block diagram of FIG. 21, this arrangement permits multiple thermal cyclers 108A, 108B, 108C, 108D to be daisy-chained from one controller 112 and one external power source 128.

Figure 22:
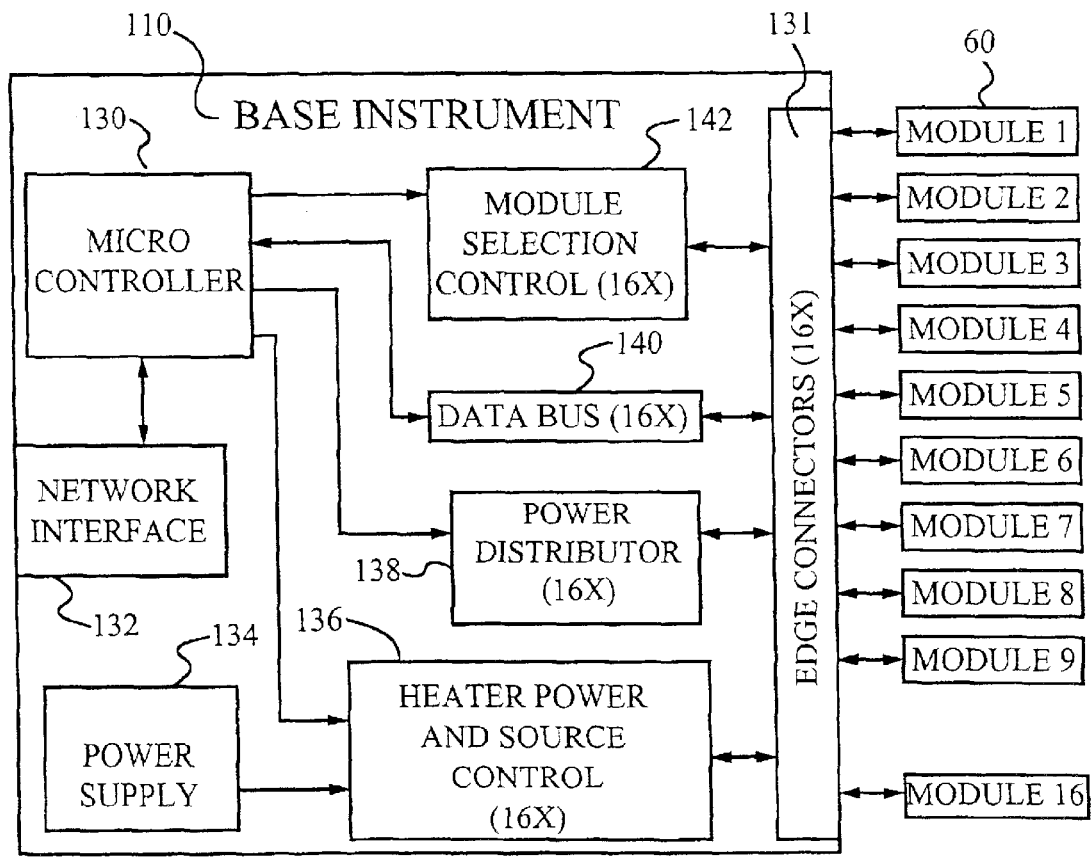
FIG. 22 is a schematic, block diagram of a base instrument of the system of FIG. 20.

FIG. 22 is a schematic, block diagram of the base instrument 110. The base instrument includes a power supply 134 for supplying power to the instrument and to each module 60. The power supply 134 may comprise an AC/DC converter for receiving power from an external source and converting it to direct current, e.g., for receiving 110V AC and converting it to 12V DC. Alternatively, the power supply 134 may comprise a battery, e.g., a 12V battery. The base instrument 110 also includes a microprocessor or microcontroller 130 containing firmware for controlling the operation of the base instrument 110 and modules 60. The microcontroller 130 communicates through a network interface 132 to the controller computer via a USB. Due to current limitations of processing power, it is currently preferred to include at least one microcontroller in the base instrument per sixteen modules 60. Thus if the base instrument has a thirty-two module capacity, at least two microcontrollers should be installed in the instrument 110 to control the modules.

The base instrument 110 further includes a heater power source and control circuit 136, a power distributor 138, a data bus 140, and a module selection control circuit 142. Due to space limitations in patent drawings, control circuit 136, power distributor 138, data bus 140, and control circuit 142 are shown only once in the block diagram of FIG. 22. However, the base instrument 110 actually contains one set of these four functional components 136, 138, 140, 142 for each heat-exchanging module 60. Thus, in the embodiment of FIG. 22, the base instrument 110 includes sixteen control circuits 136, power distributors 138, data buses 140, and control circuits 142. Similarly, the base instrument 110 also includes a different edge connector 131 for connecting to each of the modules 60, so that the instrument includes sixteen edge connectors for the embodiment shown in FIG. 22. The edge connectors are preferably 120 pin card edge connectors that provide cableless connection from the base instrument 110 to each of the modules 60. Each control circuit 136, power distributor 138, data bus 140, and control circuit 142 is connected to a respective one of the edge connectors and to the microcontroller 130.

Each heater power and source control circuit 136 is a power regulator for regulating the amount of power supplied to the heating element(s) of a respective one of the modules 60. The source control circuit 136 is preferably a DC/DC converter that receives a +12V input from the power supply 134 and outputs a variable voltage between 0 and −24V. The voltage is varied in accordance with signals received from the microcontroller 130. Each power distributor 138 provides −5v, +5V, +12V, and GND to a respective module 60. The power distributor thus supplies power for the electronic components of the module. Each data bus 140 provides parallel and serial connections between the microcontroller 130 and the digital devices of a respective one of the modules 60. Each module selection controller 94 allows the microcontroller 130 to address an individual module 60 in order to read or write control or status information.

Figure 23:
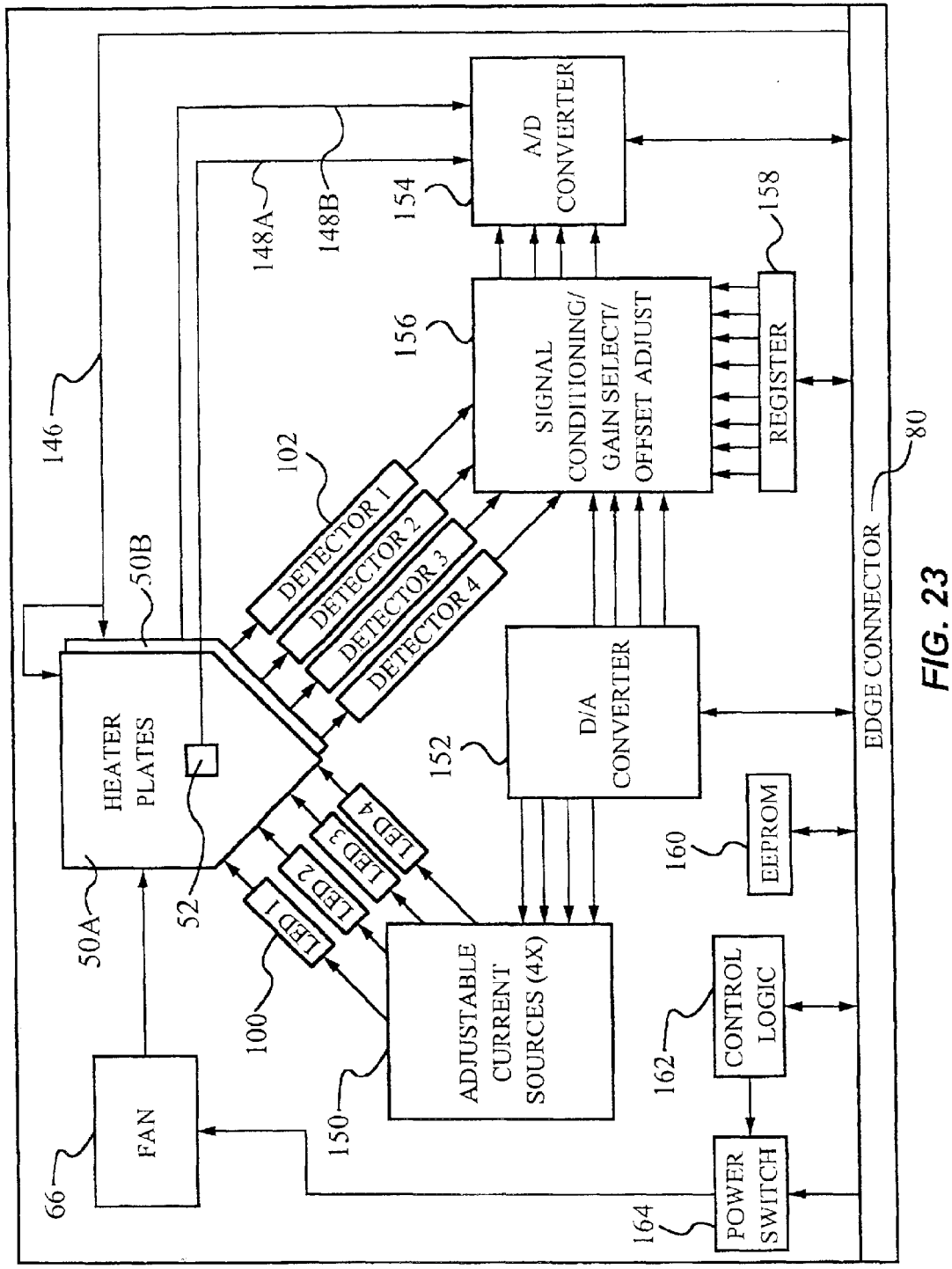
FIG. 23 is a schematic, block diagram of the electronic components of the module of FIG. 8.

FIG. 23 is a schematic, block diagram of the electronic components of a heat-exchanging module 60. Each module includes an edge connector 80 for cableless connection to a corresponding edge connector of the base instrument. The module also includes heater plates 50A, 50B each having a resistive heating element as described above. The plates 50A, 50B are wired in parallel to receive power input 146 from the base instrument. The plates 50A, 50B also include temperature sensors 52, e.g. thermistors, that output analog temperature signals to an analog-to-digital converter 154. The converter 154 converts the analog signals to digital signals and routes them to the microcontroller in the base instrument through the edge connector 80. The heat-exchanging module also includes a cooling system, such as a fan 66, for cooling the plates 50A, 50B. The fan 66 receives power from the base instrument and is activated by switching a power switch 164. The power switch 164 is in turn controlled by a control logic block 162 that receives control signals from the microcontroller in the base instrument.

The module further includes four light sources, such as LEDs 100, for excitation of labeled nucleic acid sequences in the reaction mixture and four detectors 102, preferably photodiodes, for detecting fluorescent signals from the reaction mixture. The module also includes an adjustable current source 150 for supplying a variable amount of current (e.g., in the range of 0 to 30 mA) to each LED to vary the brightness of the LED. A digital-to-analog converter 152 is connected between the adjustable current source 150 and the microcontroller of the base instrument to permit the microcontroller to adjust the current source digitally. The adjustable current source 150 may be used to ensure that each LED has about the same brightness when activated. Due to manufacturing variances, many LEDs have different brightnesses when provided with the same amount of current. The brightness of each LED may be tested during manufacture of the heat-exchanging module and calibration data stored in a memory 160 of the module. The calibration data indicates the correct amount of current to provide to each LED. The microcontroller reads the calibration data from the memory 160 and controls the current source 150 accordingly. The microcontroller may also control the current source 150 to adjust the brightness of the LEDs 100 in response to optical feedback received from the detectors 102.

The module additionally includes a signal conditioning/gain select/offset adjust block 156 comprised of amplifiers, switches, electronic filters, and a digital-to-analog converter. The block 156 adjusts the signals from the detectors 102 to increase gain, offset, and reduce noise. The microcontroller in the base instrument controls block 156 through a digital output register 158. The output register 158 receives data from the microcontroller and outputs control voltages to the block 156. The block 156 outputs the adjusted detector signals to the microcontroller through the analog-to-digital converter 154 and the edge connector 80. The module also includes the memory 160, preferably a serial EEPROM, for storing data specific to the module, such as calibration data for the LEDs 100, thermal plates 50A, 50B, and temperature sensors 52, as well as calibration data for a deconvolution algorithm described in detail below.

Referring again to FIG. 20, the controller 112 is programmed to perform the functions described in the operation section below. These functions include providing a user interface to enable a user to specify desired thermal processing parameters (e.g., set point temperatures and hold times at each temperature), thermal processing of samples according to the selected parameters, detection and measurement of optical signals emitted from the samples, and recording, manipulating, and analyzing the optical data. The creation of software and/or firmware for performing these functions can be performed by a computer programmer having ordinary skill in the art upon consideration of the following description. In addition, Appendix A lists exemplary source code for performing various functions described below relating to the manipulation and analysis of optical signals. The code is written in the Java programming language. The software and/or firmware may reside solely in the controller 112 or may be distributed between the controller and one or more microprocessors in the thermal cycler 108. Alternatively, the controller 112 may simply comprise one or more processors built into the thermal cycler 108.

In operation, the reactor system 106 is used to determine an unknown starting quantity of one or more target nucleic acid sequences in one or more test samples. The nucleic acid sequences in the samples may be amplified according to any known nucleic acid amplification method, including both thermal cycling amplification methods and isothermal amplification methods. Suitable thermal cycling methods useful in the practice of the present invention include, but are not limited to, the Polymerase Chain Reaction (PCR; U.S. Pat. Nos. 4,683,202, 4,683,195 and 4,965,188); Reverse Transcriptase PCR (RT-PCR); DNA Ligase Chain Reaction (LCR; International Patent Application No. WO 89/09835); and transcription-based amplification (D. Y. Kwoh et al. 1989, Proc. Natl. Acad. Sci. USA 86, 1173–1177). Suitable isothermal amplification methods useful in the practice of the present invention include, but are not limited to, Rolling Circle Amplification; Strand Displacement Amplification (SDA; Walker et al. 1992, Proc. Natl. Acad. Sci. USA 89, 392–396); Q-.beta. replicase (Lizardi et al. 1988, Bio/Technology 6, 1197–1202); Nucleic Acid-Based Sequence Amplification (NASBA; R. Sooknanan and L. Malek 1995, Bio/Technology 13, 563–65); and Self-Sustained Sequence Replication (3SR; Guatelli et al. 1990, Proc. Nati. Acad. Sci. USA 87, 1874–1878).

According to a first mode of operation, the thermal cycler 108 is used to amplify an unknown starting quantity of a target nucleic acid sequence in a test sample and a plurality of different known quantities of a calibration nucleic acid sequence in respective calibration samples (i.e., standards). Preferably, the nucleic acid sequences that are amplified in the calibration and test samples are the same or similar. Referring again to FIG. 2, each sample is placed into a separate reaction vessel by aspirating the sample into a pipette (not shown), inserting the pipette tip through the channel 28 into the chamber 17, and dispensing the sample into the chamber. It is presently preferred that the chamber 17 be filled from the bottom up by initially inserting the pipette tip close to the bottom of the chamber 17 and by slowly retracting the pipette tip as the chamber 17 is filled. Filling the chamber 17 in this manner reduces the likelihood that air bubbles will form in the chamber. Such air bubbles could have a negative effect on subsequent optical detection.

The sample may be mixed with chemicals necessary for the intended reaction (e.g., PCR reagents and fluorescent probes for labeling the nucleic acid sequences to be amplified) prior to being added to the chamber 17. Alternatively, the sample may be introduced to the chemicals in the chamber 17, e.g., by adding the chemicals to the chamber before or after the sample to form the desired reaction mixture in the chamber. In one embodiment, the reagents and fluorescent probes for the intended reaction are placed in the chamber 17 when the vessel is manufactured. The reagents are preferably placed in the chamber 17 in dried or lyophilized form so that they are adequately preserved until the vessel is used. After the chamber 17 is filled with the desired reaction mixture, the plunger 22 is inserted into the channel 28 to seal and pressurize the chamber 17.

Referring again to FIG. 20, each of the vessels 12 may be inserted between the thermal plates of a respective heat-exchanging module 60 either prior to filling and pressurizing the vessel or after filling and pressurizing the vessel. In either case, as shown in FIG. 5, the pressure in the chamber 17 forces the flexible major walls 18 to contact and conform to the inner surfaces of the plates 50. Further, each of the vessels may be manually filled and pressurized by a human operator or the vessels may be filled and pressurized by an automated machine, e.g., a pick-and-place machine. Various automated embodiments of the apparatus are described in U.S. application Ser. No. 09/468,690 filed Dec. 21, 1999 the disclosure of which is incorporated by reference herein.

Referring again to FIG. 20, the user then selects a desired thermal profile to be executed at each reaction site at which one of the vessels 12 is present. For example, for a PCR amplification, the user may select the thermal profile to begin with a 30 second induction hold at 95° C., followed by 45 thermal cycles in which the reaction mixture is cycled between higher and lower temperatures for denaturization, annealing, and polymerization. For example, each thermal cycle may include a first set point temperature of 95° C. which is held for 1 second to denature double-stranded DNA, followed by a second set point temperature of 60° C. which is held for 6 seconds for annealing of primers and polymerization. The user also enters into the controller 112 specific values related to the calibration and test samples. In particular, the user specifies in a setup table the specific site at which each sample is located, the starting quantity of each calibration nucleic acid sequence in each calibration sample, the specific dye being used to label the calibration sequence (e.g., FAM, TET, TAMRA, or ROX), and the specific dye being used to label each target nucleic acid sequence in the test sample(s).

The reaction mixtures contained in the vessels 12 are then subjected to the thermal profile selected by the user. The controller 112 preferably implements standard proportional-integral-derivative (PID) control to execute the selected thermal profile. Referring again to FIG. 23, for each heat-exchanging module in use, the controller receives signals indicating the temperatures of the plates 50A, 50B from the temperature sensors 52. Polling of the plate temperatures preferably occurs regularly throughout the running of the temperature profile. After each polling, the controller averages the temperatures of the two plates 50A, 50B to determine an average plate temperature. The controller then determines the difference (delta) between the profile target temperature, i.e. the set point temperature defined by the user for the particular time in the profile, and the average plate temperature. Based on the relationship between the average plate temperature and the current target temperature, the controller controls the amount of power supplied to the heating elements on the plates 50A, 50B or to the fan 66 as appropriate to reach or maintain the current set point temperature. Standard PID control is well known in the art and need not be described further herein.

The controller may optionally be programmed to implement a modified version of PD control described in International Publication Number WO 99/48608 published Sep. 30, 199. In this modified version of PID control, the controller is programmed to compensate for thermal lag between the plates 50A, 50B and reaction mixture contained in a reaction vessel inserted between the plates. The thermal lag is caused by the need for heat to transfer from the plates 50A, 50B through the flexible walls of the vessel and into the reaction mixture during heating, or by the need for heat to transfer from the reaction mixture through the walls of the vessel to the plates 50A, 50B during cooling. In standard PD control, the power supplied to a heating or cooling element is dependent upon the difference (error) between the actual measured temperature of the plates and the desired set point temperature. The average power being supplied to either the heating or cooling element therefore decreases as the actual temperature of the plates approaches the set point temperature, so that the reaction mixture does not reach the set point temperature as rapidly as possible. The modified version of PID control overcomes this disadvantage of standard PID control during rapid heating or cooling steps.

To compensate for the thermal lag during heating steps (i.e., to raise the temperature of the reaction mixture to a desired set point temperature that is higher than the previous set point temperature), the controller sets a variable target temperature that initially exceeds the desired set point temperature. For example, if the set point temperature is 95° C., the initial value of the variable target temperature may be set 2 to 100° C. higher. The controller next determines a level of power to be supplied to the heating elements to raise the temperature of the plates 50A, 50B to the variable target temperature by inputting the variable target temperature and the current average plate temperature to a standard PID control algorithm. The level of power to be supplied to the heaters is therefore determined in dependence upon the difference (error) between the average plate temperature and a target temperature that is higher than the desired set point temperature. The higher target temperature ensures that a higher level of power is supplied to heat the plates 50A, 50B, and therefore the reaction mixture, to the set point temperature more rapidly. The controller then sends a control signal to the power and source control circuit in the base instrument to provide power to the heating elements at the level determined.

When the temperature of the plates 50A, 50B is subsequently polled, the controller determines if the actual measured temperature of the plates is greater than or equal to a predetermined cutoff value. Suitable cutoff values are: the desired set point temperature itself; or 1 to 2° C. below the set point temperature, e.g., 93 to 94° C. for a set point temperature of 95° C. If the average plate temperature does not exceed the predetermined value, then the controller again determines a level of power to be supplied to the heating elements in dependence upon the difference between the average plate temperature and the target temperature and sends another control signal to provide power to the heaters at the level determined. This process is repeated until the average plate temperature is greater than or equal to the cutoff value.

When the average plate temperature is greater than or equal to the cutoff value, the controller decreases the variable target temperature, preferably by exponentially decaying the amount by which the variable target temperature exceeds the set point temperature. For example, the amount by which the variable target temperature exceeds the desired set point temperature may be exponentially decayed as a function of time according to the equation:

$$\Delta = (\Delta_{max}) * e(-t/\text{tau})$$

where $\Delta$ is equal to the amount by which the variable target temperature exceeds the desired set point temperature, $\Delta_{max}$ is equal to the difference between the initial value of the variable target temperature and the desired set point temperature, t is equal to the elapsed time in seconds from the start of decay, and tau is equal to a decay time constant. In the system of the present invention, tau preferably has a value in the range of 1 to 4 seconds. It is presently preferred to determine tau empirically for the heat-exchanging module during testing and calibration of the module and to store the value of tau in the memory 160 of the module before shipping it to the end user. Although the exponential equation given above is presently preferred, it is to be understood that many other decay formulas may be employed and fall within the scope of the invention. Moreover, the variable target temperature may be decreased by other techniques, e.g., it may be decreased linearly.

After decreasing the variable target temperature, the controller determines a new level of power to be supplied to the heating elements to raise the temperature of the plates 50A, 50B to the decreased target temperature. The controller determines the level of power by inputting the current plate temperature and decreased target temperature to the PID control algorithm. The controller then sends a control signal to provide power to the heaters at the new level determined. As the time in the thermal profile progresses, the controller continues to decrease the variable target temperature until it is equal to the set point temperature. When the variable target temperature is equal to the set point temperature, standard PID control is resumed to maintain the plates 50A, 50B at the set point temperature.

To compensate for the thermal lag during cooling steps (i.e., to lower the temperature of the reaction mixture to a desired set point temperature that is lower than the previous set point temperature), the controller preferably activates the fan 66 just prior to the completion of the previous set point temperature to allow the fan to achieve maximum speed for cooling (i.e., to allow for spin-up time). The controller then sets a variable target temperature that is initially lower than the desired set point temperature. For example, if the set point temperature is 60° C., the initial value of the variable target temperature may be set 2 to 10° C. lower, i.e., 50 to 58° C. The controller continues cooling with the fan 66 until the actual measured temperature of the plates 50A, 50B is less than or equal to a second cutoff value, preferably the variable target temperature. When the average plate temperature is less than or equal to the variable target temperature, the controller deactivates the fan 66 and increases the target temperature, preferably by exponentially decaying the amount by which the variable target temperature differs from the set point temperature using the exponential decay equation given above. For cooling, tau is preferably in the range of 1 to 5 seconds with a preferred value of about 3 seconds. As in the heating example given above, tau may be determined empirically for the heat-exchanging module during testing or calibration and stored in the memory 160.

The controller next determines a level of power to be supplied to the heating elements to raise the temperature of the plates 50A, 50B to the increased target temperature by inputting the current average plate temperature and the increased target temperature to the PID control algorithm. The controller then sends a control signal to the power and source control circuit in the base instrument to provide power to the heating elements at the level determined. As time in the thermal profile continues, the controller continues to increase the variable target temperature and issue control signals in this manner until the variable target temperature is equal to the set point temperature. When the variable target temperature is equal to the set point temperature, the controller resumes standard PID control to maintain the plates 50A, 50B at the set point temperature.

Referring again to FIG. 20, the reaction mixtures in the vessels 12 are optically interrogated in real-time as they are thermally processed. If the mixtures are being subjected to thermal cycling, then each mixture is preferably optically interrogated once per thermal cycle at the lowest temperature in the cycle. If isothermal amplification is employed, then each mixture is preferably optically interrogated at regular time intervals (e.g., every 10 seconds) during the amplification. Referring again to FIGS. 16 and 18, optical interrogation of an individual mixture in a reaction vessel 12 is accomplished by sequentially activating LEDs 100A, 100B, 100C, and 100D to excite different fluorescently-labeled nucleic acid sequences in the mixture and by detecting fluorescent signals emitted from the chamber 17 using detectors 102A, 102B, 102C, and 102D. In the following example of operation, the fluorescent dyes FAM, TAMRA, TET, and ROX are used to label the target nucleotide sequences in the reaction mixture.

There are four pairs of LEDs 100A, 100B, 100C, and 100D and four detectors 102A, 102B, 102C, and 102D for a total of sixteen combinations of LED/detector pairs. It is theoretically possible to collect output signals from the detectors for all sixteen combinations. Of these sixteen combinations, however, there are only four primary detection channels. Each primary detection channel is formed by a pair of LEDs in the optics assembly 68 whose excitation beams lie in the peak excitation wavelength range of a particular dye and by one corresponding channel in the optics assembly 70 designed to detect light emitted in the peak emission wavelength range of the same dye. The first primary detection channel is formed by the first pair of LEDs 100A and the fourth detector 102D (the ROX channel). The second primary detection channel is formed by the second pair of LEDs 100B and the third detector 102C (the TAMRA channel). The third primary detection channel is formed by the third pair of LEDs 100C and the first detector 102A (the FAM channel). The fourth primary detection channel is formed by the fourth pair of LEDs 100D and the second detector 102B (the TET channel).

Prior to activating any of the LEDs 100A, 100B, 100C, 100D, a "dark reading" is taken to determine the output signal of each of the four detectors 102A, 102B, 102C, 102D when none of the LEDs are lit. The "dark reading" signal output by each detector is subsequently subtracted from the corresponding "light reading" signal output by the detector to correct for any electronic offset in the optical detection circuit. This procedure of obtaining "dark reading" signals and subtracting the dark signals from the corresponding "light reading" signals is preferably performed every time that a reaction vessel is optically interrogated, including those times the vessel is interrogated during the development of calibration data (described in detail below). For clarity and brevity of explanation, however, the steps of obtaining "dark reading" signals and subtracting the dark signals from the corresponding "light reading" signals will not be further repeated in this description.

Following the dark reading, a "light reading" is taken in each of the four primary optical detection channels as follows. The first pair of LEDs 100A is activated and the LEDs generate an excitation beam that passes through the pair of 593 nm low pass filters 203, reflects off of the 593 nm low pass reflector 212, passes through the 555 nm low pass reflector 211, reflects off of the 527 nm high pass reflector 209, and passes through the lens 215 into the reaction chamber 17. The excitation beam from the LEDs 110A is thus filtered to a wavelength range of 555 to 593 nm corresponding to the peak excitation range for ROX. As shown in FIG. 18, emitted light (fluorescence emission radiation) from the chamber 17 passes through the lens 232 of the detection assembly 70 and strikes the 565 nm low pass reflector 229. The portion of the light having a wavelength over 605 nm (corresponding to the peak emission wavelength range of ROX) passes through the 565 nm low pass reflector 229, reflects from the 605 nm high pass reflector 227, reflects from the mirror 228, passes through the pair of 605 nm high pass filters 226, through the lens 242, through the 620 nm Schott Glass® filter 222D, and is detected by the fourth detector 102D. The fourth detector 102D outputs a corresponding signal that is converted to a digital value and recorded.

Next, as shown in FIG. 16, the second pair of LEDs 100B is activated and the LEDs generate an excitation beam that passes through the pair of 555 nm low pass filters 204, reflects off of the 555 nm low pass reflector 211, reflects off of the 527 nm high pass reflector 209, and passes through the lens 215 into the reaction chamber 17. The excitation beam from LEDs 100B is thus filtered to a wavelength range of 527 to 555 nm corresponding to the peak excitation range for TAMRA. As shown in FIG. 18, emitted light from the chamber 17 then passes through the lens 232 of the detection assembly 70 and strikes the 565 nm low pass reflector 229. The portion of the light having a wavelength in the range of about 565 to 605 nm (corresponding to the peak emission wavelength range of TAMRA) passes through the 565 nm low pass reflector 229, through the 605 nm high pass reflector 227, through the pair of 565 nm high pass filters 225, through the lens 242, through the 570 nm Schott Glass® filter 222C, and is detected by the third detector 102C. The third detector 102C outputs a corresponding signal that is converted to a digital value and recorded.

Next, as shown in FIG. 16, the pair of blue LEDs 100C is activated and the LEDs generate an excitation beam that passes through the pair of 495 nm low pass filters 205, through the 495 nm high pass reflector 208, through the 527 nm high pass reflector 209, and through the lens 215 into the reaction chamber 17. The excitation beam from LEDs 100C is thus filtered to a wavelength range of about 450 to 495 nm corresponding to the peak excitation range for FAM. As shown in FIG. 18, emitted light from the chamber 17 then passes through the lens 232 of the detection assembly 70 and strikes the 565 nm low pass reflector 229. The portion of the light having a wavelength in the range of about 505 to 537 nm (corresponding to the peak emission wavelength range of FAM) reflects from the 565 nm low pass reflector 229, passes through the 537 nm high pass reflector 230, reflects from the 505 nm high pass reflector 231, passes through the pair of 505 nm high pass filters 223, through the lens 242, through the 515 nm Schott Glass® filter 222A, and is detected by the first detector 102A. The first detector 102A outputs a corresponding signal that is converted to a digital value and recorded.

Next, as shown in FIG. 16, the fourth pair of LEDs 100D is activated and the LEDs generate an excitation beam that passes through the pair of 527 nm low pass filters 206, reflects off of the mirror 210, reflects off of the 495 nm high pass reflector 208, passes through the 527 nm high pass reflector 209, and passes through the lens 215 into the reaction chamber 17. The excitation beam from LEDs 100D is thus filtered to a wavelength range of 495 to 527 nm corresponding to the peak excitation range for TET. As shown in FIG. 18, emitted light from the chamber 17 then passes through the lens 232 of the detection assembly 70 and strikes the 565 nm low pass reflector 229. The portion of the light having a wavelength in the range of about 537 to 565 nm (corresponding to the peak emission wavelength range of TET) reflects from the 565 nm low pass reflector 229, reflects from the 537 nm high pass reflector 230, passes through the pair of 537 nm high pass filters 224, through the lens 242, through the 550 nm Schott Glass® filter 222B, and is detected by the second detector 102B. The second detector 102B outputs a corresponding signal that is converted to a digital value and recorded. The total time required to activate each of the four LEDs 100A, 100B, 100C, 100D in sequence and to collect four corresponding measurements from the detectors 102A, 102B, 102C, 102D is typically five seconds or less.

The spectrum of the fluorescence that is emitted by the dyes used for detection is usually broad. As a result, when an individual dye (e.g., FAM, TAMRA, TET, or ROX) emits fluorescence from the reaction vessel 12, the fluorescence can be detected in several of the primary detection channels, i.e. several of the detectors 102A, 102B, 102C, and 102D detect the fluorescence. However, each dye has its own 'signature', i.e., the ratios of the optical signals in each detection channel are unique to each dye. It is also a reasonable assumption that the fluorescent emission from a mixture of dyes are simply additive in each of the detection channels, so that the individual dye signals of a dye mixture can be extracted from the mixed signals using linear algebra.

In the preferred embodiment, the controller is programmed to convert the output signals of the detectors to values indicating the true signal from each dye in a reaction mixture using linear algebra and a calibration matrix. A preferred method for developing the calibration matrix will now be described using the four-channel optical system of the preferred embodiment as an example. First, a reaction vessel containing only reaction buffer is optically read using optics assemblies 68, 70. The reaction buffer should be a fluid similar or nearly identical to the reaction mixtures that will be optically read by the optics assemblies during production use of the system to test samples. The reaction buffer should contain no dyes, so that the concentrations of all dyes are zero. The optical reading of the reaction buffer in the four primary detection channels produces four output signals that are converted to corresponding digital values. These four numbers are called Buffer(I), where 'I' is 1, 2, 3 or 4 depending upon which detection channel is read. The buffer values are a measure of the background signal or scattered light detected in each primary detection channel without any added fluorescent signal from dyes.

Next, a reaction mixture containing a known concentration (e.g., 100 nM) of dye #1 is placed into the vessel and again the four channels are read. The four numbers produced are called Rawdye(I, 1). Similar sets of four numbers are obtained for the other three dyes to obtain Rawdye(I, 2), Rawdye(I, 3), and Rawdye(I, 4). The buffer values are then subtracted from the raw dye values to obtain net dye values as follows:

$$\text{Netdye}(I,J)=\text{Rawdye}(I,J)-\text{Buffer}(I);$$

where I indicates the detection channel, and J indicates the dye number.

The matrix Netdye(I, J) is then inverted using standard numerical methods (such as Gaussian elimination) to obtain a new matrix called the calibration matrix Cal(I,J). Note that the matrix product of Netdye(I, J)*Cal (I,J) is the unity matrix. Now, any reaction mixture can be read and the raw mixed fluorescent signals detected and measured by the four detectors may be converted to values representative of the individual signal emitted by each dye. The optical reading of the mixture produces four numbers called RawMix(I). The reaction buffer values are then subtracted from the raw mix values to obtain four numbers called Mix(I) as follows:

$$\text{Mix}(I)=\text{RawMix}(I)-\text{Buffer}(I)$$

Next, the true dye signals are obtained by matrix multiplication as follows:

$$\text{Truedye}(I)=100\ \text{nM}*\text{Cal}(I,J)*\text{Mix}(I)$$

In the above equation, the factor of 100 comes from the fact that a concentration of 100 nM was used for the initial calibration measurements. The concentration of 100 nM is used for purposes of example only and is not intended to limit the scope of the invention. In general, the dye concentrations for calibration measurements should be somewhere in the range of 25 to 2,000 nM depending upon the fluorescent efficiency (strength) of the dyes and their use in a particular assay. When displayed to a user, the fluorescent signal values may be normalized to an arbitrary scale having arbitrary units of fluorescent intensity (e.g., a scale ranging from 0 to 1000 arbitrary units).

Referring again to FIGS. 22–23, the matrices Cal(I, J) and Buffer(I) are preferably produced during the manufacture of each heat-exchanging module 60 and stored in the memory 160. When the module 60 is plugged into the base instrument 110, the controller reads the matrices into memory and uses the matrices to deconvolve the raw fluorescent signals. Because the calibration matrices Cal(I, J) and Buffer(I) are dependent upon the particular set of dyes calibrated and the volume of the reaction vessel, it is also preferred to produce and store multiple sets of the matrices for various combinations of dye sets and reaction vessel volumes. This gives the end user greater flexibility in using the system.

As one example, calibration matrices could be stored for three different dye sets to be used with three different sizes of reaction vessels (e.g., 25 µl, 50 µl, 100 µl) for a total of nine different sets of calibration matrices of course, this is just one example, and many other combinations will be apparent to one skilled in the art upon reading this description. Further, in alternative embodiments, the control software may include functionality to guide the end user through the calibration procedure to enable the user to store and use calibration data for his or her own desired combination of dyes and reaction vessel size.

In one possible implementation of the four-channel system, three of the optical channels are used to detect amplified nucleic acid sequences while the fourth channel is used to monitor an internal control to check the performance of the system. For example, beta actin is often used as an internal control in nucleic acid amplification reactions because it has a predictable amplification response and can be easily labeled and monitored to verify that the amplification is occurring properly. In another possible implementation of the four-channel system, two of the optical channels are utilized to detect target nucleic acid sequences, one of the channels is used to monitor an internal control, and the fourth channel is used to monitor a passive normalizer. The passive normalizer is a dye that is placed in a reaction mixture in a known concentration and in a free form so that it will not label any target nucleic acid sequence. For example, ROX in a concentration of 100 to 500 nM makes a suitable passive normalizer. Because the passive normalizer is placed in a reaction mixture in a free form, the intensity of the fluorescent signal output by the passive normalizer is substantially unaffected by the presence or absence of a target nucleic acid sequence in the reaction mixture. The intensity of the signal does vary, however, due to such effects as evaporation of the mixture, variances in reaction vessel shapes, or air bubbles in the vessel. The intensity of the signal from the passive normalizer is monitored throughout the reaction and used to normalize the optical signals collected from the other three detection channels. If the signal from the passive normalizer changes due to evaporation, variances in reaction vessel shapes, or air bubbles in the vessel, the signals received in the other three detection channels are normalized for these variances.

Referring again to FIG. 20, the controller 112 stores in memory the deconvolved fluorescent signal values determined for each primary detection channel at each reaction site in use. The signal values are preferably stored in an array indexed by reaction site, detection channel, and cycle number (or time value for isothermal amplification). The signal values stored for a particular detection channel at a particular site define a growth curve for a target nucleic acid sequence being amplified at that site and detected in that channel.

Figure 24A:
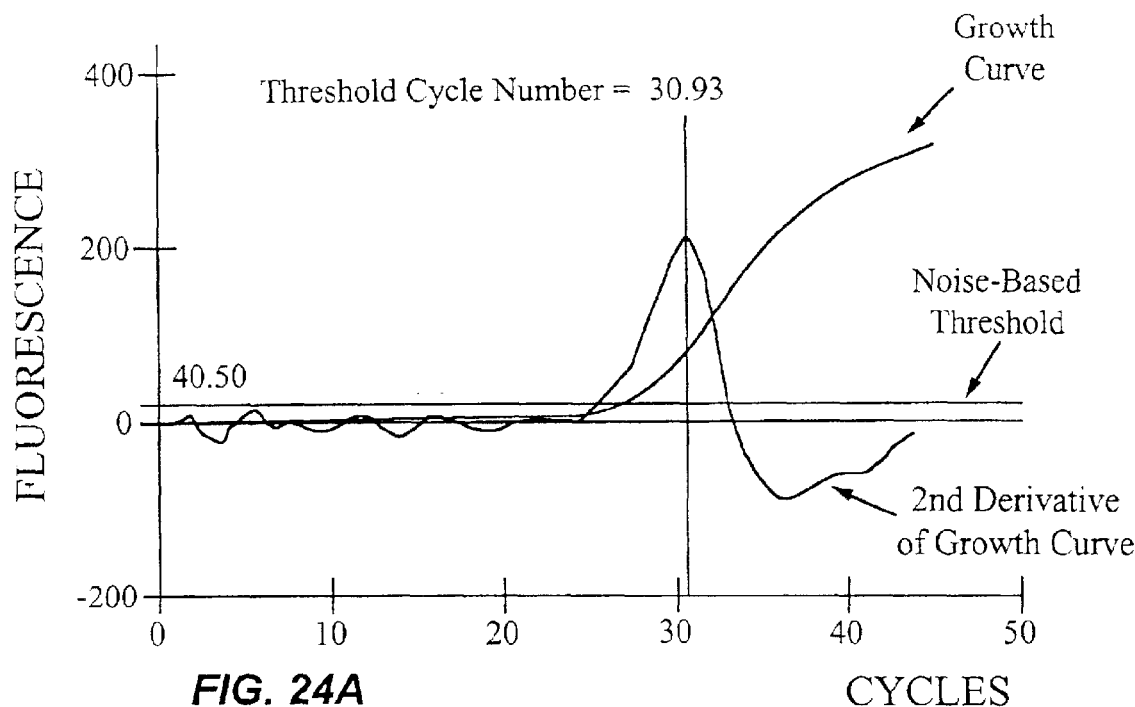
FIG. 24A is a graph showing a growth curve for a thermal cycling nucleic acid amplification reaction. A threshold cycle number is calculated as the location of the positive peak of the second derivative of the growth curve.

FIG. 24A shows a typical growth curve for a nucleic acid sequence being amplified in a thermal cycling reaction (e.g., PCR). The growth curve shows fluorescent intensity (and hence the relative quantity or concentration of the nucleic acid sequence) as a function of cycle number in the reaction. As the reaction proceeds, the concentration of detectable fluorescent dye increases. In a typical reaction, every cycle of PCR results in a doubling of product. As the reactants start to become depleted, the reaction shifts from two-fold logarithmic growth to linear growth, and eventually with additional cycles, a plateau is reached. The plateau region can vary greatly from reaction to reaction, and conventional endpoint measurements used for quantitative analysis have very poor reproducibility. However, product accumulation in the log phase is typically uniform. In order to perform quantitative PCR, a threshold cycle value is determined for each target nucleic acid sequence being amplified in the test and calibration samples. It is important that the method used to determine threshold values give reproducible values. By locating the threshold value in the log phase of the growth curve, such reproducibility is achievable.

Figure 24B:
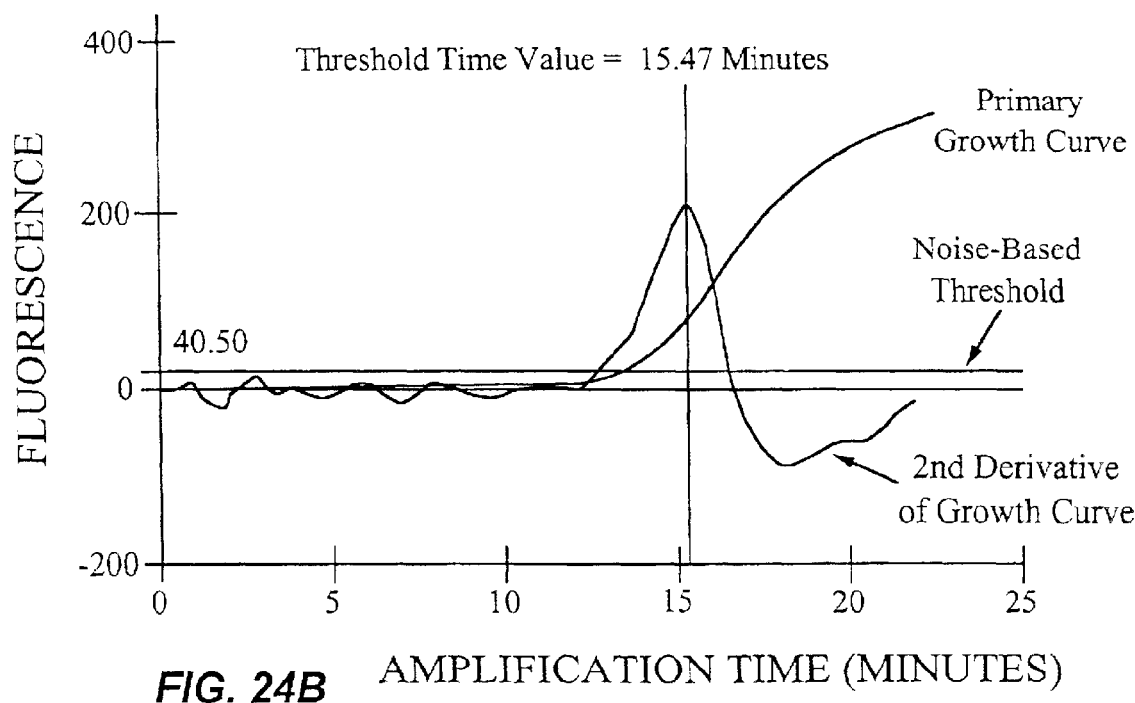
FIG. 24B is a graph showing a growth curve for an isothermal nucleic acid amplification reaction. A threshold time value is calculated as the location of the positive peak of the second derivative of the growth curve.

In particular, it is presently preferred to calculate a second derivative (with respect to cycle number) of the growth curve and to calculate the threshold cycle number as the location, in cycles, of the positive peak of the second derivative. For example, FIG. 24A shows a threshold cycle number of 30.93 at the positive peak of the second derivative. The method of the present invention may also be applied to isothermal nucleic acid amplification reactions. FIG. 24B shows a typical growth curve for a nucleic acid sequence being amplified in an isothermal reaction (e.g., Rolling Circle Amplification). The growth curve shows fluorescent intensity (and hence the relative quantity of the nucleic acid sequence) as a function of amplification time. A second derivative (with respect to time) of the growth curve is calculated, and a threshold time value of 15.47 minutes has been calculated at the positive peak of the second derivative. In alternative embodiments, characteristics other than the positive peak of the second derivative may be used to determine threshold values. For example, the threshold value may be calculated from the location of the negative peak of the second derivative, the zero-crossing of the second derivative, or the positive peak of the first derivative. These embodiments are described in greater detail below.

Figure 25:
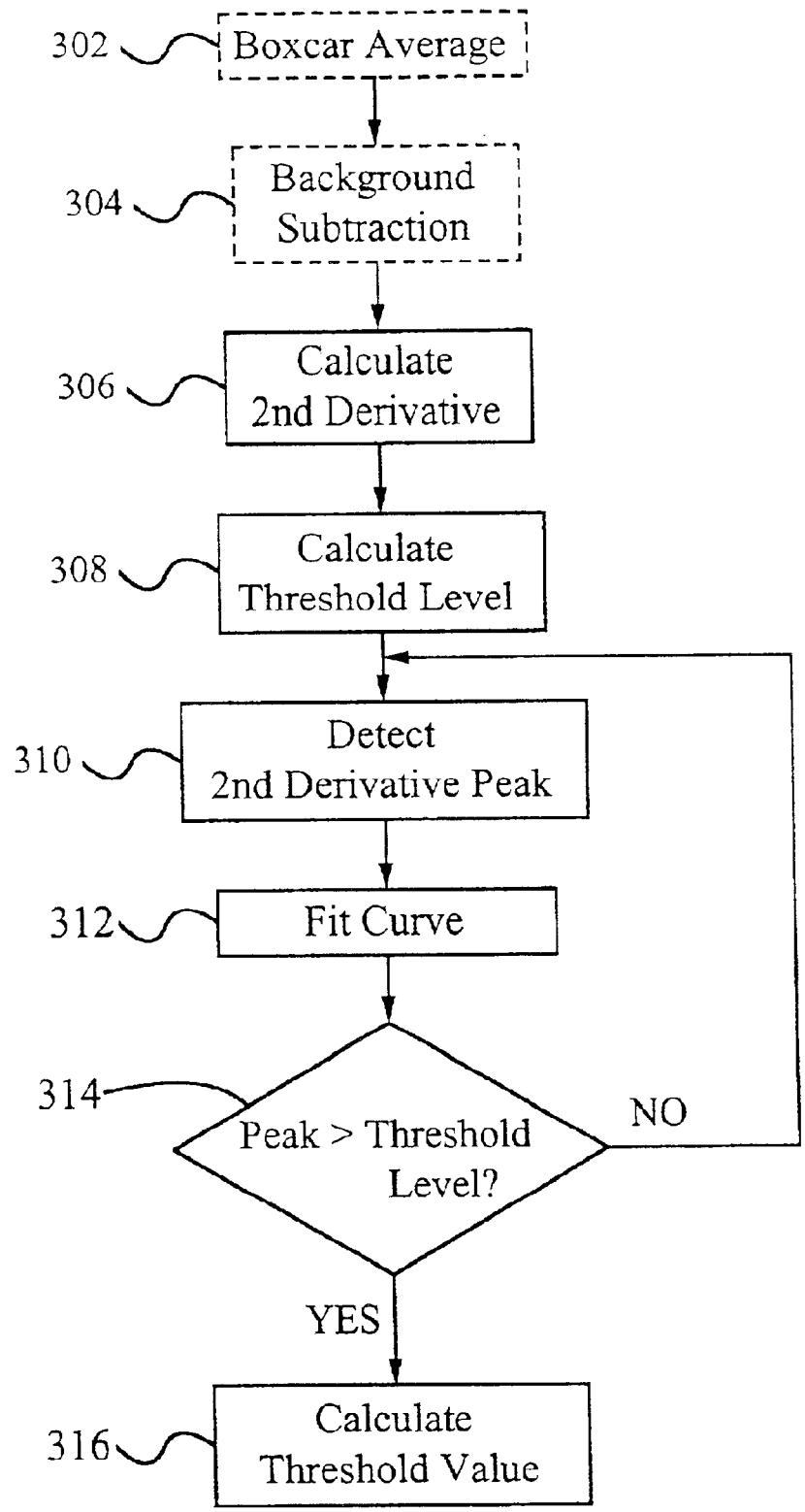
FIG. 25 is a flow chart illustrating steps executed to calculate a threshold value in a nucleic acid amplification reaction according to a preferred embodiment of the invention.

FIG. 25 is a flow chart showing the preferred method steps executed by the controller to determine a threshold value (e.g., a threshold cycle number or threshold time value) for a nucleic acid sequence in a test or calibration sample. The threshold value is determined from the deconvolved fluorescent signal values calculated for the specific reaction site and detection channel at which the growth of the nucleic acid sequence was measured. In optional steps 302 and 304, the signal values are preprocessed prior to threshold calculation. In optional step 302, boxcar averaging is performed on the signal values as follows. The average of the set of values $\{n, n-1, \ldots, n+1-k\}$ is used as the value for cycle n. For example, if k=2, then the data from cycles 4 and 5 are averaged and used as the data for cycle 5. In optional step 304, background subtraction is performed on the signal values.

Figure 26:
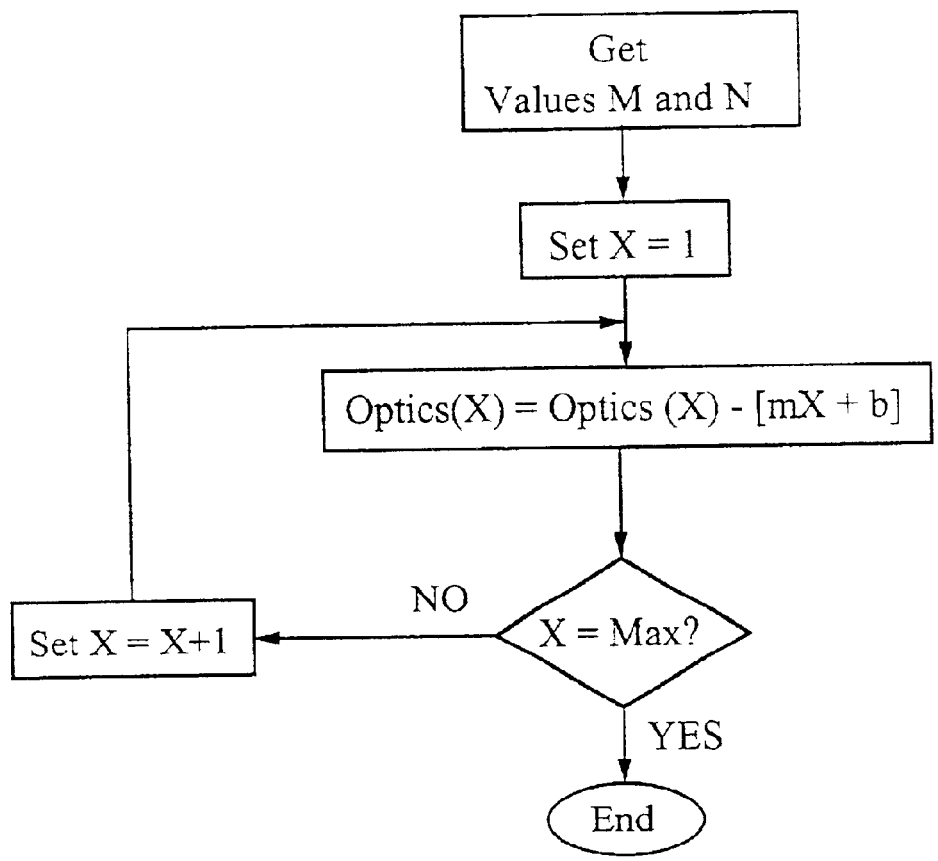
FIG. 26 is a flow chart illustrating the steps executed in a "background subtraction" routine.
Figure 27:
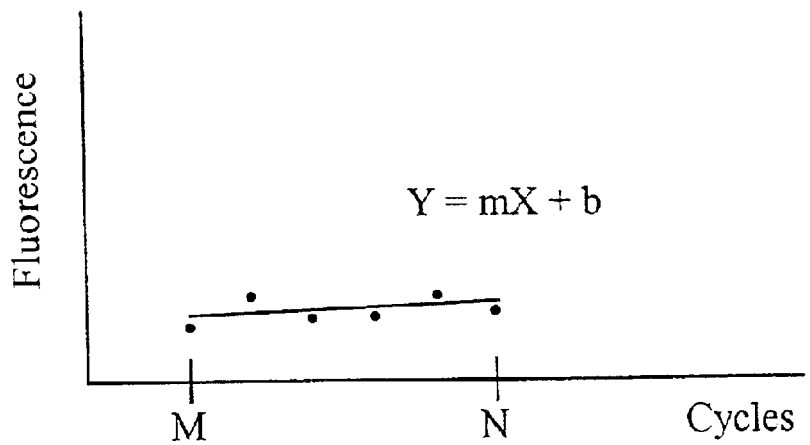
FIG. 27 is a graph of fluorescent signal value as a function of cycle number for cycles M to N.

FIGS. 26–27 illustrate background subtraction. Using a least squares algorithm, a line y=mX+b (where y is the signal value, m is the slope, X is the cycle number and b is the intercept) is fit to the signal values recorded for cycles M to N (preferably cycles 3 to 8). M and N are integers selected by the user. The equation of the line is used to decrease each signal value recorded for a cycle number by the value of the fitted line corresponding to the cycle number, according to the equation:

$$\mathrm{Optic}(X) = \mathrm{Optic}(X) - [mX+b]$$

where X is equal to the cycle number, Optic(X) is equal to the signal value at cycle number X, and m and b are fitted parameters of the line. The effect of the background subtraction is to subtract the baseline signal and its linear drift from the signal values.

Figure 28A:
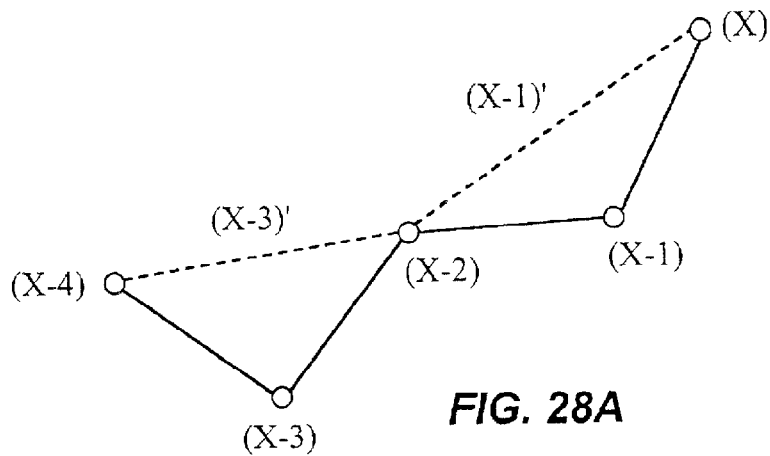
FIGS. 28A–28C illustrate five data points defining one segment of a growth curve.

In step 306, second derivative data points are calculated from the signal values. Preferred methods for calculating the second derivative data points will now be described with reference to FIGS. 28A–28C. FIG. 28A shows a segment of a growth curve defined by five consecutive signal values $\{\mathrm{Optic}_{(X-4)}, \mathrm{Optic}_{(X-3)}, \ldots, \mathrm{Optic}_{(X)}\}$ where x is equal to the cycle number (or measurement time point in isothermal amplification) at which the signal was measured. Thus, $\mathrm{Optic}_{(X-2)}$ is equal to the signal value two cycles prior to cycle number x. The controller preferably calculates the second derivative (with respect to x) of the growth curve at point $\mathrm{Optic}_{(X-2)}$ using equation (1):

$$\mathrm{2ndDeriv}_{(X-2)} = [\mathrm{Optic}_{(X)} - 2*\mathrm{Optic}_{(X-2)} + \mathrm{Optic}_{(X-4)}]*k; \qquad (1)$$

where k is equal to a constant multiplier (e.g., 5). The purpose of the constant multiplier is to make the second derivative curve (FIG. 24A) appear taller when displayed to the user. Neither the constant multiplier nor the displaying of the primary or second derivative curves are necessary to practice the invention and may be omitted in alternative embodiments.

The derivation of equation (1) will now be explained with reference to FIG. 28A. The second derivative of the growth curve at point $\text{Optic}_{(X-2)}$ is given by equation (2):

$$2\text{ndDeriv}_{(X-2)} = [1\text{stDeriv}_{(X-1)} - 1\text{stDeriv}_{(X-3)}]/2; \qquad (2)$$

The first derivative of the growth curve at point $\text{Optic}_{(X-1)}$ is given by equation (3):

$$1\text{stDeriv}_{(X-1)} = [\text{Optic}_{(X)} - \text{Optics}_{(X-2)}]/2; \qquad (3)$$

In addition, the first derivative of the growth curve at point $\text{Optic}_{(X-3)}$ is given by equation (4):

$$1\text{stDeriv}_{(X-3)} = [\text{Optic}_{(X-2)} - \text{Optic}_{(X-4)}]/2; \qquad (4)$$

Combining equations (2), (3), and (4) and multiplying by the constant multiplier k yields equation (1).

Equation (1) may be used to calculate the second derivative of the growth curve at any point on the curve for which the two prior and two subsequent signal values are known. This is not possible, however, for the last two signal values on the growth curve. Therefore, different equations are necessary for second derivative calculations for these points.

Figure 28B:
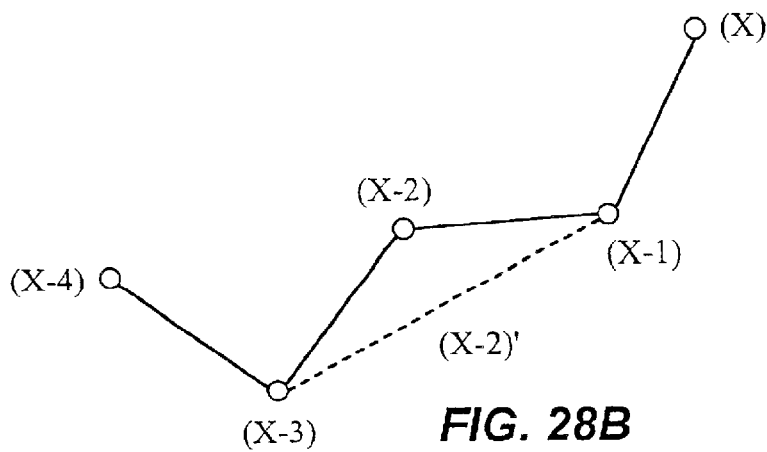
Figure 28C:
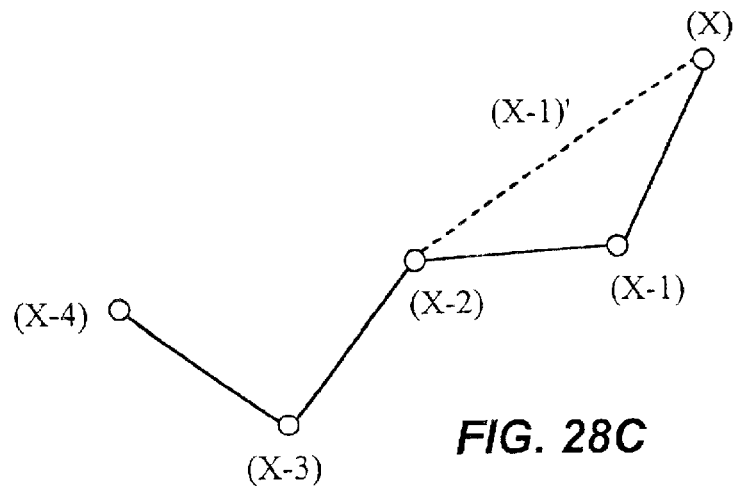

Referring to FIG. 28B, the second derivative of the growth curve at point $\text{Optic}_{(X-1)}$ is given by equation (5):

$$2\text{ndDeriv}_{(X-1)} = [\text{Optic}_{(X)} - \text{Optic}_{(X-1)} - 1\text{stDeriv}_{(X-2)}]/2; \qquad (5)$$

The first derivative of the growth curve at point $\text{Optic}_{(X-2)}$ is given by equation (6):

$$1\text{stDeriv}_{(X-2)} = [\text{Optic}_{(X-1)} - \text{Optics}_{(X-3)}]/2; \qquad (6)$$

Combining equations (5) and (6) and multiplying by the constant multiplier k yields equation (7):

$$2\text{ndDeriv}_{(X-1)} = [2*\text{Optic}(x) - 3*\text{Optic}_{(X-1)} + \text{Optic}_{(X-3)}]*k; \qquad (7)$$

Equation (7) may be used to calculate the second derivative of the growth curve at any point for which at least two previous and one subsequent signal values are known. If no subsequent signal value is known, then the second derivative may be calculated at a point Optic(x) using another equation which will now be described with reference to FIG. 28C. Specifically, the second derivative of the growth curve at point Optic(x) is given by equation (8):

$$2\text{ndDeriv}_{(X)} = [\text{Optic}_{(X)} - \text{Optic}_{(X-1)}] - 1\text{stDeriv}_{(X-1)}; \qquad (8)$$

The first derivative of the growth curve at point $\text{Optic}_{(X-1)}$ is given by equation (3):

$$1\text{stDeriv}_{(X-1)} = [\text{Optic}_{(X)} - \text{Optic}_{(X-2)}]/2; \qquad (3)$$

Combining equations (3) and (8) and multiplying by the constant multiplier k yields equation (9):

$$2\text{ndDeriv}_{(X)} = [\text{Optic}_{(X)} - 2*\text{Optic}_{(X-1)} + \text{Optic}_{(X-2)}]*2*k; \qquad (9)$$

In the preferred embodiment, the controller displays the growth curve and the second derivative of the growth curve to the user in real-time on a graphical user interface. When a new fluorescent signal value Optic(x) is received, the controller calculates a second derivative of the growth curve at Optic(x) using equation (9). When a subsequent signal value $\text{Optic}_{(X+1)}$ is received, the controller recalculates the second derivative of the growth curve at Optic(x) using equation (7). When another signal value $\text{Optic}_{(X+2)}$ is received, the controller recalculates the second derivative of the growth curve at Optic(x) using equation (1). Thus, previously calculated second derivative values are updated as new signals are measured. Although this dynamic updating of second derivative values is useful for real-time display, dynamic updating is not necessary to practice the invention. For example, all signal values for an amplification reaction may be recorded before calculating second derivative values, and the second derivative values may be calculated using just one equation rather than three.

Figure 29:
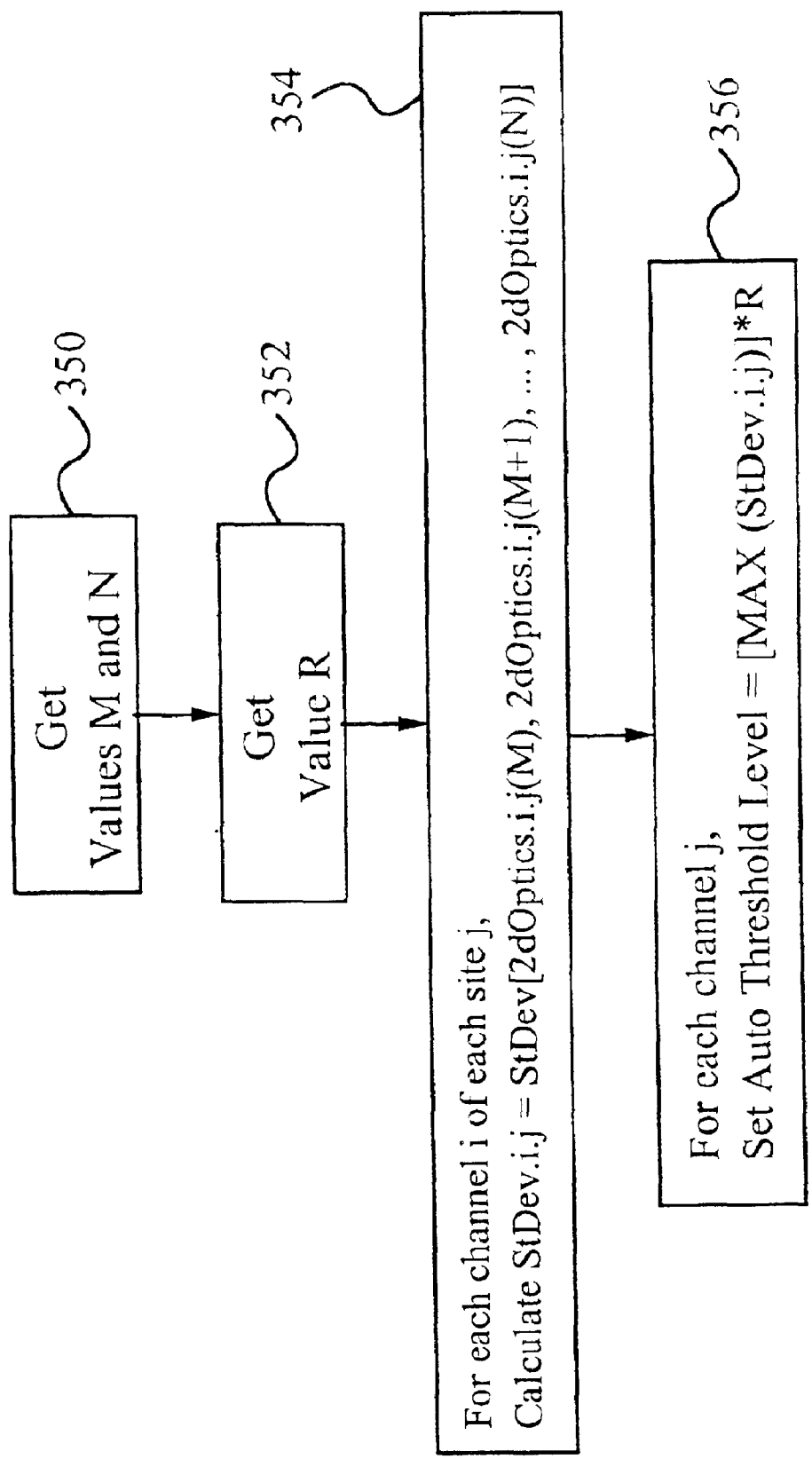
FIG. 29 is a flow chart illustrating the step executed to calculate a noise-based threshold level to be exceeded by the positive peak of the second derivative of a growth curve.

In step 308, the controller calculates a noise-based threshold level for the positive peak of the second derivative to exceed. FIG. 29 is a flow chart showing the steps executed by the controller to calculate the threshold level. For each primary detection channel at each reaction site in use, the controller calculates the standard deviation of the second derivative values calculated for the detection channel for cycles M to N (preferably cycles 3 to 8). The controller next sets the threshold level for each detection channel equal to R times the maximum standard deviation calculated for the channel. For example, assume that 8 sites are in use (labeled A1–A8) and the FAM channel is used to detect and measure the growth of a target nucleic acid sequence at each of the sites. For each site, based on the deconvolved signal values calculated for the FAM channel for cycles M to N, the controller calculates second derivative data points for cycles M to N. The controller also calculates the standard deviation of the second derivative data points and sets the threshold level for each FAM channel equal to R times the largest standard deviation found. Thus, the reaction site whose FAM channel has the largest standard deviation in the values of its second derivative data points for cycles M to N is used to set the threshold level for all FAM channels in the batch. M, N, and R are preferably user-defined integers. Reasonable values for M and N are 3 and 8, respectively. The value of R is preferably in the range of 3 to 10, with a preferred value of 5. Although it is presently preferred to calculate an automatic, noise-based threshold level in this manner, the threshold level may also be set manually by the user.

Referring again to FIG. 25, in step 310, the controller detects a positive peak of the second derivative. The positive peak is preferably detected using at least three second derivative data points calculated at cycles X, X–1, an X–2. A positive peak is detected if the second derivative value at cycle X is less than the second derivative value at cycle X–1 and if the second derivative value at cycle X–1 is greater than the second derivative value at cycle X–2. After a peak is detected, a second order curve is fit to the three second derivative data points, step 312. In decision step 314, it is determined if the height of the peak of the second order curve exceeds the threshold level calculated in step 308. If the peak of the second order curve does not exceed the threshold level, the controller returns to step 310 and looks for the next positive peak in the second derivative. If the peak of the second order curve does exceed the threshold level, the controller proceeds to step 316. In step 316, the controller calculates the threshold value (e.g., the threshold cycle number in thermal cycling amplification or time value in isothermal amplification) as the location of the peak of the second order curve.

Figure 30:
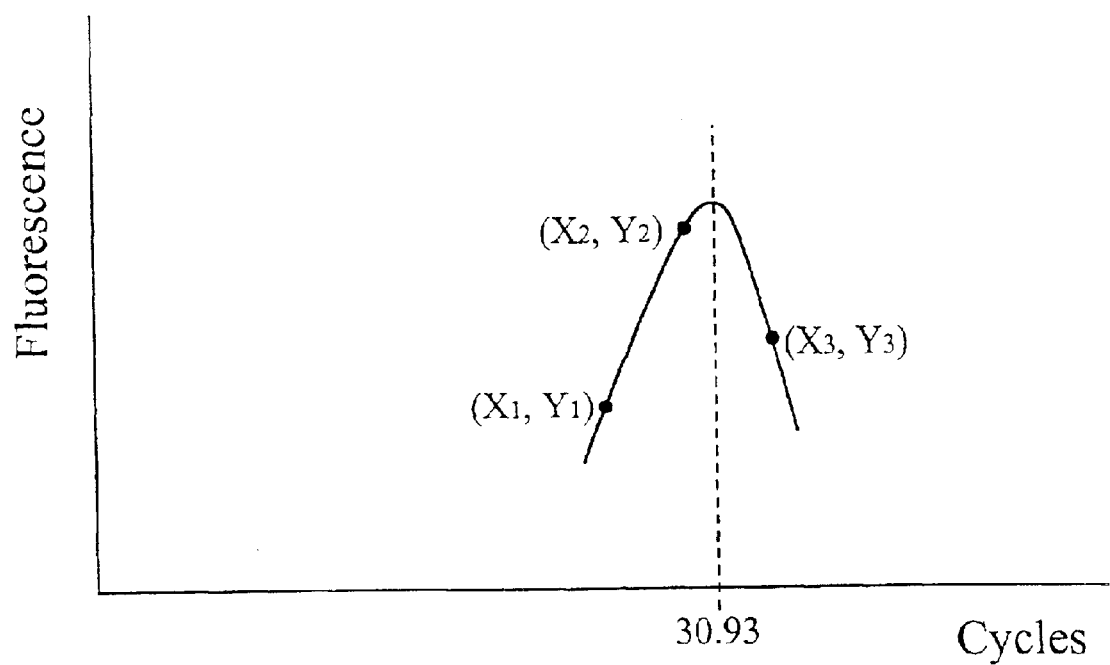
FIG. 30 is a graph illustrating the fitting of a second order curve to three data points.
Figure 31:
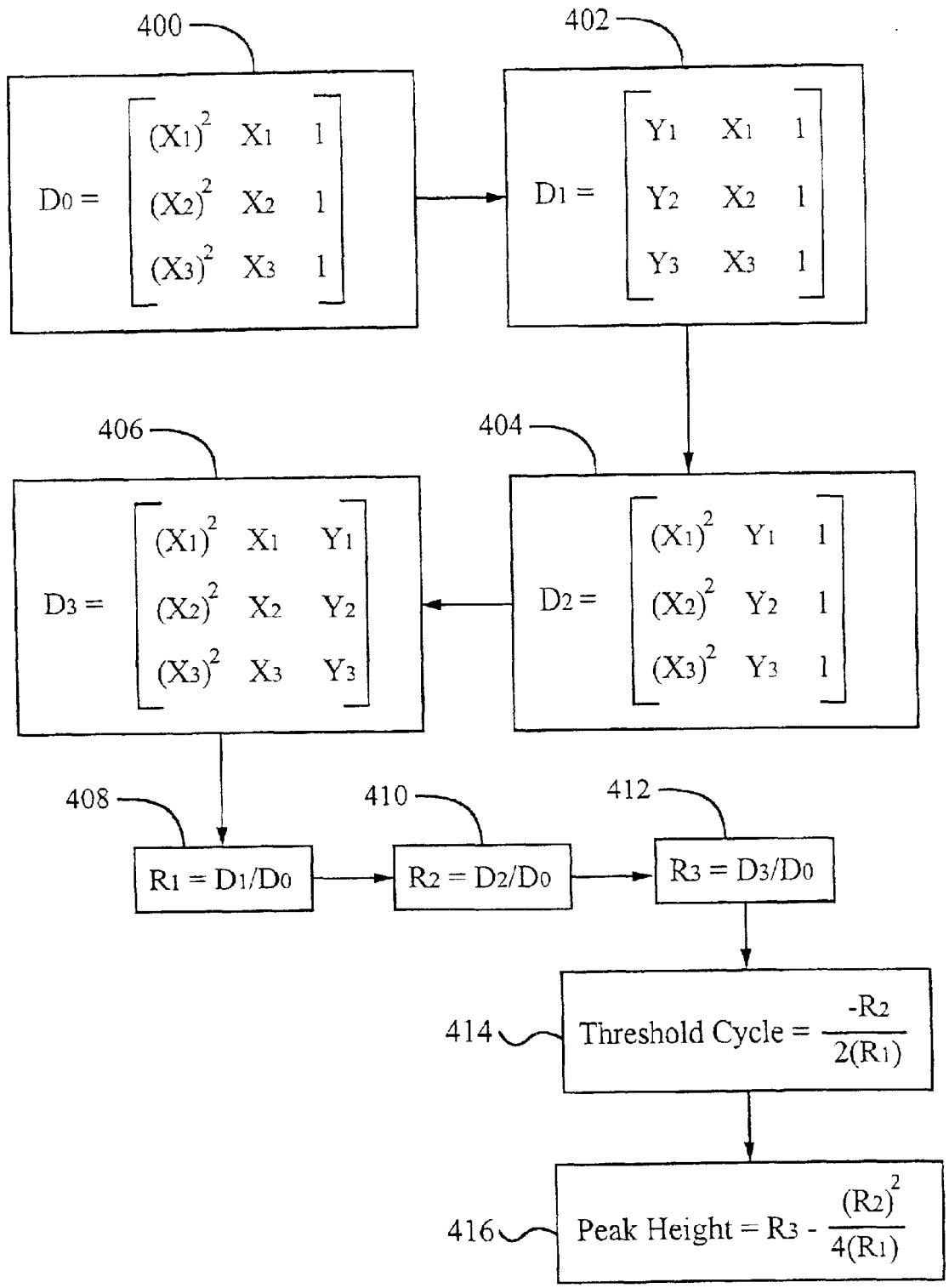
FIG. 31 is a flow chart showing the steps performed to calculate a peak height and threshold value of the second order curve of FIG. 30.

FIG. 30 illustrates the fitting of a second order curve to the three second derivative data points used to detect a peak in the second derivative. To locate the true maximum of the second derivative peak and the cycle number (or time value) at which it occurs, the controller executes a peak finding algorithm. Let (X1, Y1), (X2, Y2), and (X3, Y3) be the three second derivative data points for the analysis. Y2 is the value of the highest point, and X2 is the cycle (or time of amplification) where that point has occurred. In addition, X1=X2−1 and X3=X2+1. FIG. 31 illustrates the steps executed to calculate the height of the peak of the second order curve and the cycle number of the peak. In steps 400–406, four determinants are calculated using the xy values of the three second derivative data points. In steps 408–412, three ratios R1, R2, R3 are calculated from the determinants. In step 414, the threshold value (which may be fractional) is calculated from the ratios. In step 416, the height of the peak of the second order curve is calculated using the formula shown.

Figure 32A:
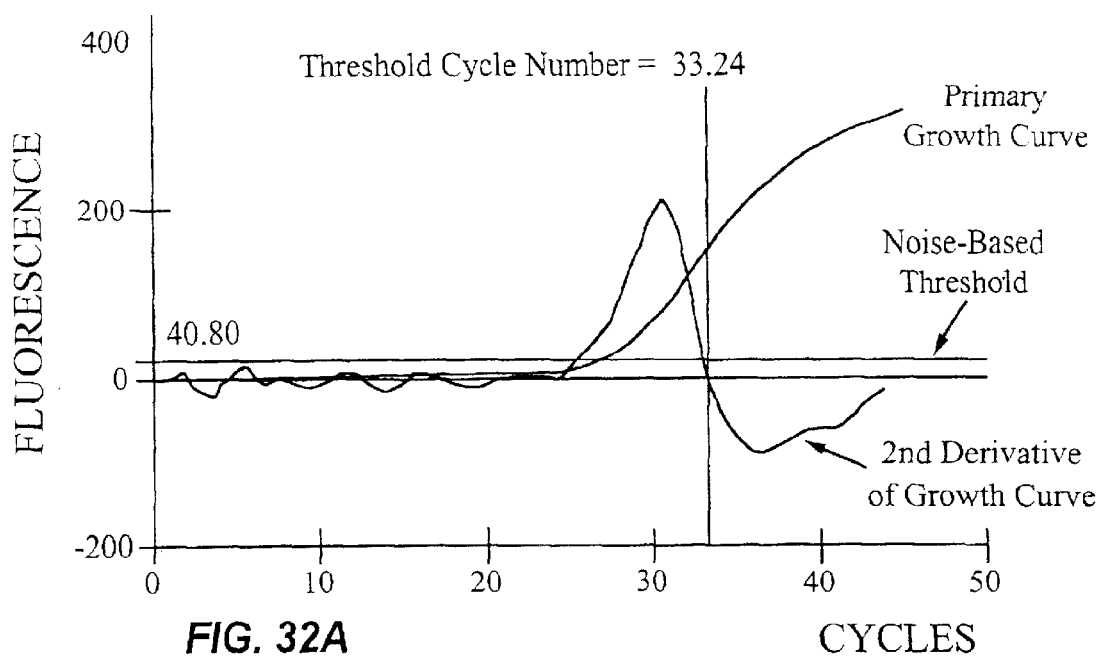
FIG. 32A is a graph showing a growth curve for a thermal cycling nucleic acid amplification reaction. A threshold cycle number is calculated as the location of the zero-crossing of the second derivative of the growth curve.
Figure 32B:
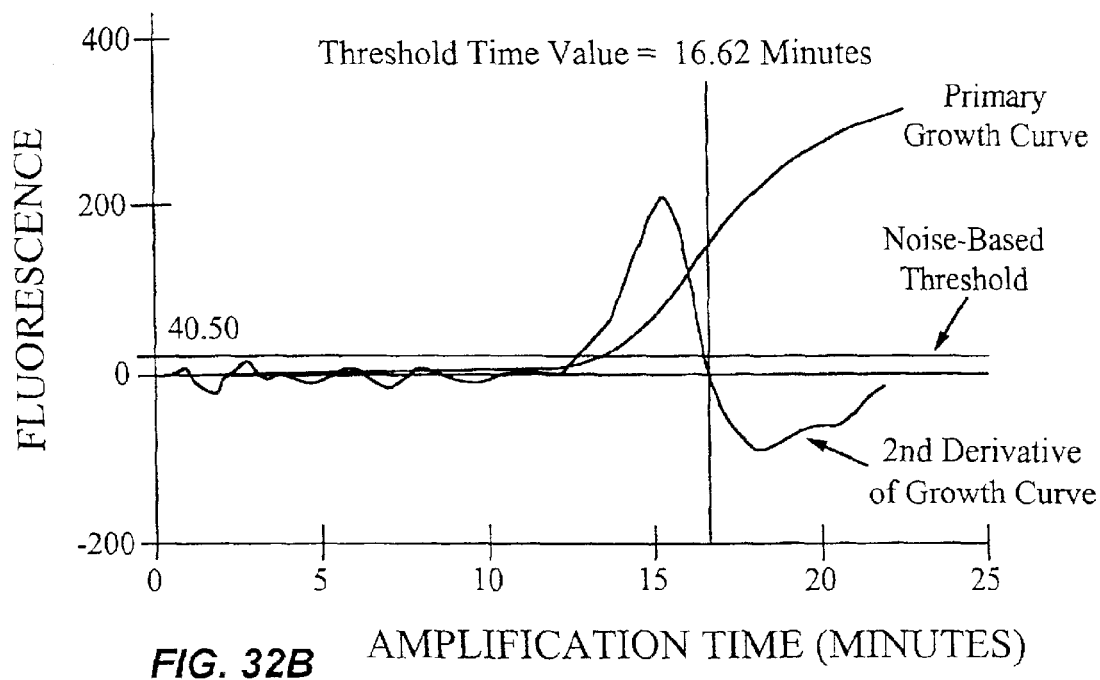
FIG. 32B is a graph showing a growth curve for an isothermal nucleic acid amplification reaction. A threshold time value is calculated as the location of the zero-crossing of the second derivative of the growth curve.
Figure 33:
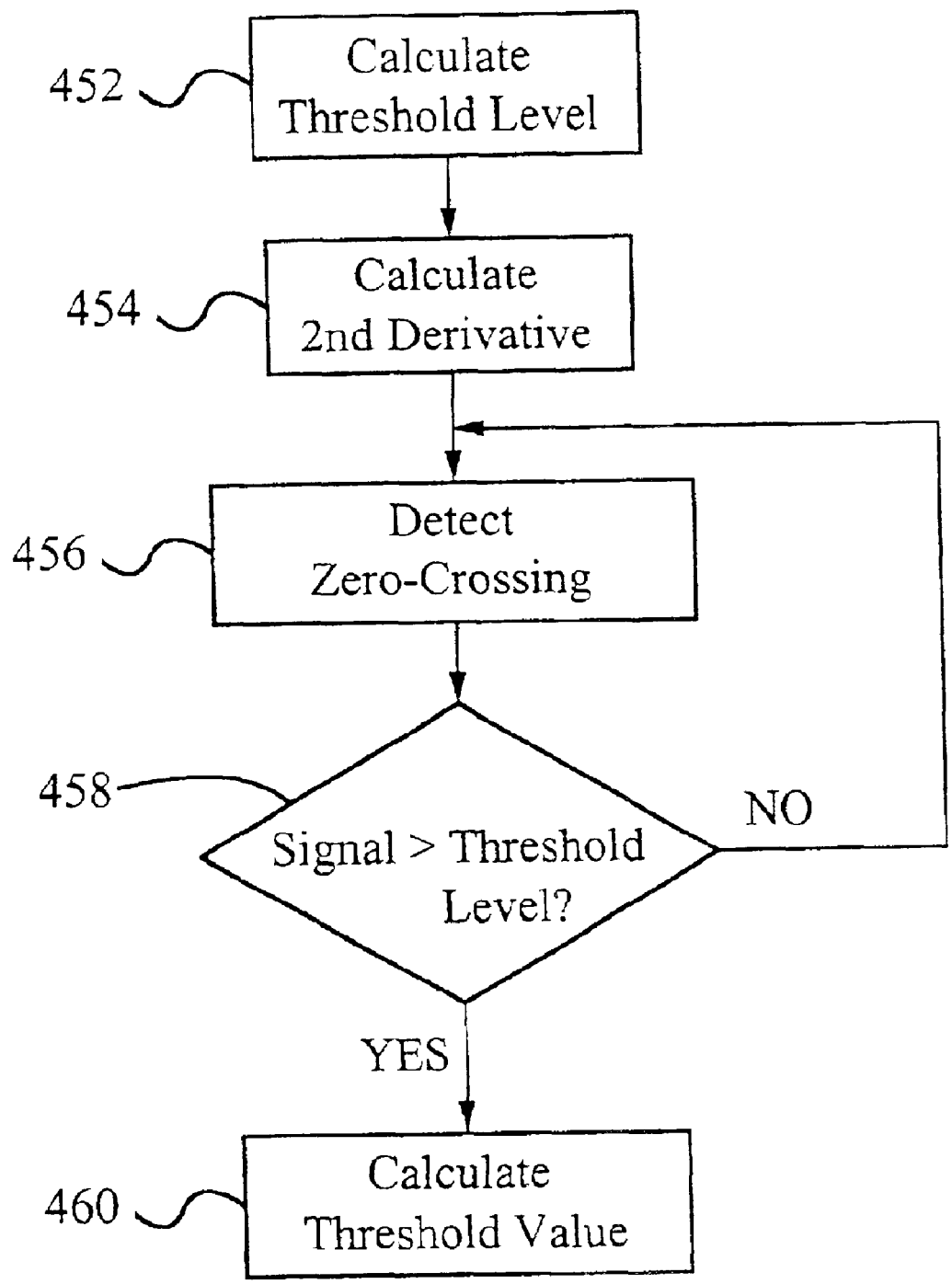
FIG. 33 is a flow chart illustrating steps executed to calculate a threshold value in a nucleic acid amplification reaction according to a second embodiment of the invention.
Figure 34:
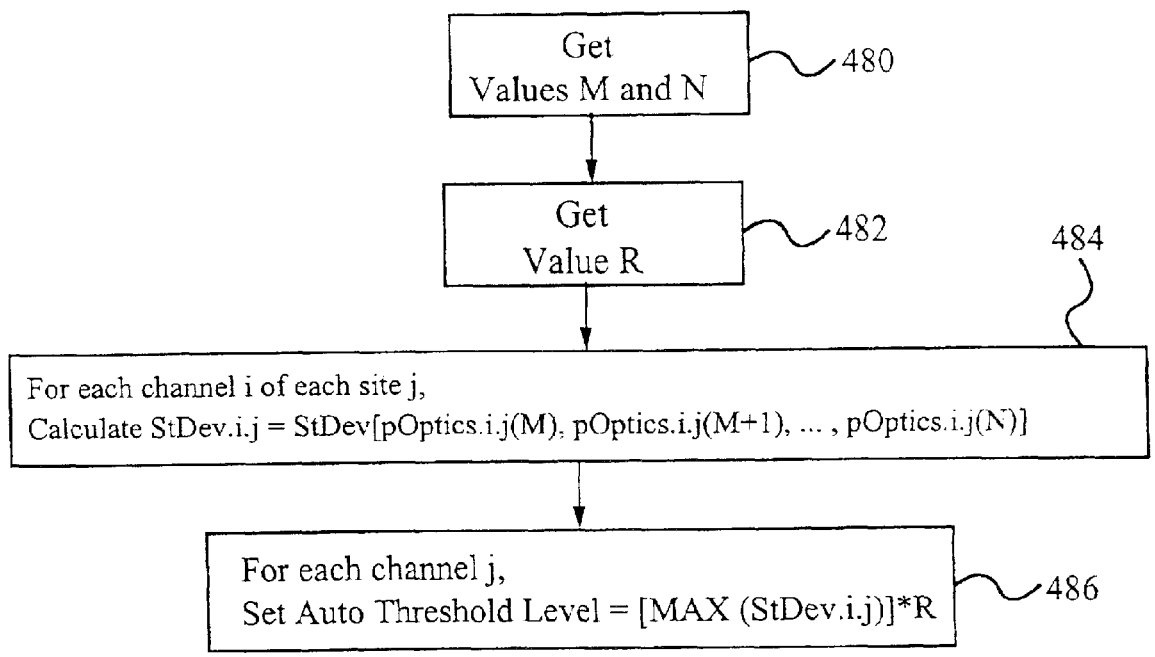
FIG. 34 is a flow chart illustrating the step executed to calculate a noise-based threshold level to be exceeded by a primary optical signal.

FIGS. 32A–32B illustrate another embodiment of the invention in which the zero-crossing of the second derivative of the growth curve is used to calculate the threshold value (e.g., cycle number or time value). FIG. 33 is a flow chart illustrating the steps for calculating the threshold value for a target nucleic acid sequence according to the second embodiment. In step 308, the controller calculates a minimum, noise-based threshold level for the growth curve to exceed. FIG. 34 is a flow chart showing the steps executed by the controller to calculate the threshold level. For each primary detection channel at each reaction site in use, the controller calculates the standard deviation of the deconvolved signal values calculated for the detection channel for cycles M to N (preferably cycles 3 to 8). The controller next sets the threshold level for each detection channel equal to R times the maximum standard deviation calculated for the channel. For example, assume that 8 sites are in use (labeled A1–A8) and the FAM channel is used to detect and measure the growth of a target nucleic acid sequence at each of the sites. For each site, the controller calculates the standard deviation of the FAM channel signal values for cycles M to N and sets the threshold level for each FAM channel equal to R times the largest standard deviation found. M, N, and R are preferably user-defined integers. Reasonable values for M and N are 3 and 8, respectively. The value of R is preferably in the range of 3 to 10, with a preferred value of 5. Although this automatic, noise-based threshold level is presently preferred, the threshold level may also be set manually by a user.

Referring again to FIG. 33, in step 454, the controller calculates a second derivative of the growth curve. Preferably, the controller calculates a plurality of second derivative data points as previously described with reference to FIGS. 28A–28C. In step 456, the controller identifies a zero-crossing of the second derivative. A zero-crossing is detected if the second derivative value at cycle X is less than zero and the second derivative value at cycle X−1 is greater than zero. In decision step 458, it is determined if the deconvolved signal value at cycle X exceeds the threshold level calculated in step 452. If the signal value does not exceed the threshold level, the controller returns to step 456 and looks for the next zero-crossing of the second derivative. If the signal value does exceed the threshold level, the controller proceeds to step 460. In step 460, the controller calculates the threshold value (e.g., the threshold cycle number in thermal cycling amplification or time value in isothermal amplification) as the location of the zero-crossing of the second derivative curve. The threshold value may be calculated by linear interpolation between the second derivative data points at cycle X and X−1.

Figure 35A:
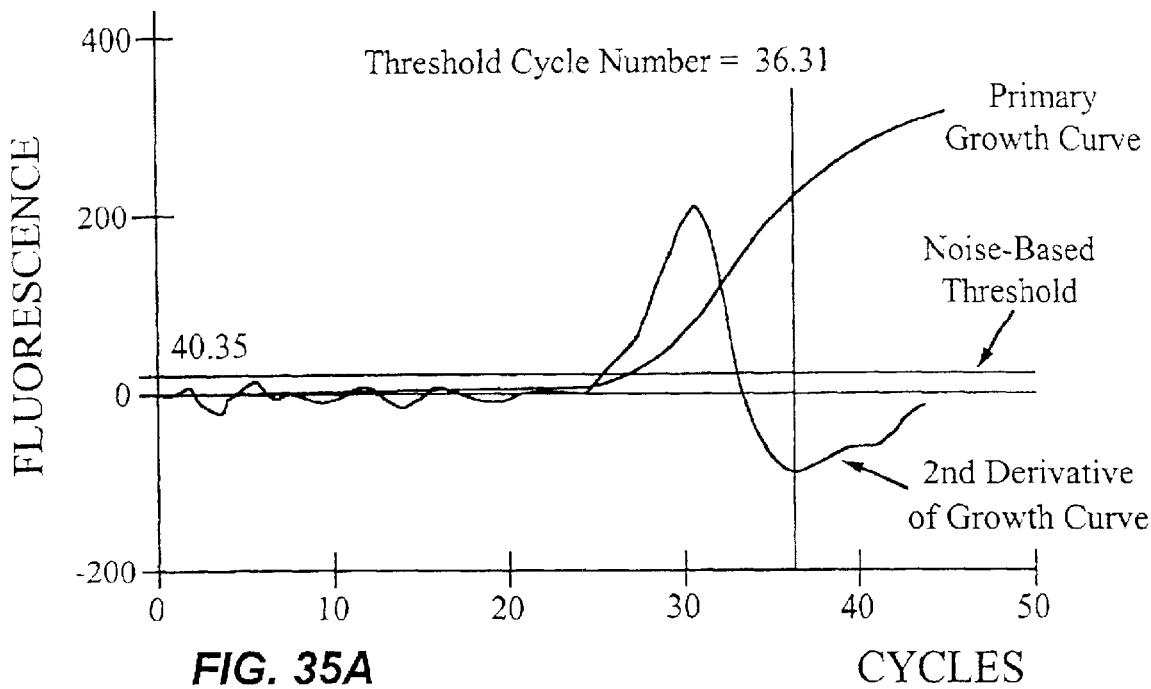
FIG. 35A is a graph showing a growth curve for a thermal cycling nucleic acid amplification reaction. A threshold cycle number is calculated as the location of a negative peak of the second derivative of the growth curve.
Figure 35B:
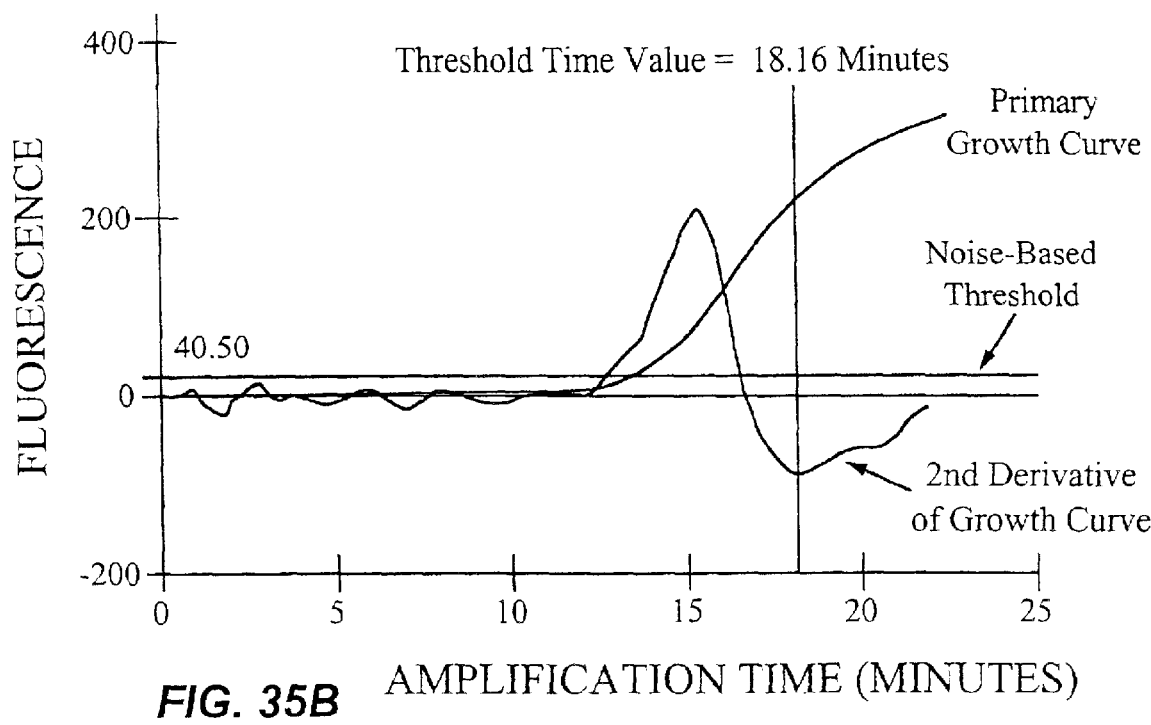
FIG. 35B is a graph showing a growth curve for an isothermal nucleic acid amplification reaction. A threshold time value is calculated as the location of a negative peak of the second derivative of the growth curve.
Figure 36:
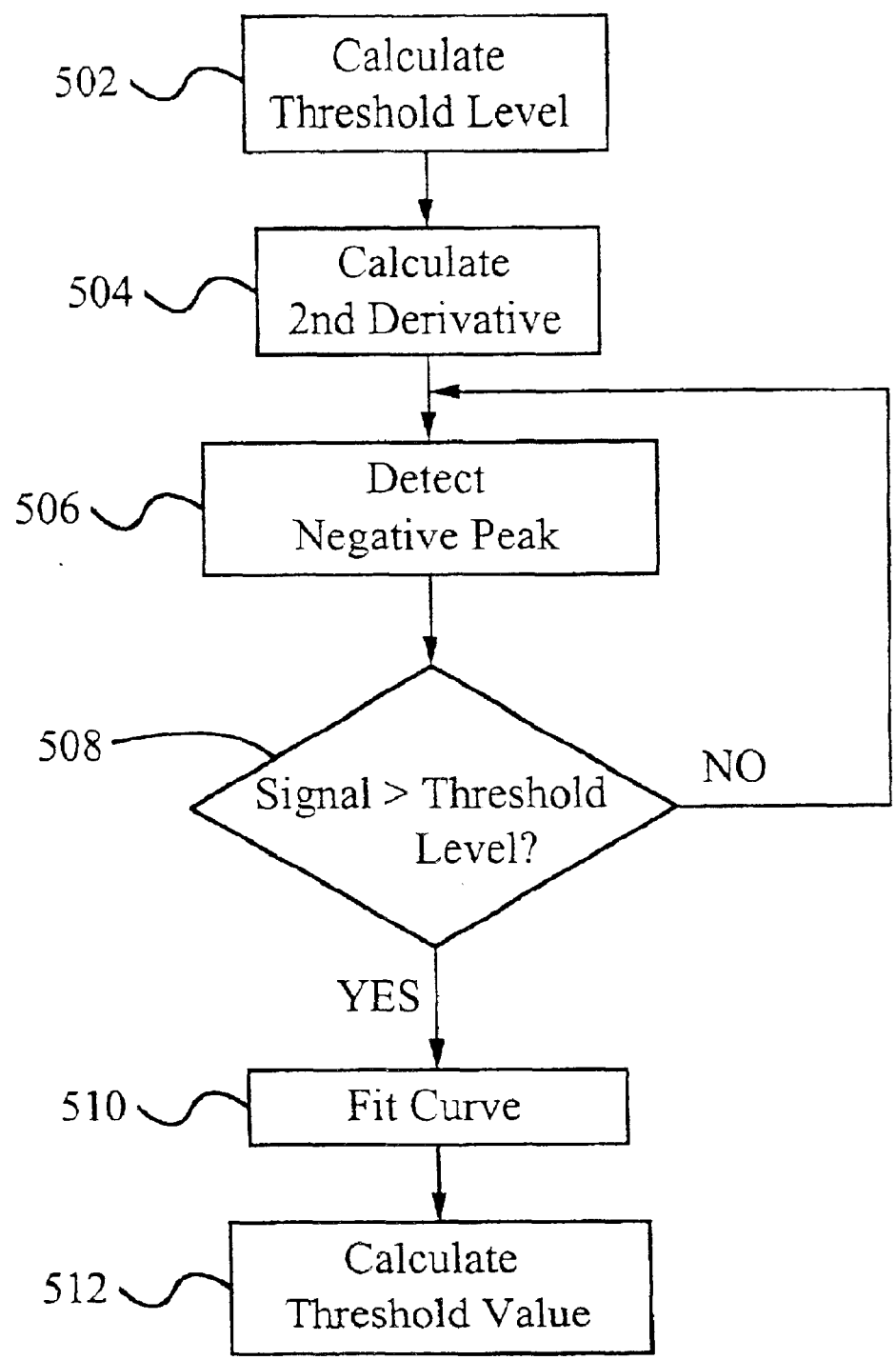
FIG. 36 is a flow chart illustrating steps executed to calculate a threshold value in a nucleic acid amplification reaction according to a third embodiment of the invention.

FIGS. 35A–35B illustrate a third embodiment of the invention in which a negative peak of the second derivative of the growth curve is used to calculate the threshold value (e.g., cycle number or time value). FIG. 36 is a flow chart illustrating the steps for calculating the threshold value for a target nucleic acid sequence according to the third embodiment. In step 502, the controller calculates a minimum, noise-based threshold level for the growth curve to exceed, as previously described with reference to FIG. 34. In step 504, the controller calculates a second derivative of the growth curve. Preferably, the controller calculates a plurality of second derivative data points as previously described with reference to FIGS. 28A–28C. In step 506, the controller identifies a negative peak of the second derivative. A negative peak is detected if the second derivative value at cycle X is less than zero, the second derivative value at cycle X is greater than the second derivative value at cycle X−1, and the second derivative value at cycle X−1 is less than the second derivative value at cycle X−2. In decision step 508, it is determined if the deconvolved signal value at cycle X exceeds the threshold level calculated in step 502. If the signal value does not exceed the threshold level, the controller returns to step 506 and looks for the next negative peak of the second derivative. If the signal value does exceed the threshold level, the controller fits a second order curve to the second derivative data points at cycles X, X−1, and X−2, step 510. In step 512, the controller calculates the threshold value (e.g., the threshold cycle number in thermal cycling amplification or time value in isothermal amplification) as the location of the negative peak (minimum value) of the fitted second order curve.

Figure 37A:
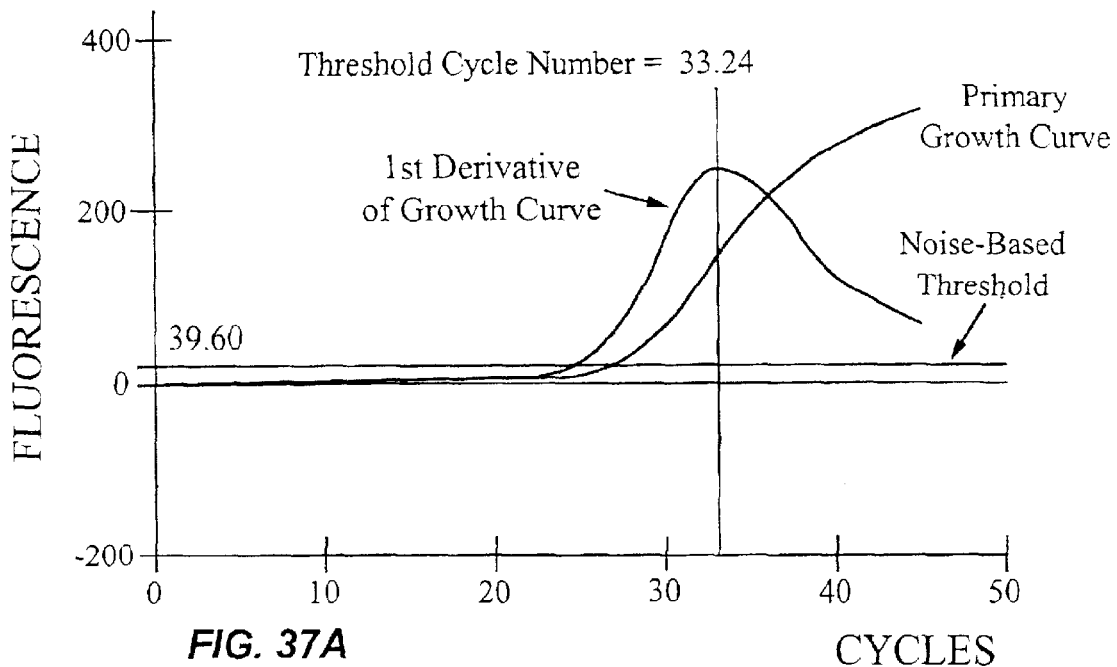
FIG. 37A is a graph showing a growth curve for a thermal cycling nucleic acid amplification reaction. A threshold cycle number is calculated as the location of the positive peak of the first derivative of the growth curve.
Figure 37B:
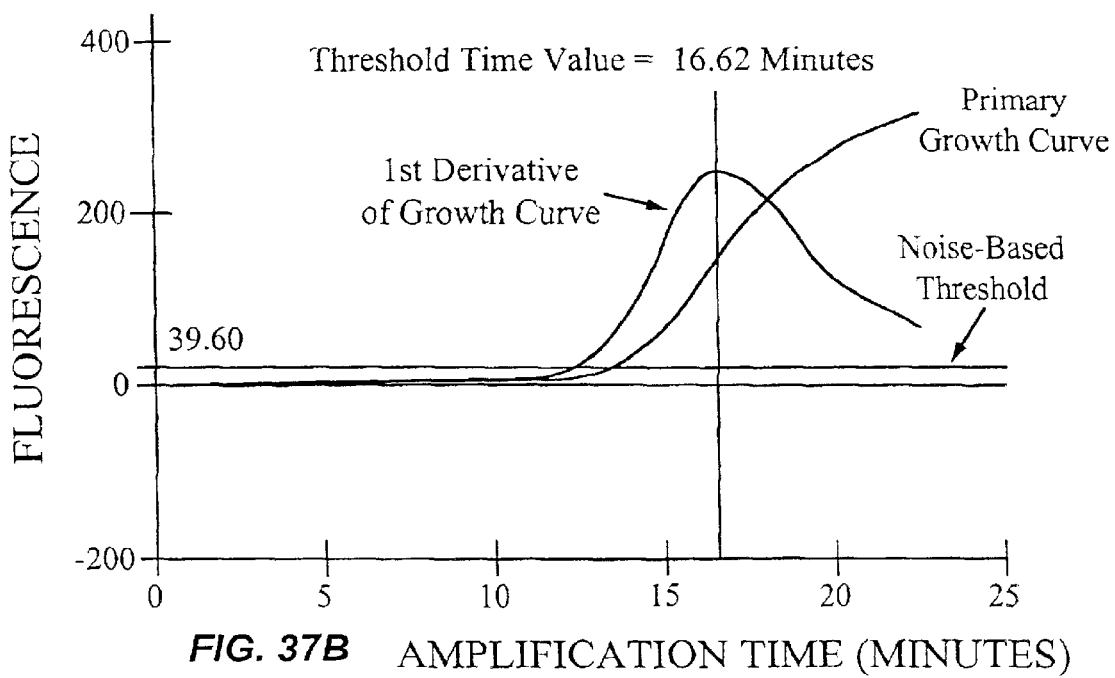
FIG. 37B is a graph showing a growth curve for an isothermal nucleic acid amplification reaction. A threshold time value is calculated as the location of a positive peak of the first derivative of the growth curve.
Figure 38:
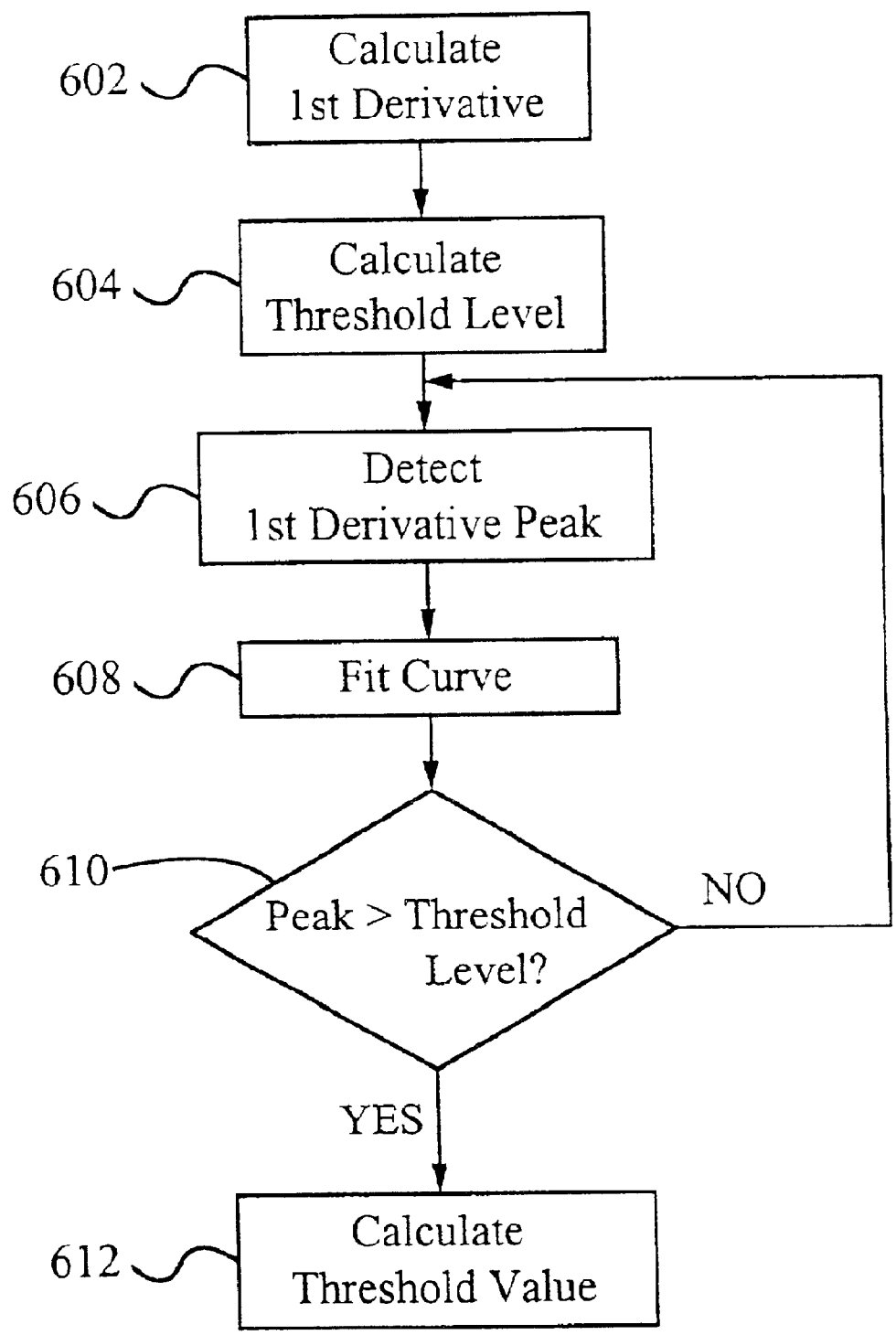
FIG. 38 is a flow chart illustrating steps executed to calculate a threshold value in a nucleic acid amplification reaction according to a fourth embodiment of the invention.

FIGS. 37A–37B illustrate another embodiment of the invention in which the threshold value is calculated as the cycle number or time value associated with the positive peak of the first derivative of the growth curve. It should be noted that the positive peak of the first derivative is mathematically equivalent to the zero-crossing of the second derivative in terms of the x-location, although the y-location will vary between the two. FIG. 38 is a flow chart showing the preferred method steps executed by the controller to determine a threshold value for a nucleic acid sequence using the positive peak (maximum) of the first derivative of the growth curve. In step 602, first derivative data points are calculated from the deconvolved signal values calculated for the nucleic acid sequence.

Preferred methods for calculating the first derivative data points will now be described with reference to FIG. 28A. FIG. 28A shows a segment of a growth curve defined by five consecutive signal values $\{Optic_{(X-4)}, Optic_{(X-3)}, \ldots, Optic_{(X)}\}$ where X is equal to the cycle number (or measurement time point in isothermal amplification) at which the signal was measured. Thus, $Optic_{(X-2)}$ is equal to the signal value two cycles prior to cycle number X. The controller preferably calculates the first derivative (with respect to x) of the growth curve at point $Optic_{(X-1)}$ using equation (3):

$$1stDeriv_{(X-1)} = [Optic_{(X)} - Optics_{(X-2)}]/2; \qquad (3)$$

Equation (3) may be used to calculate the first derivative of the growth curve at any point on the curve for which at least one prior and one subsequent signal value is known. This is not possible, however, for the last signal value on the growth curve. Therefore, a different equation is necessary to calculate a first derivative value at the last point. Still referring to FIG. 28A, the first derivative of the growth curve at point Optic(X) is preferably calculated using equation (10):

$$1stDeriv_{(X)} = Optic_{(X)} - Optics_{(X-1)}; \qquad (10)$$

The controller preferably displays the growth curve and the first derivative of the growth curve to the user in real-time on a graphical user interface. When a new fluorescent signal value Optic(x) is received, the controller calculates a first derivative of the growth curve at Optic(x) using equation (10). When a subsequent signal value Optic (x+1) is received, the controller recalculates the first derivative of the growth curve at Optic(x) using equation (3). Thus, previously calculated first derivative values are updated as new signals are measured.

Figure 39:
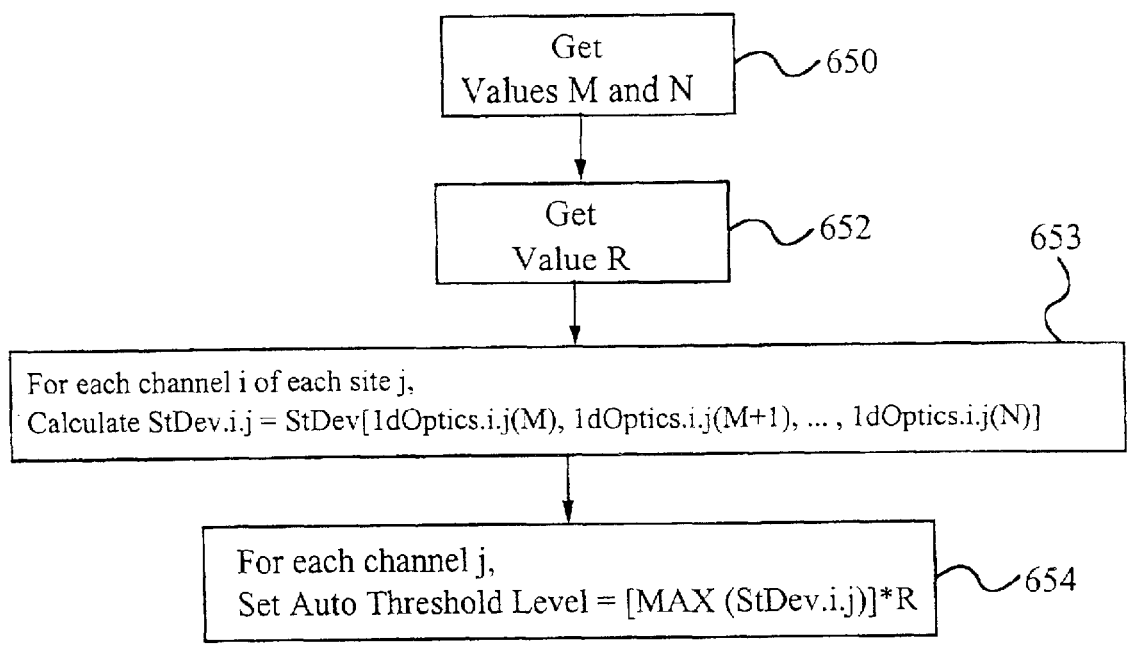
FIG. 39 is a flow chart illustrating the step executed to calculate a noise-based threshold level to be exceeded by a positive peak of a first derivative of a growth curve.

In step 604, the controller calculates a noise-based threshold level for the positive peak of the first derivative to exceed. FIG. 39 is a flow chart showing the steps executed by the controller to calculate the threshold level. For each primary detection channel at each reaction site in use, the controller calculates the standard deviation of the first derivative values calculated for the detection channel for cycles M to N (e.g., cycles 3 to 8). The controller next sets the threshold level for each detection channel equal to R times the maximum standard deviation calculated for the channel. For example, assume that 8 sites are in use (labeled A1–A8) and the FAM channel is used to detect and measure the growth of a target nucleic acid sequence at each of the sites. For each site, based on the deconvolved signal values calculated for the FAM channel for cycles M to N, the controller calculates first derivative data points for cycles M to N. The controller also calculates the standard deviation of the first derivative data points and sets the threshold level for each FAM channel equal to R times the largest standard deviation found. Thus, the reaction site whose FAM channel has the largest standard deviation in the values of its first derivative data points for cycles M to N is used to set the threshold level for all FAM channels in the batch. M, N, and R are preferably user-defined integers. Reasonable default values for M and N are 3 and 8, respectively. A preferred default value for R is 5. Although it is presently preferred to calculate an automatic, noise-based threshold level in this manner, the threshold level may also be set manually by the user.

Referring again to FIG. 38, in step 606, the controller detects a positive peak of the first derivative. The positive peak is preferably detected using at least three first derivative data points calculated at X, X−1, an X−2, where X is equal to the cycle number (or time point of measurement for isothermal amplification). A positive peak is detected if the first derivative value at cycle X is less than the first derivative value at cycle X−1 and if the first derivative value at cycle X−1 is greater than the first derivative value at cycle X−2. After a peak is detected, a second order curve is fit to the three first derivative data points, step 608. In decision step 610, it is determined if the height of the peak of the second order curve exceeds the threshold level calculated in step 604. If the peak of the second order curve does not exceed the threshold level, the controller returns to step 606 and looks for the next positive peak in the first derivative. If the peak of the second order curve does exceed the threshold level, the controller proceeds to step 612. In step 612, the controller calculates the threshold value (e.g., the threshold cycle number in thermal cycling amplification or time value in isothermal amplification) as the location of the peak of the second order curve. The location and height of the peak of the second order curve may be calculated using the algorithm previously described with reference to FIGS. 30–31.

Referring again to FIG. 20, the controller 112 is programmed to calculate and store in memory a respective threshold value for each target nucleic acid sequence that is amplified in each of the reaction vessels 12. The threshold values may be calculated using any of the four methods just described. Next, the controller derives a calibration curve using the threshold values determined for the known starting quantities of the calibration nucleic acid sequence in the calibration samples. The calibration curve relates the threshold value to the log of the starting quantity of the nucleic acid sequence. To determine the unknown starting quantity of the target nucleic acid sequence in the test sample, the threshold value determined for the target sequence in the test sample is entered into the equation of the calibration curve and the equation returns a value that is the starting quantity of the target nucleic acid sequence in the test sample.

The following three examples of operation demonstrate various different methods for using threshold cycle values to determine the unknown starting quantity of a target nucleic acid sequence in a test sample according to the present invention.

EXAMPLE 1

External Standards

Referring to FIG. 20, test samples and calibration samples are amplified in separate reaction vessels 12 at separate reaction sites. In this example, there are sixteen heat-exchanging modules 60 (arranged in two rows of eight). Each heat-exchanging module provides a reaction site for amplifying a sample contained in a reaction vessel. The eight heat-exchanging modules in the first row are designated reaction sites A1–A8 and the eight heat-exchanging exchanging modules in the second row are designated reaction sites B1–B8. Eight calibration samples (standards) are amplified at sites A1–A8 and eight test samples are amplified at sites B1–B8. Each test sample is mixed with the necessary reagents and fluorescent probes to amplify and detect up to three different target nucleic acid sequences. Each calibration sample contains a known starting quantity of three calibration nucleic acid sequences corresponding to the three target nucleic acid sequences in the test samples. Each calibration nucleic acid sequence is preferably the same or similar to a respective one of the target nucleic acid sequences in the test samples.

FIG. 40 shows a schematic representation of a setup table that appears on a graphical user interface of the controller. Prior to amplifying and detecting the nucleic acid sequences in the test and calibration samples, the user enters in the setup table the known starting quantity of each calibration nucleic acid sequence in each calibration sample, as well as the specific dye (e.g., FAM, TET, TAM, or ROX) used to label each nucleic acid sequence. For example, at site A1, the user has specified 1,000 starting copies of a first calibration nucleic acid sequence to be labeled with FAM, 100 starting copies of a second nucleic acid sequence to be labeled with TET, and 10 starting copies of a third nucleic acid sequence to be labeled with TAM. The nucleic acid sequences in the test and calibration samples are then amplified and a threshold value (e.g., cycle number or time value) is determined for each nucleic acid sequence using any of the four methods previously described.

Figures 43, 44:
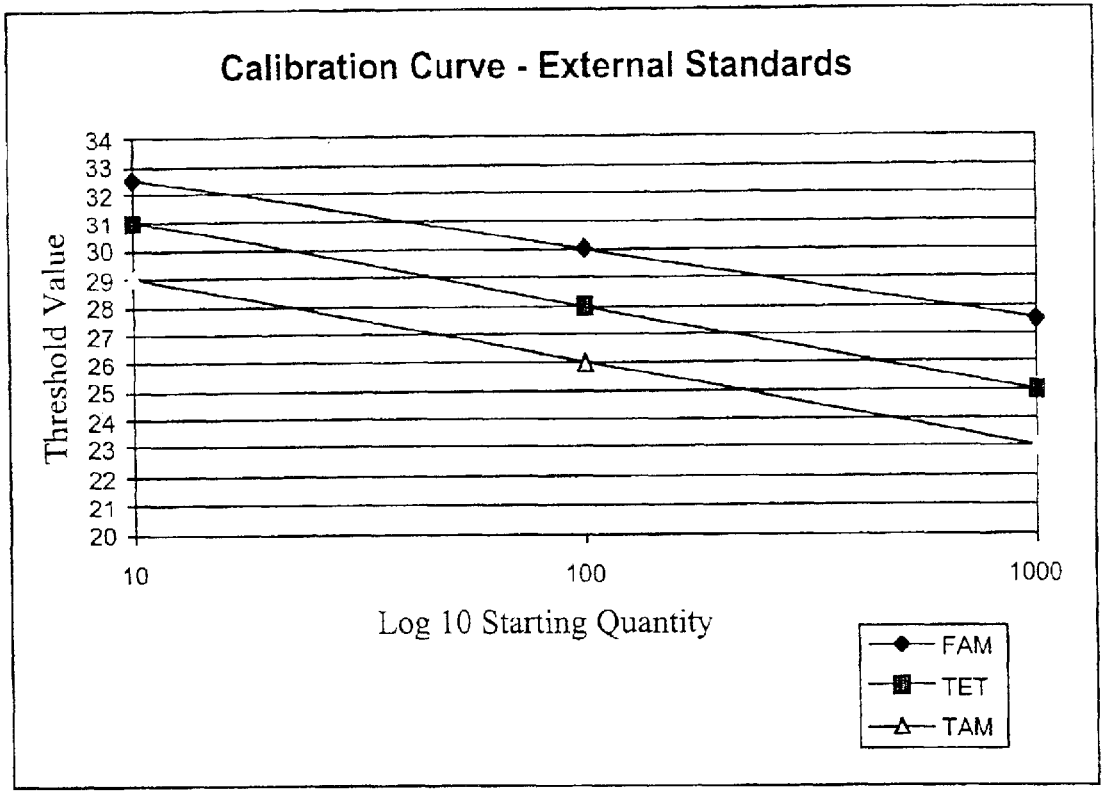
FIG. 43 is a calibration curve derived from the values in the table of FIG. 42.
FIG. 44 is a table of starting quantities of different target nucleic acid sequences in a test sample determined using the calibration curve of FIG. 43.

FIG. 41 is a table showing the threshold values computed by the controller for each of the three nucleic acid sequences (labeled with FAM, TET, and TAM, respectively) in each of the calibration samples. From the data in the table, the controller computes the average threshold value for each calibration nucleic acid sequence at each starting quantity, as shown in FIG. 42. As shown in FIG. 43, the controller next generates three calibration curves, one for each calibration nucleic acid sequence. Each calibration curve relates threshold value to the log of the starting quantity of a nucleic acid sequence. Each calibration curve is preferably generated using a least squares algorithm to fit a line to the data points.

To determine the unknown starting quantity of each of the three target nucleic acid sequences in a test sample, a respective threshold value is determined for each target sequence. The threshold value is then entered into the equation of the corresponding calibration curve and the equation returns a value that is the starting quantity of the target nucleic acid sequence in the test sample. For example, FIG. 44 shows the results determined for one of the test samples. The first target nucleic acid sequence in the test sample (labeled with FAM) had a threshold value of 29 corresponding to a starting quantity of 251 copies, the second target nucleic acid sequence in the test sample (labeled with TET) had a threshold value of 29 corresponding to a starting quantity of 46 copies, and the third target nucleic acid sequence in the test sample (labeled with TAMRA) had a threshold value of 24 corresponding to a starting quantity of 464 copies.

EXAMPLE 2

Quantitative Internal Controls

This example is similar to example 1, except that in example 2 each threshold value determined for a nucleic acid sequence is normalized by the threshold value determined for a quantitative internal control. Referring to FIG. 20, test samples and calibration samples are amplified in separate reaction vessels 12 at separate reaction sites. Eight calibration samples (standards) are amplified at sites A1–A8 and eight test samples are amplified at sites B1–B8. Each test sample is mixed with the necessary reagents and fluorescent probes to amplify and detect up to two different target nucleic acid sequences. Each calibration sample contains a known starting quantity of two different calibration nucleic acid sequences corresponding to the two target nucleic acid sequences in the test samples. In addition, a known quantity of a quantitative internal control (QIC) is placed in each test and calibration sample. The quantitative internal control is a nucleic acid sequence different than the calibration and target nucleic acid sequences in the samples and is used to normalize the threshold values determined for the target and calibration sequences. Suitable nucleic acid sequences to be used as a QIC include, e.g., beta-actin, glyceraldehyde-3-phosphate dehydrogenase (GAPDH), or any synthetic, amplifiable target. The same starting quantity of the QIC is placed in each test and calibration sample. The starting quantity of the QIC placed in each sample is preferably in the range of about 10 to 1,000 copies, with a preferred starting quantity of about 100 copies.

FIG. 45 shows a schematic representation of a setup table that appears on a graphical user interface of the controller. Prior to amplifying and detecting the nucleic acid sequences in the test and calibration samples, the user enters in the setup table the known starting quantity of each calibration nucleic acid sequence in each calibration sample, as well as the specific dye (e.g., FAM, TET, TAM, or ROX) used to label each nucleic acid sequence. For example, at site A1, the user has specified 1,000 starting copies of a first calibration nucleic acid sequence to be labeled with FAM, and 100 starting copies of a second nucleic acid sequence to be labeled with TET. In this example, TAM is the dye used to label the QIC and the user is therefore prevented from entering values for TAM in the standards column. The nucleic acid sequences in the test and calibration samples (each containing the same starting quantity of a QIC) are then amplified and a threshold value is determined for each nucleic acid sequence, preferably using any of the four methods previously described. Alternatively, threshold values may be determined using any of the methods known in the art.

Figures 49, 50:
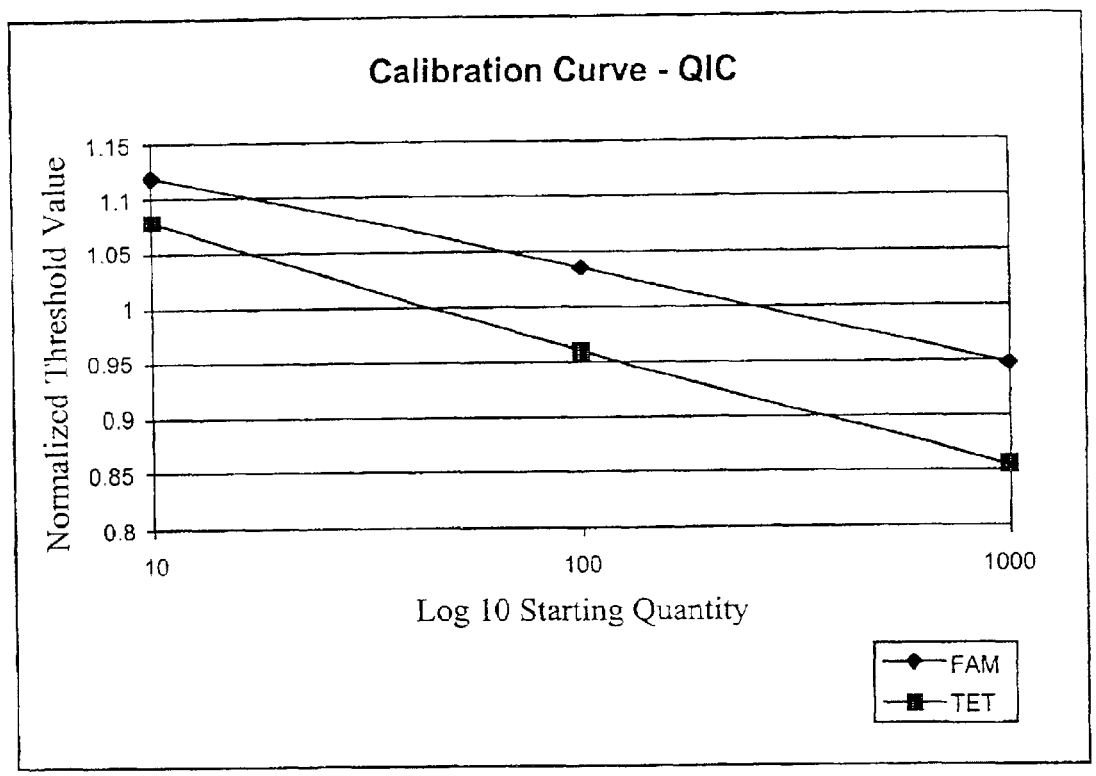
FIG. 49 is a calibration curve derived from the values in the table of FIG. 48.
FIG. 50 is a table of starting quantities of different target nucleic acid sequences in a test sample computed using the calibration curve of FIG. 49.

FIG. 46 is a table showing the threshold values computed by the controller for each of the two calibration nucleic acid sequences (labeled with FAM and TET) and of the QIC (labeled with TAM) in each of the calibration samples. As shown in the table of FIG. 47, the threshold values for each calibration nucleic acid sequence are normalized to the corresponding QIC by dividing the threshold values of the calibration sequences by the threshold values of the QIC. The controller next computes the average normalized threshold value for each calibration nucleic acid sequence at each starting quantity, as shown in FIG. 48. As shown in FIG. 49, the controller derives two calibration curves, one for each calibration nucleic acid sequence. Each calibration curve relates normalized threshold value to the log of the starting quantity of a nucleic acid sequence. Each calibration curve is preferably generated using a least squares algorithm to fit a line to the data points.

Referring to FIG. 50, to determine the unknown starting quantity of each of the two target nucleic acid sequences in a test sample, a respective threshold value is determined for each target sequence and for the QIC amplified in the same reaction with the target sequences. The threshold values determined for the target sequences are then divided by the threshold value determined for the QIC to normalize the threshold values to the QIC. Each normalized threshold value is then entered into the equation of the corresponding calibration curve and the equation returns a value that is the starting quantity of the target nucleic acid sequence in the test sample. For example, FIG. 50 shows the results determined for one of the test samples. The first target nucleic acid sequence in the test sample (labeled with FAM) has a normalized threshold value of 1.006944 corresponding to a starting quantity of 210 copies, and the second target nucleic acid sequence in the test sample (labeled with TET) has a normalized threshold value of 1.041667 corresponding to a starting quantity of 21 copies.

EXAMPLE 3

Internal Standards

In this example, the calibration nucleic acid sequences (standards) are amplified together in the same reaction vessel with the unknown quantity of a target nucleic acid sequence in a test sample. Referring to FIG. 20, eight reaction vessels containing reaction mixtures are placed at sites A1–A8. The reaction mixture in each vessel comprises (1) a test sample mixed with the necessary reagents and fluorescent probes to amplify and detect a target nucleic acid sequence in the test sample; (2) a first internal standard comprising a known quantity of a second nucleic acid sequence different than the target sequence in the test sample, as well as the necessary reagents and probes to amplify and detect the second nucleic acid sequence; and (3) a second internal standard comprising a known quantity of a third nucleic acid sequence different than the target sequence in the test sample and the second nucleic acid sequence, as well as the necessary reagents and probes to amplify and detect the third nucleic acid sequence.

FIG. 51 shows a schematic representation of a setup table that appears on a graphical user interface of the controller. Prior to amplifying and detecting the nucleic acid sequences in the reaction mixtures, the user enters in the setup table the known starting quantity of the second and third nucleic acid sequences (the internal standards) in each reaction mixture, as well as the specific dye (e.g., FAM, TET, TAM, or ROX) used to label each nucleic acid sequence. For example, at site A1, the user has specified 100 starting copies of the first internal standard to be labeled with TET, and 1000 starting copies of the second internal standard to be labeled with TAM. In this example, FAM is the dye used to label the target nucleic acid sequence in the test sample and the user is therefore prevented from entering starting copy numbers for FAM in the standards column. The nucleic acid sequences in the reaction mixtures (each containing an unknown quantity of a target sequence and known starting quantities of two internal standards) are then amplified and a threshold value is determined for each nucleic acid sequence, preferably using any of the four methods previously described. Alternatively, threshold values may be determined using any of the methods known in the art.

Figures 53, 54:
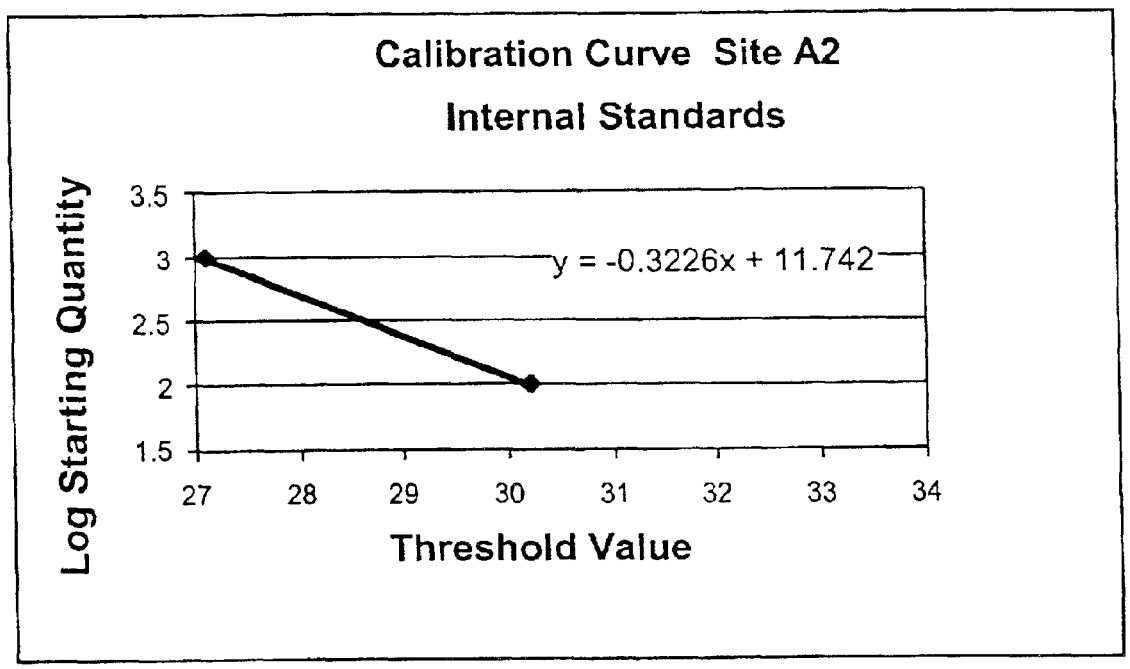
FIG. 53 is a table of threshold values and known starting quantities of the calibration nucleic acid sequences amplified at one of the reaction sites specified in FIG. 52.
FIG. 54 is a calibration curve derived from the values in the table of FIG. 53.

FIG. 52 is a table showing the threshold values computed by the controller for the target sequence and first and second standards at each reaction site. Next, a calibration curve is generated for each individual site based on the threshold values determined for the two internal standards. For example, FIG. 54 shows the calibration curve generated for site A2. The threshold values and known starting quantities of the two internal standards provide two data points to which a calibration line is fit. To determine the unknown starting quantity of the target nucleic acid sequence in the test sample amplified at site A2, the threshold value determined for the target sequence is then entered into the equation of the calibration curve and the equation returns a value that is the starting quantity of the target nucleic acid sequence in the test sample. For example, if the target sequence is determined to have a threshold value of 29.9. then the starting quantity is calculated as 124.81 copies.

One advantage to using internal standards is that a calibration curve is developed based only on the reaction in which the unknown quantity of the target nucleic acid sequence is being amplified. Consequently, the method reduces problems arising from the variability between reactions occurring in different reaction vessels. Another advantage of the method is that it reduces the number of reaction sites and the amount of expensive reagents required to perform an assay.

SUMMARY RAMIFICATIONS, AND SCOPE

Although the above description contains many specificities, it is to be understood that many different modifications or substitutions may be made to the methods, apparatus, and computer program products described without departing from the broad scope of the invention. For example, the means for amplifying the test or calibration samples need not be the specialized thermal cycler described herein. The means for amplifying the test and calibration samples may comprise a metal block having a plurality of wells for receiving the samples. Alternatively, the means for amplifying the test and calibration samples may comprise a forced air system for heating and cooling samples contained in capillary tubes. These and other apparatuses for amplifying and detecting nucleic acid are known in the art.

Moreover, the controller for controlling the operation of the apparatus may be a personal or network computer linked to the heat-exchanger or may comprise a microprocessor and memory built into the heat-exchanging instrument. The computer program product (e.g., software) readable by the controller may comprise a storage medium (e.g., a disk) embodying the program instructions. Alternatively, the computer program product may be an electronic file stored in the memory of the controller or downloadable to the controller. Further, the specialized reaction vessels described above are preferred, but the apparatus and methods of the present invention are applicable to any type of vessel including plastic reaction tubes, glass capillary tubes, microtiter plates, cartridges or cuvettes, etc.

In addition, the threshold value (e.g., cycle number or time value) determined using the methods of the present invention has other uses besides quantitation of an unknown quantity of a nucleic acid sequence. For example, the threshold value may be used to determine an optimal termination point for a nucleic acid amplification reaction so that the reaction may be terminated prior to reaching the plateau phase to prevent degradation of amplicons and/or accumulation of undesired products (e.g., primer dimers).

Further, the mathematical methods described above for calculating derivatives and threshold criteria are examples only and other methods may be used to obtain similar data. For example, one could fit a mathematical function as an approximation to an entire growth curve and then calculate derivatives based on that function. Moreover, the terminology in the claims related to the steps of deriving growth curves, calculating derivatives, deriving calibration curves, and/or fitting curves to data points is intended to include the processing of data (e.g., x-y data) and variables internal to a processing unit (e.g., a computer) containing memory and is not limited to the physical acts of printing, plotting, or displaying lines, curves, or graphs.

Therefore, the scope of the invention should be determined by the following claims and their legal equivalents.

What is claimed is:

1. An apparatus for determining a threshold cycle number in a nucleic acid amplification reaction, the apparatus comprising:
   a) a thermal cycler suitable for a nucleic acid amplification reaction;
   b) at least one detection mechanism for measuring, at a plurality of different times during an amplification reaction conducted using the thermal cycler, at least one signal whose intensity is related to the quantity of a nucleic acid sequence being amplified in the reaction; and
   c) a controller in communication with the detection mechanism, wherein the controller is programmed to perform the steps of:
      i) deriving a growth curve from the measurements of the signal;
      ii) calculating a derivative of the growth curve;
      iii) identifying a characteristic of the derivative; and
      iv) determining the threshold cycle number associated with the characteristic of the derivative.

2. The apparatus of claim 1, wherein the controller is programmed to calculate a second derivative of the growth curve, and wherein the characteristic comprises a positive peak of the second derivative.

3. The apparatus of claim 1, wherein the controller is programmed to calculate a second derivative of the growth curve, and wherein the characteristic comprises a negative peak of the second derivative.

4. The apparatus of claim 1, wherein the controller is programmed to calculate a second derivative of the growth curve, and wherein the characteristic comprises a zero crossing of the second derivative.

5. The apparatus of claim 1, wherein the controller is programmed to calculate a first derivative of the growth curve, and wherein the characteristic comprises a positive peak of the first derivative.

6. The apparatus of claim 1, wherein the controller is programmed to calculate second derivative values of the growth curve at a number of different cycles in the reaction to yield a plurality of second derivative data points, the characteristic comprises a positive peak of the second derivative, and the controller is further programmed to determine the threshold cycle number associated with the positive peak by:
  i) fitting a second order curve to the second derivative data points; and
  ii) calculating the threshold cycle number as the location, in cycles, of a peak of the second order curve.

7. The apparatus of claim 2, wherein the controller is further programmed to perform the steps of calculating a noise-based threshold level and determining if the positive peak exceeds the noise-based threshold level.

8. The apparatus of claim 2, wherein the controller is further programmed to perform the step of determining if the positive peak exceeds a user-defined threshold level.

9. The apparatus of claim 2, wherein the controller is further programmed to perform the steps of calculating a noise-based threshold level and determining if the growth curve exceeds the noise-based threshold level at the threshold cycle number.

10. The apparatus of claim 2, wherein the controller is further programmed to perform the step of determining if the growth curve exceeds a user-defined threshold level at the threshold cycle number.

11. The apparatus of claim 3, wherein the controller is further programmed to perform the steps of calculating a noise-based threshold level and determining if the growth curve exceeds the noise-based threshold level at the threshold cycle number.

12. The apparatus of claim 3, wherein the controller is further programmed to perform the step of determining if the growth curve exceeds a user-defined threshold level at the threshold cycle number.

13. The apparatus of claim 4, wherein the controller is further programmed to perform the steps of calculating a noise-based threshold level and determining if the growth curve exceeds the noise-based threshold level at the threshold cycle number.

14. The apparatus of claim 4, wherein the controller is further programmed to perform the step of determining if the growth curve exceeds a user-defined threshold level at the threshold cycle number.

15. The apparatus of claim 5, wherein the controller is further programmed to perform the steps of calculating a noise-based threshold level and determining if the positive peak exceeds the noise-based threshold level.

16. The apparatus of claim 5, wherein the controller is further programed to perform the step of determining if the positive peak exceeds a user-defined threshold level.

17. The apparatus of claim 5, wherein the controller is further programmed to perform the steps of calculating a noise-based threshold level and determining if the growth curve exceeds the noise-based threshold level at the threshold cycle number.

18. The apparatus of claim 5, wherein the controller is further programmed to perform the step of determining if the growth curve exceeds a user-defined threshold level at the threshold cycle number.

19. The apparatus of claim 6, wherein the controller is further programmed to perform the steps of calculating a noise-based threshold level and determining if the peak of the second order curve exceeds the noise-based threshold level.

20. The apparatus of claim 6, wherein the controller is further programmed to perform the step of determining if the peak of the second order curve exceeds a user-defined threshold level.

21. The apparatus of claim 6, wherein the controller is further programmed to perform the steps of calculating a noise-based threshold level and determining if the growth curve exceeds the noise-based threshold level at the threshold cycle number.

22. The apparatus of claim 6, wherein the controller is further programmed to perform the step of determining if the growth curve exceeds a user-defined threshold level at the threshold cycle number.

23. An apparatus for determining a threshold cycle number in a nucleic acid amplification reaction, the apparatus comprising:
  a) a thermal cycler suitable for a nucleic acid amplification reaction;
  b) at least one detection mechanism for measuring, at a plurality of different times during the amplification reaction, at least one signal whose intensity is related to the quantity of a nucleic acid sequence being amplified in the reaction; and
  b) a controller in communication with the detection mechanism and thermal cycler, wherein the controller is programmed to perform the steps of:
    i) storing signal values defining a growth curve for the nucleic acid sequence, wherein the growth curve expresses signal intensity as a function of cycle number in the reaction;
    ii) determining a derivative of the growth curve, wherein the derivative is determined with respect to cycle number; and
    iii) calculating the threshold cycle number associated with a characteristic of the derivative.

24. The apparatus of claim 23, wherein the controller is further programmed to identify the characteristic of the derivative as the amplification reaction is occurring and to terminate the amplification reaction when the characteristic is identified.

25. The apparatus of claim 23, wherein the controller is programmed to determine the second derivative of the growth curve, and wherein the threshold cycle number is calculated as the location, in cycles, of a maximum of the second derivative.

26. The apparatus of claim 23, wherein the controller is programmed to determine the second derivative of the growth curve, and wherein the threshold cycle number is calculated as the location, in cycles, of a minimum of the second derivative.

27. The apparatus of claim 23, wherein the controller is programmed to determine the second derivative of the growth curve, and wherein the threshold cycle number is calculated as the location, in cycles, of a zero-crossing of the second derivative.

28. The apparatus of claim 23, wherein the controller is programmed to determine the first derivative of the growth curve, and wherein the threshold cycle number is calculated as the location, in cycles, of a maximum of the first derivative.

29. The apparatus of claim 23, wherein the characteristic of the derivative comprises a maximum of the second derivative, and wherein the controller is programmed to perform steps (ii) and (iii) by:
  calculating second derivative values of the growth curve, with respect to cycle number, at a number of different measurement points to yield a plurality of second derivative data points;
  fitting a second curve to at least three of the second derivative data points; and calculating the threshold cycle number as the location, in cycles, of a positive peak of the second curve.

30. The apparatus of claim 23, wherein the characteristic of the derivative comprises a minimum of the second derivative, and wherein the controller is programmed to perform steps (ii) and (iii) by:

calculating second derivative values of the growth curve, with respect to cycle number, at a number of different measurement points to yield a plurality of second derivative data points;

fitting a second curve to at least three of the second derivative data points; and calculating the threshold cycle number as the location, in cycles, of a negative peak of the second curve.

31. The apparatus of claim 23, wherein the characteristic of the derivative comprises a maximum of the first derivative, and wherein the controller is programmed to perform steps (ii) and (iii) by:

calculating first derivative values of the growth curve, with respect to cycle number, at a number of different measurement points to yield a plurality of first derivative data points;

fitting a second curve to at least three of the first derivative data points; and calculating the threshold cycle number as the location, in cycles, of a peak of the second curve.

32. The apparatus of claim 23, wherein the characteristic of the derivative comprises a zero-crossing of the second derivative, and wherein the controller is programmed to perform steps (ii) and (iii) by:

calculating second derivative values of the growth curve at a number of different measurement points to yield a plurality of second derivative data points; and calculating the threshold cycle number at the zero-crossing by interpolation between at least two of the second derivative data points.

33. The apparatus of claim 25, wherein the controller is further programmed to perform the steps of calculating a noise-based threshold level and determining if the maximum of the second derivative exceeds the noise-based threshold level.

34. The apparatus of claim 25, wherein the controller is further programmed to perform the step of determining if the maximum of the second derivative exceeds a user-defined threshold level.

35. The apparatus of claim 25, wherein the controller is further programmed to perform the steps of calculating a noise-based threshold level and determining if the growth curve exceeds the noise-based threshold level at the threshold cycle number.

36. The apparatus of claim 25, wherein the controller is further programmed to perform the step of determining if the growth curve exceeds a user-defined threshold level at the threshold cycle number.

37. The apparatus of claim 26, wherein the controller is further programmed to perform the steps of calculating a noise-based threshold level and determining if the growth curve exceeds the noise-based threshold level at the threshold cycle number.

38. The apparatus of claim 26, wherein the controller is further programmed to perform the step of determining if the growth curve exceeds a user-defined threshold level at the threshold cycle number.

39. The apparatus of claim 27, wherein the controller is further programmed to perform the steps of calculating a noise-based threshold level and determining if the growth curve exceeds the noise-based threshold level at the threshold cycle number.

40. The apparatus of claim 27, wherein the controller is further programmed to perform the step of determining if the growth curve exceeds a user-defined threshold level at the threshold cycle number.

41. The apparatus of claim 28, wherein the controller is further programmed to perform the steps of calculating a noise-based threshold level and determining if the maximum of the first derivative exceeds the noise-based threshold level.

42. The apparatus of claim 28, wherein the controller is further programmed to perform the step of determining if the maximum of the first derivative exceeds a user-defined threshold level.

43. The apparatus of claim 28, wherein the controller is further programmed to perform the steps of calculating a noise-based threshold level and determining if the growth curve exceeds the noise-based threshold level at the threshold cycle number.

44. The apparatus of claim 28, wherein the controller is further programmed to perform the step of determining if the growth curve exceeds a user-defined threshold level at the threshold cycle number.

45. The apparatus of claim 29, wherein the threshold cycle number at the peak of the second curve is calculated using ratios of determinants, and wherein the determinants are calculated using the three second derivative data points.

46. The apparatus of claim 29, wherein the controller is further programmed to perform the steps of calculating a noise-based threshold level and determining if the peak of the second curve exceeds the noise-based threshold level.

47. The apparatus of claim 29, wherein the controller is further programmed to perform the step of determining if the peak of the second curve exceeds a user-defined threshold level.

48. The apparatus of claim 29, wherein the controller is further programmed to perform the steps of calculating a noise-based threshold level and determining if the growth curve exceeds the noise-based threshold level at the threshold cycle number.

49. The apparatus of claim 29, wherein the controller is further programmed to perform the step of determining if the growth curve exceeds a user-defined threshold level at the threshold cycle number.

50. The apparatus of claim 30, wherein the threshold cycle number at the peak of the second curve is calculated using ratios of determinants, and wherein the determinants are calculated using the three second derivative data points.

51. The apparatus of claim 31, wherein the threshold cycle number at the peak of the second curve is calculated using ratios of determinants, and wherein the determinants are calculated using the three first derivative data points.

* * * * *